(12) United States Patent
Chong et al.

(10) Patent No.: US 12,344,870 B2
(45) Date of Patent: Jul. 1, 2025

(54) COMPOSITIONS COMPRISING A CRISPR NUCLEASE AND USES THEREOF

(71) Applicant: Arbor Biotechnologies, Inc., Cambridge, MA (US)

(72) Inventors: Shaorong Chong, Arlington, MA (US); Quinton Norman Wessells, Cambridge, MA (US); Roy Ziblat, Newton, MA (US); Noah Michael Jakimo, Cambridge, MA (US); Anthony James Garrity, Hingham, MA (US); Lauren E. Alfonse, Boston, MA (US)

(73) Assignee: Arbor Biotechnologies, Inc., Cambridge, MA (US)

( * ) Notice: Subject to any disclaimer, the term of this patent is extended or adjusted under 35 U.S.C. 154(b) by 0 days.

(21) Appl. No.: 17/930,595

(22) Filed: Sep. 8, 2022

(65) Prior Publication Data
US 2023/0235304 A1   Jul. 27, 2023

Related U.S. Application Data

(60) Provisional application No. 63/296,741, filed on Jan. 5, 2022, provisional application No. 63/241,821, filed on Sep. 8, 2021.

(51) Int. Cl.
C12N 9/22    (2006.01)

(52) U.S. Cl.
CPC .............. *C12N 9/22* (2013.01); *C12Y 301/25* (2013.01); *C12N 2310/20* (2017.05)

(58) Field of Classification Search
CPC .... C12N 9/22; C12N 2310/20; C12N 15/113; C12N 15/907; C12Y 301/25
See application file for complete search history.

(56) References Cited

U.S. PATENT DOCUMENTS

2016/0046961 A1   2/2016   Charpentier et al.

FOREIGN PATENT DOCUMENTS

| WO | 2018035250 A1 | 2/2018 |
|---|---|---|
| WO | 2020018142 A1 | 1/2020 |
| WO | 2023039472 A2 | 3/2020 |
| WO | 2020180699 A1 | 9/2020 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Stamps et al., "MAG: hypothetical protein EQ97_17255 [Desulfurellales bacterium]." Genbank entry (online). National Institute of Biotechnology Information (2019).
Birren et al., "Aspergillus terreus NIH2624 predicted protein (ATEG_00662) partial mRNA." Genbank entry (online). National Institute of Biotechnology Information (2008).
UniProt ADA1Q3VJN9_9GAMM, Apr. 12, 2017 [online]. [Retrieved Jul. 6, 2020].
Yan et al., "Casl3d Is a Compact RNA-Targeting Type VI CRISPR Effector Positively Modulated by a WYL-Domain-Containing Accessory Protein", Molecular Cell (2018) vol. 70, No. 2, pp. 327-339.
International Search Report and Written Opinion for International Application No. PCT/US2020/020426 dated Jul. 21, 2020.
International Search Report and Written Opinion for International Application No. PCT/US2018/068007 dated Aug. 4, 2019.
Stamps et al., "MAG: hypothetical protein EQ97_17255 [Desulfurellales bacterium]." Genbank entry (online). National Institute of Biotechnology Information (2019) Genbank Accession No. THX51828.1.
Lou, "MAG: transposase [Clostridiales bacterium]." Genbank entry (online). National Institute of Biotechnology Information (2021) GenBank Accession No. MBS5317580.1.
Birren et al., "Aspergillus terreus NIH2624 predicted protein (ATEG_00662) partial mRNA." Genbank entry (online). National Institute of Biotechnology Information (2008) NCBI Reference Sequence No. XM_001210748.1.
Naeem et al., Genbank entry (online). National Institute of Biotechnology Information (2019) GenBank Accession No. LR589468.1.

* cited by examiner

*Primary Examiner* — Delia M Ramirez
(74) *Attorney, Agent, or Firm* — K&L Gates LLP

(57) ABSTRACT

The present disclosure relates to variant polypeptides, methods of preparing the variant polypeptides, processes for characterizing the variant polypeptides, compositions and cells comprising the variant polypeptides, and methods of using the variant polypeptides. The disclosure further relates to complexes comprising the variant polypeptides, methods of producing the complexes, processes for characterizing the complexes, cells comprising the complexes, and methods of using the complexes.

20 Claims, 1 Drawing Sheet
Specification includes a Sequence Listing.

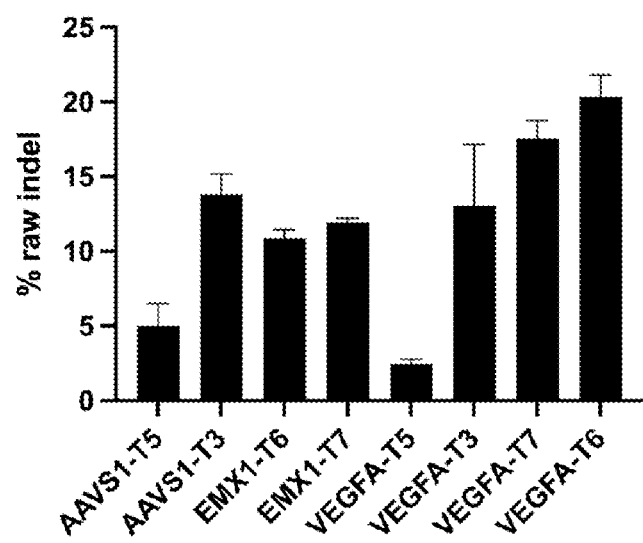

US 12,344,870 B2

COMPOSITIONS COMPRISING A CRISPR NUCLEASE AND USES THEREOF

CROSS REFERENCE TO RELATED APPLICATION

This application claims the benefit of U.S. Provisional Application No. 63/241,821, filed Sep. 8, 2021, and U.S. Provisional Application No. 63/296,741, filed Jan. 5, 2022. The contents of the aforementioned applications are hereby incorporated by reference in their entirety.

SEQUENCE LISTING

The instant application contains a Sequence Listing which has been submitted electronically in XML format and is hereby incorporated by reference in its entirety. Said XML copy, created on Nov. 14, 2022, is named A2186-704710_SL.xml and is 31,479 bytes in size.

BACKGROUND

Clustered Regularly Interspaced Short Palindromic Repeats (CRISPR) and CRISPR-associated (Cas) genes, collectively known as CRISPR-Cas or CRISPR/Cas systems, are adaptive immune systems in archaea and bacteria that defend particular species against foreign genetic elements.

SUMMARY OF THE INVENTION

It is against the above background that the present invention provides certain advantages and advancements over the prior art.

Although this invention disclosed herein is not limited to specific advantages or functionalities, the invention provides a variant polypeptide, and/or a composition comprising a variant polypeptide, wherein the variant polypeptide comprises an alteration relative to a parent polypeptide, wherein the parent polypeptide comprises SEQ ID NO: 3, wherein the variant polypeptide is capable of binding to an RNA guide and a target nucleic acid, and wherein the variant polypeptide or a complex comprising the variant polypeptide exhibits enhanced enzymatic activity, enhanced binding activity, enhanced binding specificity, and/or enhanced stability relative to the parent polypeptide or a complex comprising the parent polypeptide.

In some embodiments, the variant polypeptide of the present invention comprises a polypeptide sequence having 50%, 60%, 65%, 70%, 75%, 80%, 85%, 90%, 91%, 92%, 93%, 94%, 95%, 96%, 97%, 98%, or 99%, but not 100%, identity to SEQ ID NO: 3.

In one aspect, the disclosure provides a variant polypeptide, wherein the variant polypeptide comprises an alteration relative to the amino acid sequence of SEQ ID NO: 3, wherein the alteration comprises a D509R, S511R, I521R, D535G, Q514G, L516R, L516G, E198R, S527R, D509K, D509G, L580G, V359R, D535K, Y381R, R354G, M380K, M380R, V383R, L580R, E367R, I521K, E367G, E507R, I521G, W350R, D535R, R528K, S527K, L385G, W350G, L516K, Y381G, H532R, D129R, P615R, G578R, M380G, V595G, R531G, D129G, R531K, D158G, N476G, G578K, A512R, P618R, V595R, V595K, V383G, A597G, Y381K, P618G, E198K, T288R, E507K, L385R, C538G, P615G, D386R, S511K, C371G, K136G, N220R, S78K, K141G, K240R, D277R, T165R, or K374R wherein the variant polypeptide comprises at least 90% identity to the amino acid sequence of SEQ ID NO: 3.

In one aspect, the disclosure provides variant polypeptide, wherein the variant polypeptide comprises an alteration relative to the amino acid sequence of SEQ ID NO: 3, wherein the alteration comprises a D509R, S511R, I521R, D535G, Q514G, L516R, L516G, E198R, S527R, D509K, D509G, L580G, V359R, D535K, Y381R, R354G, M380K, M380R, V383R, L580R, E367R, I521K, E367G, E507R, I521G, W350R, D535R, R528K, S527K, L385G, W350G, L516K, Y381G, H532R, D129R, P615R, G578R, M380G, V595G, R531G, D129G, R531K, D158G, N476G, G578K, A512R, P618R, V595R, V595K, V383G, A597G, Y381K, P618G, E198K, T288R, E507K, L385R, C538G, P615G, D386R, S511K, or C371G, K136G, N220R, S78K, K141G, K240R, D277R, T165R, or K374R, and wherein the variant polypeptide differs from the amino acid sequence of SEQ ID NO: 3 by 1-20 amino acid residues.

In some embodiments, the variant polypeptide differs from the amino acid sequence of SEQ ID NO: 3 by between 1 and 50 amino acid residue(s) (e.g., between 1 and 45, 1 and 35, 1 and 25, 1 and 15 and 10, and 1 and 5, 5 and 50, 5 and 40, 5 and 30, 5 and 20, 5 and 10, 10 and 50, 10 and 40, 10 and 30, 10 and 20, 10 and 15, 15 and 50, 15 and 40, 15 and 30, 15 and 20, 20 and 50, 20 and 40, 20 and 30, 20 and 35, 25 and 50, 25 and 40, 25 and 30, 30 and 50, 30 and 40, 30 and 35, or 40 and 50 amino acid residue(s)). In some embodiments, the variant polypeptide differs from the amino acid sequence of SEQ ID NO: 3 by 50, 40, 35, 30, 25, 20, 19, 18, 17, 16, 15, 14, 13, 12, 11, 10, 9, 8, 7, 6, 5, 4, 3, 2, or 1 amino acid residue(s).

In some embodiments, the variant polypeptide further comprises a second alteration relative to the amino acid sequence of SEQ ID NO: 3. In certain embodiments,
  i) the alteration comprises L580G and second alteration comprises L385G
  ii) the alteration comprises D509R and the second alteration comprises M380R;
  iii) the alteration comprises L580G and the second alteration comprises A512R;
  iv) the alteration comprises S527R and the second alteration comprises C538G;
  v) the alteration comprises D129R and the second alteration comprises P618R; or
  vi) the alteration comprises Q514G and the second alteration comprises A512R.

In some embodiments, the variant polypeptide further comprises a third alteration relative to the amino acid sequence of SEQ ID NO: 3. In some embodiments,
  i) the alteration comprises D535G, the second alteration comprises L516R, and the third alteration comprises I521R;
  ii) the alteration comprises L516R, the second alteration comprises Q514G, and the third alteration comprises I521R;
  iii) the alteration comprises D509R, the second alteration comprises L516R, and the third alteration comprises I521R;
  iv) the alteration comprises D535G, the second alteration comprises L516R, and the third alteration comprises Q514G;
  v) the alteration comprises D535G, the second alteration comprises Q514G, and the third alteration comprises I521R;
  vi) the alteration comprises K136G, the second alteration comprises N220R, and the third alteration comprises M380R vii) the alteration comprises S78K, the second alteration comprises E198R, and the third alteration comprises R354G;

viii) the alteration comprises K141G, the second alteration comprises N220R, and the third alteration comprises M380R;

ix) the alteration comprises K141G, the second alteration comprises K240R, and the third alteration comprises M380R; and, x) the alteration comprises K141G, the second alteration comprises D277R, and the third alteration comprises M380R.

In some embodiments, the alteration comprises D535G, the second alteration comprises L516R, and the third alteration comprises I521R. In some embodiments, the alteration comprises L516R, the second alteration comprises Q514G, and the third alteration comprises I521R. In some embodiments, the alteration comprises D509R, the second alteration comprises L516R, and the third alteration comprises I521R. In some embodiments, the alteration comprises D535G, the second alteration comprises L516R, and the third alteration comprises Q514G. In some embodiments, the alteration comprises D535G, the second alteration comprises Q514G, and the third alteration comprises I521R. In some embodiments, the alteration comprises D509R, the second alteration comprises D535G, and the third alteration comprises L516R. In some embodiments, the alteration comprises D509R, the second alteration comprises L516R, and the third alteration comprises Q514G. In some embodiments, the alteration comprises D509R, the second alteration comprises Q514G, and the third alteration comprises I521R. In some embodiments, the alteration comprises D509R, the second alteration comprises D535G, and the third alteration comprises I521R. In some embodiments, the alteration comprises D509R, the second alteration comprises D535G, and the third alteration comprises Q514G. In some embodiments, the alteration comprises K136G, the second alteration comprises N220R, and the third alteration comprises M380R. In some embodiments, the alteration comprises S78K, the second alteration comprises E198R, and the third alteration comprises R354G. In some embodiments, the alteration comprises K141G, the second alteration comprises N220R, and the third alteration comprises M380R. In some embodiments, the alteration comprises K141G, the second alteration comprises K240R, and the third alteration comprises M380R. In some embodiments, the alteration comprises K141G, the second alteration comprises D277R, and the third alteration comprises M380R. In some embodiments, the alteration comprises K136G, the second alteration comprises D277R, and the third alteration comprises M380R. In some embodiments, the alteration comprises S78K, the second alteration comprises E198R, and the third alteration comprises L385R. In some embodiments, the alteration comprises S78K, the second alteration comprises E198R, and the third alteration comprises M380R. In some embodiments, the alteration comprises K136G, the second alteration comprises K240R, and the third alteration comprises M380R. In some embodiments, the alteration comprises T165R, the second alteration comprises N220R, and the third alteration comprises M380R. In some embodiments, the alteration comprises S78K, the second alteration comprises E198R, and the third alteration comprises K374R. In some embodiments, the alteration comprises T165R, the second alteration comprises D277R, and the third alteration comprises M380R. In some embodiments, the alteration comprises T165R, the second alteration comprises K240R, and the third alteration comprises M380R. In some embodiments, the alteration comprises K141G, the second alteration comprises K240R, and the third alteration comprises L385R. In some embodiments, the alteration comprises K136G, the second alteration comprises N220R, and the third alteration comprises L385R. In some embodiments, the alteration comprises K141G, the second alteration comprises N220R, and the third alteration comprises L385R. In some embodiments, the alteration comprises K141G, the second alteration comprises D277R, and the third alteration comprises L385R. In some embodiments, the alteration comprises K136G, the second alteration comprises N220R, and the third alteration comprises K374R. In some embodiments, the alteration comprises K136G, the second alteration comprises D277R, and the third alteration comprises L385R. In some embodiments, the alteration comprises K136G, the second alteration comprises K240R, and the third alteration comprises L385R. In some embodiments, the alteration comprises T165R, the second alteration comprises K240R, and the third alteration comprises L385R.

In certain embodiments, the variant polypeptide further comprises a fourth alteration relative to the amino acid of SEQ ID NO: 3. In some embodiments, the alteration comprises Q514G, the second alteration comprises I521R, the third alteration comprises L580G, and the fourth alteration comprises E198R. In some embodiments, the alteration comprises D535G, the second alteration comprises Q514G, the third alteration comprises I521R, and the fourth alteration comprises E198R. In some embodiments, the alteration comprises D535G, the second alteration comprises L516R, the third alteration comprises Q514G, and the fourth alteration comprises I521R. In some embodiments, the alteration comprises Q514G, the second alteration comprises I521R, the third alteration comprises S527R, and the fourth alteration comprises E198R. In some embodiments, the alteration comprises D535G, the second alteration comprises L516R, the third alteration comprises I521R, and the fourth alteration comprises S527R. In some embodiments, the alteration comprises D535G, the second alteration comprises I521R, the third alteration comprises L580G, and the fourth alteration comprises E198R. In some embodiments, the alteration comprises I521R, the second alteration comprises S527R, the third alteration comprises E198R, and the fourth alteration comprises M380R. In some embodiments, the alteration comprises D535G, the second alteration comprises L516R, the third alteration comprises Q514G, and the fourth alteration comprises S511R. In some embodiments, the alteration comprises D535G, the second alteration comprises L516R, the third alteration comprises Q514G, and the fourth alteration comprises S527R. In some embodiments, the alteration comprises I521R, the second alteration comprises S527R, the third alteration comprises L580G, and the fourth alteration comprises E198R. In some embodiments, the alteration comprises D535G, the second alteration comprises L516R, the third alteration comprises S527R, and the fourth alteration comprises M380R. In some embodiments, the alteration comprises Q514G, the second alteration comprises S527R, the third alteration comprises L580G, and the fourth alteration comprises E198R. In some embodiments, the alteration comprises L516R, the second alteration comprises Q514G, the third alteration comprises I521R, and the fourth alteration comprises M380R. In some embodiments, the alteration comprises D509R, the second alteration comprises L516R, the third alteration comprises Q514G, and the fourth alteration comprises S527R. In some embodiments, the alteration comprises D509R, the second alteration comprises I521R, the third alteration comprises L580G, and the fourth alteration comprises E198R. In some embodiments, the alteration comprises S527R, the second alteration comprises L580G, the third alteration comprises E198R, and the fourth alteration comprises M380R. In some embodiments, the alteration comprises L516R, the second alteration comprises S527R, the third alteration comprises L580G, and the fourth alteration comprises E198R. In some embodiments, the alteration comprises D509R, the second alteration comprises Q514G, the third alteration comprises I521R, and the fourth alteration comprises E198R. In some embodiments, the alteration comprises D535G, the second alteration comprises Q514G, the third alteration comprises I521R, and the fourth alteration comprises S527R. In some embodiments, the alteration comprises Q514G, the second alteration comprises L580G, the third alteration comprises E198R, and the fourth alteration comprises M380R. In some embodiments, the alteration comprises D509R, the second alteration comprises L516R, the third alteration comprises I521R, and the fourth alteration comprises E198R. In some embodiments, the alteration comprises L516R, the second alteration comprises Q514G, the third alteration comprises I521R, and the fourth alteration comprises L580G. In some embodiments, the alteration comprises D509R, the second alteration comprises D535G, the third alteration comprises Q514G, and the fourth alteration comprises E198R. In some embodiments, the alteration comprises L516R, the second alteration comprises I521R, the third alteration comprises S527R, and the fourth alteration comprises L580G. In some embodiments, the alteration comprises D535G, the second alteration comprises I521R, the third alteration comprises S527R, and the fourth alteration comprises M380R. In some embodiments, the alteration comprises L516R, the second alteration comprises I521R, the third alteration comprises L580G, and the fourth alteration comprises E198R. In some embodiments, the alteration comprises D535G, the second alteration comprises S527R, the third alteration comprises L580G, and the fourth alteration comprises E198R. In some embodiments, the alteration comprises S527R, the second alteration comprises L580G, the third alteration comprises E198R, and the fourth alteration comprises R354G. In some embodiments, the alteration comprises Q514G, the second alteration comprises I521R, the third alteration comprises S527R, and the fourth alteration comprises L580G. In some embodiments, the alteration comprises D535G, the second alteration comprises Q514G, the third alteration comprises E198R, and the fourth alteration comprises M380R. In some embodiments, the alteration comprises L516R, the second alteration comprises Q514G, the third alteration comprises L580G, and the fourth alteration comprises E198R. In some embodiments, the alteration comprises I521R, the second alteration comprises S527R, the third alteration comprises E198R, and the fourth alteration comprises R354G. In some embodiments, the alteration comprises I521R, the second alteration comprises S527R, the third alteration comprises R354G, and the fourth alteration comprises M380R. In some embodiments, the alteration comprises I521R, the second alteration comprises L580G, the third alteration comprises E198R, and the fourth alteration comprises M380R. In some embodiments, the alteration comprises L516R, the second alteration comprises Q514G, the third alteration comprises S527R, and the fourth alteration comprises L580G. In some embodiments, the alteration comprises D535G, the second alteration comprises Q514G, the third alteration comprises S527R, and the fourth alteration comprises E198R. In some embodiments, the alteration comprises D509R, the second alteration comprises Q514G, the third alteration comprises L580G, and the fourth alteration comprises E198R. In some embodiments, the alteration comprises L580G, the second alteration comprises L385G, the third alteration comprises S511R, and the fourth alteration comprises A512R. In some embodiments, the alteration comprises L580G, the second alteration comprises L385G, the third alteration comprises Q514G, and the fourth alteration comprises A512R. In some embodiments, the alteration comprises D129R, the second alteration comprises P618R, the third alteration comprises S511R, and the fourth alteration comprises A512R. In some embodiments, the alteration comprises L580G, the second alteration comprises L385G, the third alteration comprises G578R, and the fourth alteration comprises D158G. In some embodiments, the alteration comprises D129R, the second alteration comprises P618R, the third alteration comprises R354G, and the fourth alteration comprises A512R. In some embodiments, the alteration comprises D129R, the second alteration comprises P618R, the third alteration comprises Q514G, and the fourth alteration comprises A512R. In some embodiments, the alteration comprises D129R, the second alteration comprises P618R, the third alteration comprises S527R, and the fourth alteration comprises L385G. In some embodiments, the alteration comprises L580G, the second alteration comprises L385G, the third alteration comprises Q514G, and the fourth alteration comprises N476G. In some embodiments, the alteration comprises L580G, the second alteration comprises L385G, the third alteration comprises A512R, and the fourth alteration comprises P618R. In some embodiments, the alteration comprises D129R, the second alteration comprises P618R, the third alteration comprises D158G, and the fourth alteration comprises A512R. In some embodiments, the alteration comprises L580G, the second alteration comprises L385G, the third alteration comprises S527R, and the fourth alteration comprises C538G. In some embodiments, the alteration comprises D129R, the second alteration comprises P618R, the third alteration comprises V359R, and the fourth alteration comprises A512R.

In certain embodiments, the variant polypeptide further comprises a fifth alteration relative to the amino acid of SEQ ID NO: 3. In some embodiments, the alteration comprises D509R, the second alteration comprises D535G, the third alteration comprises L516R, the fourth alteration comprises Q514G, and the fifth alteration comprises I521R.

In certain embodiments, the variant polypeptide further comprises a sixth alteration, and optionally further comprises a seventh, eighth, ninth, and tenth alteration.

In some embodiments, the second alteration comprises a substitution, insertion, or deletion.

In certain embodiments, the third alteration comprises a substitution, insertion, or deletion.

In some embodiments, the fourth alteration comprises a substitution, insertion, or deletion.

In some embodiments, the fifth alteration comprises a substitution, insertion, or deletion.

In some embodiments, the sixth, optionally seventh, optionally eighth, optionally ninth, or optionally tenth alteration each independently comprises a substitution, insertion, or deletion.

In some embodiments, the variant polypeptide comprises an alteration of Table 6. In some embodiments, the variant polypeptide comprises an alteration of Table 7. In some embodiments, the variant polypeptide comprises an alteration of Table 8. In some embodiments, the variant polypeptide comprises an alteration of Table 9. In some embodiments, the variant polypeptide comprises two alterations of any cell of Table 7. In some embodiments, the variant polypeptide comprises a plurality of alterations of any cell of Table 8. In some embodiments, the variant polypeptide comprises a plurality of alterations of any cell of Table 9.

In some embodiments, the variant polypeptide or a complex comprising the variant polypeptide exhibits enhanced enzymatic activity and/or enhanced stability relative to a polypeptide of SEQ ID NO 3.

In some embodiments, the variant polypeptide or a complex comprising the variant polypeptide comprises an enhanced enzymatic activity of at least 1.5-fold, 2-fold, 2.5-fold, or 3-fold relative to a polypeptide of SEQ ID NO: 3, e.g., measured by indel activity, e.g., as described in Examples 9 and 10. In some embodiments, the enhanced enzymatic activity is enhanced nuclease activity.

In some embodiments, the variant polypeptide exhibits enhanced binding activity to the RNA guide relative to the parent polypeptide.

In some embodiments, the variant polypeptide exhibits enhanced binding specificity to the RNA guide relative to the parent polypeptide.

In some embodiments, the variant polypeptide and the RNA guide form a variant binary complex, and the variant binary complex exhibits one or more of the following features:
  (i) enhanced binding activity to the target nucleic acid (e.g., on-target binding activity) relative to a parent binary complex;
  (ii) enhanced binding specificity to the target nucleic acid (e.g., on-target binding specificity) relative to a parent binary complex;
  (iii) enhanced stability relative to a parent binary complex; and/or
  (iv) decreased dissociation from the target nucleic acid, and/or decreased off-target binding to a non-target nucleic acid relative to the parent binary complex.

In some embodiments, the variant polypeptide and the RNA guide form a variant binary complex, and the variant binary complex exhibits enhanced binding activity to the target nucleic acid (e.g., on-target binding activity) relative to a parent binary complex.

In some embodiments, the variant polypeptide and the RNA guide form a variant binary complex, and the variant binary complex exhibits enhanced binding specificity to the target nucleic acid (e.g., on-target binding specificity) relative to a parent binary complex.

In some embodiments, the variant polypeptide and the RNA guide form a variant binary complex, and the variant binary complex exhibits enhanced stability relative to a parent binary complex.

In some embodiments, the variant binary complex and the target nucleic acid form a variant ternary complex, and the variant ternary complex exhibits increased stability relative to a parent ternary complex.

In some embodiments, the variant polypeptide further exhibits enhanced binary complex formation, enhanced protein-RNA interactions, and/or decreased dissociation from the RNA guide relative to the parent polypeptide.

In some embodiments, the variant binary complex further exhibits decreased dissociation from the target nucleic acid, and/or decreased off-target binding to a non-target nucleic acid relative to the parent binary complex.

In some embodiments, the enhanced enzymatic activity, enhanced binding activity, enhanced binding specificity, and/or enhanced stability occur over a range of temperatures, e.g., 20° C. to 65° C.

In some embodiments, the enhanced enzymatic activity, enhanced binding activity, enhanced binding specificity, and/or enhanced stability occur over a range of incubation times.

In some embodiments, the enhanced enzymatic activity, enhanced binding activity, enhanced binding specificity, and/or enhanced stability occur in a buffer having a pH in a range of about 7.3 to about 8.6.

In some embodiments, the enhanced enzymatic activity, enhanced binding activity, enhanced binding specificity, and/or enhanced stability occurs when a Tm value of the variant polypeptide, variant binary complex, or variant ternary complex is at least 8° C. greater than the Tm value of the parent polypeptide, parent binary complex, or parent ternary complex.

In other embodiments, the alteration comprises an amino acid sequence alteration relative to the parent polypeptide having the sequence set forth in SEQ ID NO: 3, wherein the alteration comprises one or more (e.g., one, two, three, four, five, or more) substitutions, insertions, deletions, and/or additions as compared to the parent polypeptide having the sequence set forth in SEQ ID NO:3.

In some embodiments, the alteration comprises an amino acid sequence alteration relative to the parent polypeptide sequence set forth in SEQ ID NO: 3, wherein the alteration comprises one or more of the amino acid substitutions listed in Table 2.

In some embodiments, the alteration comprises an arginine, lysine, glutamine, asparagine, histidine, alanine, or glycine substitution.

In some embodiments, the variant polypeptide comprises a RuvC domain or a split RuvC domain.

In some embodiments, the variant polypeptide comprises one or more catalytic residues (e.g., aspartic acid or glutamic acid). In some embodiments, the one or more catalytic residues comprise D345, E506, and D594.

In some embodiments, the variant polypeptide has reduced nuclease activity or is a nuclease dead polypeptide.

In certain embodiments, the second alteration comprises an insertion of a polypeptide domain, wherein optionally the insertion is at the N-terminus, the C-terminus, or internal to the sequence of SEQ ID NO: 3.

In some embodiments, the variant polypeptide further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

In one aspect, the disclosure provides a system comprising a variant polypeptide described herein or a first nucleic acid encoding the variant polypeptide, and an RNA guide or a second nucleic acid encoding the RNA guide, wherein the RNA guide comprises a direct repeat sequence and a spacer sequence.

In some embodiments, the composition or complex comprising the variant polypeptide further comprises the RNA guide, and the RNA guide comprises a direct repeat sequence and a spacer sequence.

In some embodiments, the direct repeat sequence comprises a nucleotide sequence with at least 90% sequence identity to SEQ ID NO: 4, SEQ ID NO: 5, or SEQ ID NO: 6.

In some embodiments, the direct repeat sequence comprises a nucleotide sequence with at least 95% sequence identity to SEQ ID NO: 4, SEQ ID NO: 5, or SEQ ID NO: 6.

In some embodiments, the direct repeat sequence comprises the nucleotide sequence of SEQ ID NO: 4, SEQ ID NO: 5, or SEQ ID NO: 6.

In some embodiments, the spacer sequence comprises between 15 and 35 nucleotides in length.

In certain embodiments, the first nucleic acid is located in a first vector, and the second nucleic acid encoding the RNA guide is located in a vector (e.g., the first vector or a second vector), optionally wherein the first and/or the second vector is a viral vector.

In some embodiments, the RNA guide comprises any one of SEQ ID NOs: 9, 11, 13, 15, 17, 19, 21, and 23.

In some embodiments, the target nucleic acid comprises a sequence complementary to a nucleotide sequence in the spacer sequence.

In some embodiments, the target nucleic acid is adjacent to a protospacer adjacent motif (PAM) sequence, wherein the PAM sequence comprises a nucleotide sequence set forth as 5'-NTN-3', 5'-HTN-3', or 5'-TNA-3', wherein N is any nucleotide and His A or C or T. In some embodiments, the PAM sequence comprises a nucleotide sequence set forth as 5'-CTG-3' or 5'-CTC-3'.

In some embodiments, the target nucleic acid is single-stranded DNA or double-stranded DNA. In some embodiments, the target nucleic acid is a double-stranded DNA.

In one aspect, the present disclosure provides a nucleic acid encoding the variant polypeptide described herein.

In some embodiments, the nucleic acid encoding the variant polypeptide is codon-optimized for expression in a cell.

In certain embodiments, the nucleic encoding further comprises a sequence encoding the guide RNA.

In some embodiments, the nucleic acid encoding the variant polypeptide is operably linked to a promoter.

In certain embodiments, the nucleic acid comprises an RNA (e.g., an mRNA).

In some embodiments, the nucleic acid encoding the variant polypeptide is in a vector.

In some embodiments, the vector comprises a retroviral vector, a lentiviral vector, a phage vector, an adenoviral vector, an adeno-associated vector, or a herpes simplex vector.

In certain embodiments, the viral vector is an adeno-associated viral (AAV) vector.

In one aspect, the disclosure provides a composition comprising the variant polypeptide, the system, the nucleic acid, or the vector described herein. In some embodiments, the composition is present in a delivery composition comprising a nanoparticle, a liposome, an exosome, a microvesicle, or a gene-gun.

In one aspect, the disclosure provides a cell comprising the variant polypeptide, the system, the nucleic acid, or the vector described herein.

In some embodiments, the cell comprises the variant polypeptide and/or the composition disclosed herein.

In some embodiments, the cell is a eukaryotic cell or a prokaryotic cell. In some embodiments, the cell is a eukaryotic cell. In some embodiments, the cell is a mammalian cell or a plant cell. In some embodiments, the cell is a human cell.

The disclosure further provides a method of preparing the variant polypeptide disclosed herein, the method comprising (i) introducing one or more nucleotide substitutions into a nucleic acid comprising SEQ ID NO: 1 or SEQ ID NO: 2 to produce a variant nucleic acid which encodes the variant polypeptide, and (ii) expressing the variant polypeptide from the variant nucleic acid.

The disclosure further provides a method of forming the variant binary complex disclosed herein, the method comprising contacting the variant polypeptide disclosed herein with the RNA guide disclosed herein.

In one aspect, the disclosure provides a method of producing the variant polypeptide, the method comprising (i) producing a nucleic acid sequence encoding the variant polypeptide, and (ii) introducing the nucleic acid sequence into an appropriate host cell capable of expressing the nucleic acid sequence, and (iii) allowing the host cell to express the variant polypeptide.

In one aspect, the disclosure provides a method of producing the variant polypeptide, the method comprising (i) introducing one or more nucleotide substitutions into a nucleic acid comprising SEQ ID NO: 1 or SEQ ID NO: 2 to produce a variant nucleic acid which encodes the variant polypeptide, and (ii) expressing the variant polypeptide from the variant nucleic acid.

The disclosure further provides a method of forming the variant ternary complex, the method comprising contacting the variant polypeptide disclosed herein with the RNA guide disclosed herein and the target nucleic acid disclosed herein.

In one aspect, the disclosure provides a method of delivering the variant polypeptide to a cell, the method comprising introducing into the cell the variant polypeptide described herein or a nucleic acid encoding the variant polypeptide, and optionally, introducing an RNA guide or the nucleic acid encoding the RNA guide, wherein the introducing optionally comprises introducing a nanoparticle, a liposome, an exosome, a microvesicle, a viral vector, or any combination thereof.

In one aspect, the disclosure provides a method for modifying a target DNA molecule in a cell, the method comprising introducing into the cell the variant polypeptide described herein or a nucleic acid encoding the variant polypeptide, and introducing an RNA guide or the nucleic acid encoding the RNA guide, wherein the introducing optionally comprises introducing a nanoparticle, a liposome, an exosome, a microvesicle, a viral vector, or any combination thereof. In some embodiments the step of introducing into the cell comprises transfecting or transducing the cell. In certain embodiments, the step of introducing into the cell comprises use of electroporation, injection, a gene gun, or any combination thereof. In some embodiments, the nucleic acid encoding the variant polypeptide comprises an RNA (e.g., an mRNA).

In one aspect, the disclosure provides a method for modifying a target DNA molecule, the method comprising contacting the target DNA molecule with the variant polypeptide and an RNA guide. In some embodiments, the target DNA molecule is in vitro or in a cell. In certain embodiments, the cell is in vitro, ex vivo, or in vivo. In some embodiments, the cell is selected from a prokaryotic cell, a eukaryotic cell, a plant cell, a mammalian cell, and a human cell.

The disclosure further provides a method of delivering the variant polypeptide or the composition or the variant binary complex disclosed herein, the method comprising introducing into the cell the variant polypeptide or a nucleic acid encoding the variant polypeptide, and optionally, introducing the RNA guide or a nucleic acid encoding the RNA guide described herein, or introducing the variant binary complex described herein, wherein the introducing comprises introducing a nanoparticle, a liposome, an exosome, a microvesicle, a viral vector, or any combination thereof. In some embodiments, the step of introducing into the cell comprises transfecting or transducing the cell. In some embodiments, the step of introducing comprises use of electroporation, injection, a gene gun, or any combination thereof.

The disclosure yet further provides a composition comprising a variant polypeptide, or a complex comprising the variant polypeptide and an RNA guide, wherein the variant polypeptide comprises an alteration relative to a parent polypeptide, wherein the parent polypeptide comprises SEQ ID NO: 3, wherein the variant polypeptide is capable of binding to the RNA guide and a target nucleic acid, and wherein the variant polypeptide or the complex exhibits enhanced enzymatic activity, enhanced binding activity, enhanced binding specificity, and/or enhanced stability relative to the parent polypeptide or a complex comprising the parent polypeptide and the RNA guide.

In some embodiments, the enhanced enzymatic activity is enhanced nuclease activity.

In some embodiments, the variant polypeptide exhibits enhanced binding activity to the RNA guide relative to the parent polypeptide.

In some embodiments, the variant polypeptide exhibits enhanced binding specificity to the RNA guide relative to the parent polypeptide.

In some embodiments, the variant polypeptide and the RNA guide form a variant binary complex, and the variant binary complex exhibits enhanced binding activity to the target nucleic acid (e.g., on-target binding activity) relative to a parent binary complex.

In some embodiments, the variant polypeptide and the RNA guide form a variant binary complex, and the variant binary complex exhibits enhanced binding specificity to the target nucleic acid (e.g., on-target binding specificity) relative to a parent binary complex.

In some embodiments, the variant polypeptide and the RNA guide form a variant binary complex, and the variant binary complex exhibits enhanced stability relative to a parent binary complex.

In some embodiments, the variant binary complex and the target nucleic acid form a variant ternary complex, and the variant ternary complex exhibits increased stability relative to a parent ternary complex.

In some embodiments, the variant polypeptide further exhibits enhanced binary complex formation, enhanced protein-RNA interactions, and/or decreased dissociation from the RNA guide relative to the parent polypeptide.

In some embodiments, the variant binary complex further exhibits decreased dissociation from the target nucleic acid, and/or decreased off-target binding to a non-target nucleic acid relative to the parent binary complex.

In some embodiments, the enhanced enzymatic activity, enhanced binding activity, enhanced binding specificity, and/or enhanced stability occur over a range of temperatures, e.g., 20° C. to 65° C.

In some embodiments, the enhanced enzymatic activity, enhanced binding activity, enhanced binding specificity, and/or enhanced stability occur over a range of incubation times.

In some embodiments, the enhanced enzymatic activity, enhanced binding activity, enhanced binding specificity, and/or enhanced stability occur in a buffer having a pH in a range of about 7.3 to about 8.6.

In some embodiments, the enhanced enzymatic activity, enhanced binding activity, enhanced binding specificity, and/or enhanced stability occurs when a Tm value of the variant polypeptide, variant binary complex, or variant ternary complex is at least 8° C. greater than the Tm value of the parent polypeptide, parent binary complex, or parent ternary complex.

In other embodiments, the alteration comprises an amino acid sequence alteration relative to the parent polypeptide having the sequence set forth in SEQ ID NO: 3, wherein the alteration comprises one or more (e.g., one, two, three, four, five, or more) substitutions, insertions, deletions, and/or additions as compared to the parent polypeptide having the sequence set forth in SEQ ID NO: 3.

In some embodiments, the alteration comprises an amino acid sequence alteration relative to the parent polypeptide sequence set forth in SEQ ID NO: 3, wherein the alteration comprises one or more of the amino acid substitutions listed in Table 2.

In some embodiments, the alteration comprises an arginine, lysine, glutamine, asparagine, histidine, alanine, or glycine substitution.

In some embodiments, the alteration comprises an E38R, T60R, D89R, S223R, P353G, L354G, L360G, K368G, E566R, and/or D730R substitution.

In some embodiments, the variant polypeptide comprises a RuvC domain or a split RuvC domain.

In some embodiments, the variant polypeptide comprises one or more catalytic residues (e.g., aspartic acid or glutamic acid). In some embodiments, the one or more catalytic residues comprise D345, E506, and D594.

In some embodiments, the RNA guide comprises a direct repeat sequence and a spacer sequence.

In some embodiments, the direct repeat sequence comprises a nucleotide sequence with at least 90% sequence identity to SEQ ID NO: 4, SEQ ID NO: 5, or SEQ ID NO: 6.

In some embodiments, the direct repeat sequence comprises a nucleotide sequence with at least 95% sequence identity to SEQ ID NO: 4, SEQ ID NO: 5, or SEQ ID NO: 6.

In some embodiments, the direct repeat sequence comprises the nucleotide sequence of SEQ ID NO: 4, SEQ ID NO: 5, or SEQ ID NO: 6.

In some embodiments, the spacer sequence comprises between 15 and 35 nucleotides in length.

In some embodiments, the target nucleic acid comprises a sequence complementary to a nucleotide sequence in the spacer sequence.

In some embodiments, the target nucleic acid is adjacent to a PAM sequence, wherein the PAM sequence comprises a nucleotide sequence set forth as 5'-NTN-3', 5'-HTN-3', or 5'-TNA-3', wherein N is any nucleotide and His A or C or T. In some embodiments, the PAM sequence comprises a nucleotide sequence set forth as 5'-CTG-3' or 5'-CTC-3'.

In some embodiments, the target nucleic acid is single-stranded DNA or double-stranded DNA.

In some embodiments, the variant polypeptide further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

In some embodiments, a nucleic acid encoding the variant polypeptide is codon-optimized for expression in a cell In some embodiments, the nucleic acid encoding the variant polypeptide is operably linked to a promoter.

In some embodiments, the nucleic acid encoding the variant polypeptide is in a vector.

In some embodiments, the vector comprises a retroviral vector, a lentiviral vector, a phage vector, an adenoviral vector, an adeno-associated vector, or a herpes simplex vector.

In some embodiments, the composition or complex is present in a delivery composition comprising a nanoparticle, a liposome, an exosome, a microvesicle, or a gene-gun.

The disclosure further provides an RNA guide or a nucleic acid encoding the RNA guide comprising a direct repeat sequence comprising at least 90% identity to any one of SEQ ID NOs: 4, 5 or 6. In some embodiments, the RNA guide or nucleic acid encoding the RNA guide comprises a spacer sequence that binds adjacent to a 5'-CTG-3' or 5'-CTC-3' protospacer adjacent motif. In some embodiments, the RNA guide that comprises a nucleotide sequence with at least 90% sequence identity to any of SEQ ID NO: 4-6 binds a CRISPR nuclease, e.g., a CRISPR nuclease according to SEQ ID NO: 3.

The disclosure further provides a composition comprising the RNA guide, wherein the composition further comprises a CRISPR nuclease. In some embodiments, the CRISPR nuclease comprises at least 80% identity (e.g., at least 80%, 81%, 82%, 83%, 84%, 85%, 86%, 87%, 88%, 89%, 90%, 91%, 92%, 93%, 94%, 95%, 96%, 97%, 98%, 99%, or 100% identity) to SEQ ID NO: 3. In some embodiments, the CRISPR nuclease comprises at least 95% identity (e.g., at least 95%, 96%, 97%, 98%, 99%, or 100% identity) to SEQ ID NO: 3. In some embodiments, the CRISPR nuclease comprises SEQ ID NO: 3.

The disclosure further provides a cell comprising the variant polypeptide and/or the complex disclosed herein. In some embodiments, the cell is a eukaryotic cell or a prokaryotic cell. In some embodiments, the cell is a mammalian cell or a plant cell. In some embodiments, the cell is a human cell.

The disclosure further provides a method of preparing the variant polypeptide disclosed herein, the method comprising (i) introducing one or more nucleotide substitutions into a nucleic acid comprising SEQ ID NO: 1 or SEQ ID NO: 2 to produce a variant nucleic acid which encodes the variant polypeptide, and (ii) expressing the variant polypeptide from the variant nucleic acid.

The disclosure further provides a method of forming the variant binary complex, the method comprising contacting the variant polypeptide disclosed herein with the RNA guide disclosed herein.

The disclosure further provides a method of forming the variant ternary complex, the method comprising contacting the variant polypeptide disclosed herein with the RNA guide disclosed herein and the target nucleic acid disclosed herein.

The disclosure further provides a method of delivering the variant polypeptide or the composition or the variant binary complex disclosed herein to a cell, the method comprising introducing into the cell the variant polypeptide disclosed herein or a nucleic acid encoding the variant polypeptide, and optionally, introducing the RNA guide or a nucleic acid encoding the RNA guide described herein, or introducing the variant binary complex described herein, wherein the introducing comprises introducing a nanoparticle, a liposome, an exosome, a microvesicle, a viral vector, or any combination thereof. In some embodiments, the step of introducing into the cell comprises transfecting or transducing the cell. In some embodiments, the step of introducing comprises use of electroporation, injection, a gene gun, or any combination thereof. In some embodiments, the cell is selected from a prokaryotic cell, a eukaryotic cell, a plant cell, a mammalian cell, and a human cell. In some embodiments, the cell is in vitro, ex vivo, or in vivo.

The disclosure further provides a method for modifying a target DNA molecule in a cell, the method comprising introducing into the cell the variant polypeptide disclosed herein or a nucleic acid encoding the variant polypeptide, and introducing the RNA guide or a nucleic acid encoding the RNA guide described herein, or introducing the variant binary complex described herein, wherein the introducing comprises introducing a nanoparticle, a liposome, an exosome, a microvesicle, a viral vector, or any combination thereof. In some embodiments, the step of introducing into the cell comprises transfecting or transducing the cell. In some embodiments, the step of introducing comprises use of electroporation, injection, a gene gun, or any combination thereof. In some embodiments, the cell is selected from a prokaryotic cell, a eukaryotic cell, a plant cell, a mammalian cell, and a human cell. In some embodiments, the cell is in vitro, ex vivo, or in vivo.

The disclosure further provides a method for modifying a target DNA molecule, the method comprising contacting the target DNA molecule with the variant polypeptide disclosed herein and the RNA guide disclosed herein. In some embodiments, the target DNA molecule is in vitro or in a cell. In some embodiments, the cell is in vitro, ex vivo, or in vivo. In some embodiments, the cell is selected from a prokaryotic cell, a eukaryotic cell, a plant cell, a mammalian cell, and a human cell.

In some aspects, the disclosure provides a method of modifying a target nucleic acid in a cell, wherein the method comprising (i) introducing into the cell a polypeptide comprising an amino acid sequence according to SEQ ID NO: 3, or a sequence having at least 70%, 75%, 80%, 85%, 90%, 91%, 92%, 93%, 94%, 95%, 96%, 97%, 98%, or 99% identity thereto, or a nucleic acid encoding the polypeptide, and (ii) introducing an RNA guide (e.g., as described herein) or a nucleic acid encoding the RNA guide into the cell, wherein target nucleic acid is adjacent to a protospacer adjacent motif (PAM) sequence, wherein the PAM sequence comprises a nucleotide sequence set forth as 5'-CTG-3' or 5'-CTC-3'. In some embodiments, the polypeptide comprises an amino acid sequence according to of any one of SEQ ID NOs: 3-7. The introducing optionally comprises introducing a nanoparticle, a liposome, an exosome, a microvesicle, a viral vector, or any combination thereof. In some embodiments the step of introducing into the cell comprises transfecting or transducing the cell. In certain embodiments, the step of introducing into the cell comprises use of electroporation, injection, a gene gun, or any combination thereof. In some embodiments, the nucleic acid encoding the polypeptide comprises an RNA (e.g., an mRNA). In some embodiments, the method modifies the target DNA at a position adjacent to the 5'-CTG-3' or 5'-CTC-3' protospacer adjacent motif. In some embodiments, the modifying comprises nicking or cleaving the target nucleic acid.

In some aspects, the present disclosure provides an RNA guide or a nucleic acid encoding the RNA guide, wherein the RNA guide comprises a direct repeat sequence and a spacer sequence, and wherein the direct repeat sequence comprises a nucleotide sequence of any one of SEQ ID NOs: 4-6, or a sequence having at least 90%, 91%, 92%, 93%, 94%, 95%, 96%, 97%, 98%, or 99% identity thereto, wherein the nucleotide immediately 3' of the direct repeat sequence is chosen from C, T, or G. In some aspects, the present disclosure provides an RNA guide or a nucleic acid encoding the RNA guide, wherein the RNA guide comprises a direct repeat sequence and a spacer sequence, and wherein the direct repeat sequence comprises a nucleotide sequence of any one of SEQ ID NOs: 4-6, or a sequence having at least 90%, 91%, 92%, 93%, 94%, 95%, 96%, 97%, 98%, or 99% identity thereto, wherein the nucleotide immediately 3' of the direct repeat sequence is other than A. In some aspects, the present disclosure provides an RNA guide or a nucleic acid encoding the RNA guide, wherein the RNA guide comprises a direct repeat sequence and a spacer sequence, and wherein the direct repeat sequence comprises a nucleotide sequence of SEQ ID NO: 5 or 6, or a sequence having at least 90%, 91%, 92%, 93%, 94%, 95%, 96%, 97%, 98%, or 99% identity thereto. In some aspects, the present disclosure provides an RNA guide or a nucleic acid encoding the RNA guide, wherein the RNA guide comprises a direct repeat sequence and a spacer sequence, and wherein the direct repeat sequence consists of a nucleotide sequence of any one of SEQ ID NOs: 4-6, or a sequence with 1, 2, 3, or 4 substitutions thereto. In some embodiments, the spacer is heterologous to the direct repeat sequence.

BRIEF DESCRIPTION OF THE DRAWINGS

FIG. 1 shows the indel activity (% raw indels) across eight target sites adjacent to a 5'-CTG-3' PAM sequence. The sequences for the target sites and crRNAs are shown in Table 4.

DETAILED DESCRIPTION

Definitions

The present invention will be described with respect to particular embodiments and with reference to certain Figures, but the invention is not limited thereto but only by the claims. Terms as set forth hereinafter are generally to be understood in their common sense unless indicated otherwise.

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics, and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients. That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of +20% or +10%, more preferably +5%, even more preferably +1%, and still more preferably +0.1% from the specified value, as such variations are appropriate to perform the disclosed methods.

As used herein, the term "complex" refers to a grouping of two or more molecules. In some embodiments, the complex comprises a polypeptide and a nucleic acid molecule interacting with (e.g. binding to, coming into contact with, adhering to) one another.

As used herein, the term "binary complex" refers to a grouping of two molecules (e.g., a polypeptide and a nucleic acid molecule). In some embodiments, a binary complex refers to a grouping of a polypeptide and a targeting moiety (e.g., an RNA guide). In some embodiments, a binary complex refers to a ribonucleoprotein (RNP). As used herein, the term "variant binary complex" refers to the grouping of a variant polypeptide and RNA guide. As used herein, the term "parent binary complex" refers to the grouping of a parent polypeptide and RNA guide or a reference polypeptide and RNA guide.

As used herein, the term "ternary complex" refers to a grouping of three molecules (e.g., a polypeptide and two nucleic acid molecules). In some embodiments, a "ternary complex" refers to a grouping of a polypeptide, an RNA molecule, and a DNA molecule. In some embodiments, a ternary complex refers to a grouping of a polypeptide, a targeting moiety (e.g., an RNA guide), and a target nucleic acid (e.g., a target DNA molecule). In some embodiments, a "ternary complex" refers to a grouping of a binary complex (e.g., a ribonucleoprotein) and a third molecule (e.g., a target nucleic acid).

As used herein, the term "domain" refers to a distinct functional and/or structural unit of a polypeptide. In some embodiments, a domain may comprise a conserved amino acid sequence.

As used herein, the terms "parent," "parent polypeptide," and "parent sequence" refer to an original polypeptide (e.g., reference or starting polypeptide) to which an alteration is made to produce a variant polypeptide of the present invention.

As used herein, the term "protospacer adjacent motif" or "PAM" refers to a DNA sequence adjacent to a target sequence to which a complex comprising an effector (e.g., a CRISPR nuclease) and an RNA guide binds. In some embodiments, a PAM is required for enzyme activity. As used herein, the term "adjacent" includes instances in which an RNA guide of the complex specifically binds, interacts, or associates with a target sequence that is immediately adjacent to a PAM. In such instances, there are no nucleotides between the target sequence and the PAM. The term "adjacent" also includes instances in which there are a small number (e.g., 1, 2, 3, 4, or 5) of nucleotides between the target sequence, to which the RNA guide binds, and the PAM. In a double-stranded DNA molecule, the strand containing the PAM motif is called the "PAM-strand" and the complementary strand is called the "non-PAM strand." The RNA guide binds to a site in the non-PAM strand that is complementary to a target sequence disclosed herein. In some embodiments, the PAM strand is a coding (e.g., sense) strand. In other embodiments, the PAM strand is a non-coding (e.g., antisense strand). Since an RNA guide binds the non-PAM strand via base-pairing, the non-PAM strand is also known as the target strand (TS), while the PAM strand is also known as the non-target strand (NTS).

As used herein, the terms "reference composition," "reference molecule," "reference sequence," and "reference" refer to a control, such as a negative control or a parent (e.g., a parent sequence, a parent protein, or a wild-type protein). For example, a reference molecule refers to a polypeptide to which a variant polypeptide is compared. Likewise, a reference RNA guide refers to a targeting moiety to which a modified RNA guide is compared. The variant or modified molecule may be compared to the reference molecule on the basis of sequence (e.g., the variant or modified molecule may have X % sequence identity or homology with the reference molecule), thermostability, or activity (e.g., the variant or modified molecule may have X % of the activity of the reference molecule). For example, a variant or modified molecule may be characterized as having no more than 10% of an activity of the reference polypeptide or may be characterized as having at least 10% greater of an activity of the reference polypeptide. Examples of reference polypeptides include naturally occurring unmodified polypeptides, e.g., naturally occurring polypeptides from archaea or bacterial species. In certain embodiments, the reference polypeptide is a naturally occurring polypeptide having the closest sequence identity or homology with the variant polypeptide to which it is being compared. In certain embodiments, the reference polypeptide is a parental molecule having a naturally occurring or known sequence on which a mutation has been made to arrive at the variant polypeptide.

As used herein, the terms "RNA guide" or "RNA guide sequence" refer to any RNA molecule that facilitates the targeting of a polypeptide described herein to a target nucleic acid. For example, an RNA guide can be a molecule that recognizes (e.g., binds to) a target nucleic acid. An RNA guide may be designed to be complementary to a specific nucleic acid sequence. An RNA guide comprises a DNA targeting sequence (also referred to herein as a spacer sequence), and a direct repeat (DR) sequence that facilitates binding of the RNA guide to a polypeptide of the invention. The terms CRISPR RNA (crRNA), pre-crRNA and mature crRNA are also used herein to refer to an RNA guide. In some instances, the RNA guide can be a modified RNA molecule comprising one or more deoxyribonucleotides, for example, in a DNA-binding sequence contained in the RNA guide, which binds the non-PAM strand of a target nucleic acid. In some examples, the DNA-binding sequence may contain a DNA sequence or a DNA/RNA hybrid sequence.

As used herein, the term "substantially identical" refers to a sequence, polynucleotide, or polypeptide, that has a certain degree of identity to a reference sequence.

As used herein, the terms "target nucleic acid," "target sequence," and "target substrate" refer to a nucleic acid to which an RNA guide specifically binds. In some embodiments, the DNA targeting sequence (i.e., a spacer sequence) of an RNA guide binds to a target nucleic acid. In some embodiments, the target sequence is a segment of DNA adjacent to a PAM motif (on the PAM strand). The complementary region of the target sequence is on the non-PAM strand. A target sequence may be immediately adjacent to the PAM motif. Alternatively, the target sequence and the PAM may be separated by a small sequence segment (e.g., up to 5 nucleotides, for example, up to 4, 3, 2, or 1 nucleotide). A target sequence may be located at the 3' end of the PAM motif or at the 5' end of the PAM motif, depending upon the CRISPR nuclease that recognizes the PAM motif, which is known in the art. For example, a target sequence is located at the 3' end of a PAM motif for a Cas12i polypeptide (e.g., a Cas 12i2 polypeptide such as those disclosed herein). It is of course understood that DNA is often double stranded, and that a RNA guide will bind to one of the two strands, to which it is complementary. The location in the DNA where the RNA guide binds can be conveniently described by either providing the sequence of the strand to which the RNA guide binds (the non-PAM strand) or the sequence of the strand to which the RNA guide does not bind (the PAM strand). Thus, as is clear from context throughout the application, a target nucleic acid sequence may be described by providing the nucleic acid sequence of either strand of the double stranded DNA targeted by a RNA guide described herein.

As used herein, the terms "variant polypeptide", "variant effector polypeptide," and "variant CRISPR nuclease polypeptide" refer to a polypeptide comprising an alteration, e.g., but not limited to, a substitution, insertion, deletion, addition and/or fusion, at one or more residue positions, compared to a parent polypeptide. The positions of identified alterations provided herein, unless specified otherwise, are numbered relative to SEQ ID NO: 3. For example, an alteration of D509R indicates an alteration of the 509th amino acid relative to SEQ ID NO: 3 even if the variant polypeptide comprises a fusion or a truncation at the N-terminus, C-terminus, or internally, e.g., such that the alteration is not at position 509 relative to the N-terminus in the fusion polypeptide or truncated polypeptide. Amino acid positions of SEQ ID NO: 3 are further described in Table 2. As used herein, the terms "variant polypeptide", "variant effector polypeptide," and "variant CRISPR nuclease polypeptide" refer to a polypeptide comprising an alteration as compared to the polypeptide of SEQ ID NO: 3.

Compositions

In some aspects, the present invention provides novel variants of the effector (e.g., the CRISPR nuclease) of SEQ ID NO: 3, compositions comprising the variants, and methods of preparation and use thereof. In other aspects, the present invention further provides complexes comprising a variant of the effector (e.g., the CRISPR nuclease) of SEQ ID NO: 3 and compositions, methods of preparation and use thereof. In some aspects, a composition comprising a complex having one or more characteristics is described herein. In some aspects, a method of delivering a composition comprising the complex is described.

In some embodiments, a composition of the disclosure includes a variant polypeptide that exhibits enhanced enzymatic activity, enhanced binding activity, enhanced binding specificity, and/or enhanced stability relative to a parent polypeptide. In some embodiments, a composition of the disclosure includes a complex comprising a variant polypeptide that exhibits enhanced enzymatic activity, enhanced binding activity, enhanced binding specificity, and/or enhanced stability relative to a parent complex. In some embodiments, the variant polypeptide comprises an alteration relative to a parent polypeptide, wherein the parent polypeptide comprises SEQ ID NO: 3, and wherein the variant polypeptide is capable of binding to an RNA guide and a target nucleic acid.

In some embodiments, a composition of the disclosure includes a variant polypeptide and an RNA guide. In some embodiments, a composition of the disclosure includes a variant binary complex comprising a variant polypeptide and an RNA guide.

In some embodiments of the composition, the variant polypeptide has increased complex formation (e.g., increased binary complex formation) with the RNA guide as compared to a parent polypeptide. In some embodiments of the composition, the variant polypeptide and the RNA guide have a greater binding affinity, as compared to a parent polypeptide and the RNA guide. In some embodiments of the composition, the variant polypeptide and the RNA guide have stronger protein-RNA interactions (e.g., ionic interactions), as compared to a parent polypeptide and the RNA guide. In some embodiments of the composition, the variant binary complex is more stable than a parent binary complex.

In some embodiments, a composition of the disclosure includes a variant polypeptide, an RNA guide, and a target nucleic acid. In some embodiments, a composition of the disclosure includes a variant ternary complex comprising a variant polypeptide, an RNA guide, and a target nucleic acid.

In some embodiments of the composition, the variant polypeptide has increased complex formation (e.g., increased ternary complex formation) with the RNA guide and target nucleic acid as compared to a parent polypeptide. In some embodiments of the composition, the variant polypeptide and the RNA guide (e.g., the variant binary complex) have a greater binding affinity to a target nucleic acid, as compared to a parent polypeptide and the RNA guide (e.g., a parent binary complex). In some embodiments of the composition, the variant ternary complex is more stable than a parent ternary complex.

In some embodiments, the composition of the present disclosure includes a variant polypeptide described herein.

Variant Polypeptide

In one embodiment, the variant polypeptide (e.g., variant CRISPR nuclease polypeptide) is an isolated or purified polypeptide.

In some embodiments, the variant polypeptide of the present disclosure is a variant of a parent polypeptide (e.g., a parent CRISPR nuclease), wherein the parent is encoded by a polynucleotide that comprises a nucleotide sequence such as SEQ ID NO: 1 or SEQ ID NO: 2 or comprises an amino acid sequence such as SEQ ID NO: 3. See Table 1.

TABLE 1

Sequences corresponding to SEQ ID NOs: 1-3.

| Sequence Identifier | Sequence |
|---|---|
| SEQ ID NO: 1 | ATGGGTGCGGCTCGTCGCCGTAACCCGAAGGTTGCAGCGGCGCGTAA<br>GGGCAAGCCGCCGCCGAAAGCAACCGGTAACTGCCGTAATTACCGCT<br>ATGGTGCGCACGAACCGATCGCGAATCTGGACAAGGTGCTGGACGA<br>GATGCGTGGCGCGCATGACCTGCGCAACGTTTTGACCTGTATCAATC<br>GTGCGCGCTCCGAGATGATTACGGCTGCACTGGGTGAACACCAGTCT<br>TACAAGAAGGCGACCGCAGACCTGGCCGGCATTGCATCAGCGCCGTGA<br>TAAGCTGGAAGCGCAAATCCGTCAGCAGAACAGCGCGAGCCGTAAA<br>CGTCTGGGTCGTCACAGCCCGCTGAGCAGCGAGCTGGACACCGTTCG<br>TAAGCGCATTGATGAGGGTCGTACGGCGCTGAAGAAGCTGCGCCGTA<br>AGCTGCTGAAGAAGGACCCGGCCCTGAAAGCGGTGGTTGAGGCTGC<br>AGACGATATGGCGAAACGTGAAACCACCCGTGCGGAAGATGCATGC<br>GGCCTGTATTGGTGTACCCGTAACGAACAGACGGGCAAGCGTGCGAA<br>ACTGCGCCGTTTCAAGAAATGGCGTGACAGCGAGGCGACCATCAGCG<br>TGCAAATTCCGGGTGGCCTGACCGTTGAGCAGCTGCTGGGTGGTGAG<br>AACAATCAAGCACGTCTGGAGCTGCGTCCGGAAGGCGTGTGGGTTCA<br>GGGTGCGCGTAAACGTAAAGTGGAACCGGCAGAAGCGGCACGTAAC<br>AAGCTGCGTCTGGACGAAGATGGCTACCCGATGCGTAAACTGGGCAC<br>CGCGATTCTGCACCTGCGTTGCATGAGCGACGAGGATGGCAAGCCGA<br>TCTGGGCGGAAGTTCCGATTACCTATCATCGTGAGATCCCGGCTGAT<br>GCAAAGATTAAACGTTGTTACCTGCACCGTTTCCGCGTGGGTAATCGT<br>TATCATTGGTCCGTTCGTTTTAGCCTGGAGCGCGGTAAGAAAGGCGA<br>CGATAGCTGGCTGCACCCGCGTGTGGCAACCACCGGCACCGCTGCAA<br>TCGACATTGGTTGGCGTTGGTTTCCGGATCGTCTGCGTGTTGCGGTGT<br>GGGCAGGTAGCGACGGCGCGGAGGGTGAACTGTGCTTGCCGAAATG<br>GTGGCTGGATGAAATGTACAGCGTGCGTCTGGACCAGCGTGAGCGCG<br>ATGTTCTGTTCAACGAAATCGTGAGCCTGGTTTTGCCGTGGTTTCGTA<br>GCCGTCGTGGTGAGCTGTCTGACTATGTCGTGCAAGCGATTAAGACC<br>ATGCATTCTTGGCGTGATAAAGGCCGCCTGGCCGGCATTGAGCATGCG<br>TTGGCGTGATGATCTGGCTGCGGACCCGGGTGCTAACCCGGCACATG<br>TGGCCATGAGCATCCGTCGGAGGAATGGCGTAAGCGCGACAAACAT<br>ATTTGGTGCGAGGAAGTTAACCTGCGTAGCCAGTTGCAAGGCAGCCG<br>TAAGGATCTGTATCGCCGTTTCGCGGCAATGCTGACCAGCCGTTATG<br>GTCGCATCGTTGTCGAGGAATTTGATCTGAGCGCAGTGCAGAAGCTG<br>CCGCCGGCTAGCATTGACGATGGCACCTACAGCCGTGTGAAGCGCCA<br>CAAAGGTGATGCTGCATGCAGCCATCTGGTTGGTGCGCTGAAGGACG<br>CCGCGCGTCAACTGGATAAGAAAAACCCGAAGTGGACCACGAAACG<br>TTGCCACGTTTGTGGCAAGACCGAGCGTAAATGGGAAAATCCGGGCG<br>AGCTGGAACACACCTGCAAACATTGTGGTGTCCTGTGGGACCGTGAT<br>GTGAACGCTGCACGCAATATCCTGGCCGCGAGCGGCGTTGCGGTTGA<br>CTGGACCCGTCCGCCGCTGGCACCGGCTGCACGTATGACCTATCCGC<br>AGGTTGAGAACCGTGAAATGCGCCGTAGCCGCCGTCGCAAAGAGGC<br>GCTGGAAACCACCCGTGCGTCCGGTGATCGCCAAACCGCG |
| SEQ ID NO: 2 | ATGGGCGCCGCTCGGAGAAGGAACCCTAAGGTGGCAGCAGCTCGTA<br>AGGGCAAGCCACCTCCAAAAGCCACCGGCAACTGCCGGAATTACAG<br>ATATGGGCACACGAACCAATCGCCAATCTGGACAAGGTCCTCGATG<br>AGATGCGAGGGGCACATGACCTGCGCAACGTGCTGACTTGTATCAAT<br>CGGGCTAGATCCGAGATGATTACCGCAGCCCTGGGAGAACACCAGTC<br>TTACAAGAAAGCTACAGCAGACCTGGCCGCCCTGCATCAGCGCCGAG<br>ATAAGCTGGAGGCACAGATCAGGCAGCAGAACTCTGCCAGTAGGAA<br>ACGCCTGGGACGCCACAGCCCACTGAGCTCCGAACTCGACACAGTGC<br>GAAAACGTATTGATGAGGGCAGAACTGCCCTGAAGAAACTGCGGCG<br>GAAGCTGCTGAAGAAGGACCCCGCACTGAAAGCAGTGGTCGAGGCA<br>GCTGACGATATGGCCAAAAGGGAGACCACACGCGCTGAAGATGCAT<br>GCGGTCTGTATTGGTGTACTAGGAATGAACAGACCGGCAAGCGCGCC |

TABLE 1-continued

Sequences corresponding to SEQ ID NOs: 1-3.

| Sequence Identifier | Sequence |
|---|---|
|  | AAACTGAGAAGGTTCAAGAAATGGAGGGACTCCGAGGCTACCATCTC
TGTCCAGATTCCCGGCGGGCTGACAGTTGAGCAGCTGCTCGGAGGTG
AAAACAATCAGGCACGACTGGAGCTCCGTCCTGAAGGGGTGTGGGTC
CAGGGAGCTCGGAAGAGAAAAGTGGAGCCAGCAGAAGCAGCCAGAA
ACAAGCTGCGGCTGGACGAGGATGGTTACCCTATGAGGAAACTGGGC
ACTGCCATCCTGCACCTGCGCTGCATGTCCGACGAGGATGGCAAGCC
TATCTGGGCCGAAGTGCCAATTACCTATCATCGGGAGATCCCCGCCG
ATGCTAAGATCAAGCGGTGCTACCTGCACAGGTTCCGCGTGGGGAAT
AGGTATCATTGGTCAGTCCGGTTTAGCCTGGAGAGAGGCAAGAAAGG
GGACGATAGCTGGCTGCACCCCCGGGTGGCAACTACCGGTACCGCTG
CAATCGACATTGGATGGAGATGGTTTCCTGATCGACTGCGTGTTGCC
GTGTGGGCTGGATCCGACGGTGCAGAGGGTGAACTGTGCCTCCCCAA
GTGGTGGCTGGATGAGATGTACAGCGTGCGGCTGGACCAGCGGGAG
AGAGATGTGCTGTTCAACGAAATCGTGAGTCTGGTGCTGCCTTGGTTT
CGCAGCCGCCGAGGCGAGCTGTCCGACTATGTTGTGCAGGCCATTAA
GACAATGCATTCATGGCGCGATAAAGGGCGACTGGCCGCCCTGAGCA
TGAGGTGGCGCGACGATCTGGCAGCAGACCCAGGAGCAAACCCAGC
ACACGTGGCTATGTCTATCAGACTGGAGGAATGGCGAAAGCGTGACA
AACATATTTGGTGCGAGGAAGTCAATCTGCGGAGTCAGCTCCAGGGC
AGCCGGAAGGACCTGTACCGGCGGTTCGCTGCAATGCTGACAAGTAG
GTACGGGCGCATCGTCGTTGAGGAATTTGACCTGTCAGCCGTGCAGA
AACTCCCGCCCGCTTCTATTGACGATGGCACTTACAGTCGAGTGAAG
CGTCACAAAGGAGATGCCGCTTGTTCTCATCTGGTCGGCGCCCTGAA
GGACGCAGCACGTCAGCTGGATAAGAAAAACCCAAAGTGGACAACT
AAACGGTGCCACGTGTGCGGCAAGACCGAGAGAAAATGGGAAAATC
CCGGGGAGCTGGAGCACACATGCAAGCATTGTGGCGTGCTGTGGGAC
CGGGATGTGAACGCTGCAAGAAATATCCTGGCAGCTAGCGGTGTCGC
AGTTGACTGGACAAGGCCTCCACTGGCTCCAGCAGCACGTATGACTT
ATCCCCAGGTGGAGAATAGAGAAATGCGGCGGAGCCGGCGGCGGAA
GGAGGCTCTGGAAACCACAAGGGCATCCGGCGATCGCCAGACCGCC |
| SEQ ID NO: 3 | MGAARRRNPKVAAARKGKPPPKATGNCRNYRYGAHEPIANLDKVLDE
MRGAHDLRNVLTCINRARSEMITAALGEHQSYKKATADLAALHQRRDK
LEAQIRQQNSASRKRLGRHSPLSSELDTVRKRIDEGRTALKKLRRKLLKK
DPALKAVVEAADDMAKRETTRAEDACGLYWCTRNEQTGKRAKLRRFK
KWRDSEATISVQIPGGLTVEQLLGGENNQARLELRPEGVWVQGARKRK
VEPAEAARNKLRLDEDGYPMRKLGTAILHLRCMSDEDGKPIWAEVPITY
HREIPADAKIKRCYLHRFRVGNRYHWSVRFSLERGKKGDDSWLHPRVA
TTGTAAIDIGWRWFPDRLRVAVWAGSDGAEGELCLPKWWLDEMYSVR
LDQRERDVLFNEIVSLVLPWFRSRRGELSDYVVQAIKTMHSWRDKGRL
AALSMRWRDDLAADPGANPAHVAMSIRLEEWRKRDKHIWCEEVNLRS
QLQGSRKDLYRRFAAMLTSRYGRIVVEEFDLSAVQKLPPASIDDGTYSR
VKRHKGDAACSHLVGALKDAARQLDKKNPKWTTKRCHVCGKTERKW
ENPGELEHTCKHCGVLWDRDVNAARNILAASGVAVDWTRPPLAPAAR
MTYPQVENREMRRSRRRKEALETTRASGDRQTA |

A nucleic acid sequence encoding the parent polypeptide described herein may be substantially identical to a reference nucleic acid sequence, e.g., SEQ ID NO: 1 or SEQ ID NO: 2. In some embodiments, the variant polypeptide is encoded by a nucleic acid comprising a sequence having least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the reference nucleic acid sequence, e.g., nucleic acid sequence encoding the parent polypeptide, e.g., SEQ ID NO: 1 or SEQ ID NO: 2. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the nucleic acid molecules hybridize to the complementary sequence of the other under stringent conditions (e.g., within a range of medium to high stringency).

In some embodiments, the variant polypeptide is encoded by a nucleic acid sequence having at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more sequence identity, but not 100% sequence identity, to a reference nucleic acid sequence, e.g., nucleic acid sequence encoding the parent polypeptide, e.g., SEQ ID NO: 1 or SEQ ID NO: 2.

In some embodiments, the variant polypeptide of the present disclosure comprises a polypeptide sequence having 50%, 60%, 65%, 70%, 75%, 80%, 85%, 90%, 91%, 92%, 93%, 94%, 95%, 96%, 97%, 98%, or 99%, but not 100%, identity to SEQ ID NO: 3. In some embodiments, the variant polypeptide of the present disclosure comprises a polypeptide sequence having greater than 50%, 60%, 65%, 70%, 75%, 80%, 85%, 90%, 91%, 92%, 93%, 94%, 95%, 96%, 97%, 98%, or 99%, but not 100%, identity to SEQ ID NO: 3.

In some embodiments, the present disclosure describes a variant polypeptide having a specified degree of amino acid sequence identity to one or more reference polypeptides, e.g., a parent polypeptide, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 3. Homology or identity can be determined by amino acid sequence alignment, e.g., using a program such as BLAST, ALIGN, or CLUSTAL, as described herein.

Also provided is a variant polypeptide of the present disclosure having enzymatic activity, e.g., nuclease or endonuclease activity, and comprising an amino acid sequence which differs from the amino acid sequences of any one of a parent polypeptide and SEQ ID NO: 3 by 50, 40, 35, 30, 25, 20, 19, 18, 17, 16, 15, 14, 13, 12, 11, 10, 9, 8, 7, 6, 5, 4, 3, 2, or 1 amino acid residue(s), when aligned using any of the previously described alignment methods.

In some embodiments, the variant polypeptide comprises an alteration at one or more (e.g., several) amino acids of a parent polypeptide, wherein at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 162, 164, 164, 165, 166, 167, 168, 169, 170, 171, 172, 173, 174, 175, 176, 177, 178, 179, 180, 181, 182, 183, 184, 185, 186, 187, 188, 189, 190, 191, 193, 194, 195, 196, 197, 198, 199, 200, or more are altered.

An alteration may comprise a substitution, an insertion, deletion, addition, or fusion of an amino acid or amino acids in a peptide or polypeptide or a nucleotide or nucleotides in a nucleotide or nucleotides relative to a reference sequence. No particular process is implied in how to make a sequence comprising an alteration. For instance, a sequence comprising an alteration can be synthesized directly from individual nucleotides. In other embodiments, an alteration is made by providing and then altering a reference sequence.

A substitution may comprise a replacement of an amino acid or amino acids with a different amino acid or amino acids, or a nucleotide or nucleotides with a different nucleotide or nucleotides, relative to a reference sequence. No particular process is implied in how to make a sequence comprising a substitution. For instance, a sequence comprising a substitution can be synthesized directly from individual amino acids or nucleotides. In other embodiments, a substitution is made by providing and then altering a reference sequence. The nucleic acid sequence can be in a genome of an organism. The nucleic acid sequence can be in a cell. The nucleic acid sequence can be a DNA sequence. The substitution of nucleotides described herein refers to a substitution of up to several kilobases.

In some embodiments, the variant polypeptide comprises one or more of the amino acid substitutions listed in Table 2.

TABLE 2

Single Amino Acid Substitutions in Variants of SEQ ID NO: 3.

| Position | Wild-Type Residue | Substitutions |
|---|---|---|
| 1 | M | |
| 2 | G | R, A, K, Q, N, H |
| 3 | A | R, G, K, Q, N, H |
| 4 | A | R, G, K, Q, N, H |
| 5 | R | G, A, K, Q, N, H |
| 6 | R | G, A, K, Q, N, H |
| 7 | R | G, A, K, Q, N, H |
| 8 | N | R, G, A, K, Q, H |
| 9 | P | R, G, A, K, Q, N, H |
| 10 | K | R, G, A, Q, N, H |
| 11 | V | R, G, A, K, Q, N, H |
| 12 | A | R, G, K, Q, N, H |
| 13 | A | R, G, K, Q, N, H |
| 14 | A | R, G, K, Q, N, H |
| 15 | R | G, A, K, Q, N, H |
| 16 | K | R, G, A, Q, N, H |
| 17 | G | R, A, K, Q, N, H |
| 18 | K | R, G, A, Q, N, H |
| 19 | P | R, G, A, K, Q, N, H |
| 20 | P | R, G, A, K, Q, N, H |
| 21 | P | R, G, A, K, Q, N, H |
| 22 | K | R, G, A, Q, N, H |
| 23 | A | R, G, K, Q, N, H |
| 24 | T | R, G, A, K, Q, N, H |
| 25 | G | R, A, K, Q, N, H |
| 26 | N | R, G, A, K, Q, H |
| 27 | C | R, G, A, K, Q, N, H |
| 28 | R | G, A, K, Q, N, H |
| 29 | N | R, G, A, K, Q, H |
| 30 | Y | R, G, A, K, Q, N, H |
| 31 | R | G, A, K, Q, N, H |
| 32 | Y | R, G, A, K, Q, N, H |
| 33 | G | R, A, K, Q, N, H |
| 34 | A | R, G, K, Q, N, H |
| 35 | H | R, G, A, K, Q, N |
| 36 | E | R, G, A, K, Q, N, H |
| 37 | P | R, G, A, K, Q, N, H |
| 38 | I | R, G, A, K, Q, N, H |
| 39 | A | R, G, K, Q, N, H |
| 40 | N | R, G, A, K, Q, H |
| 41 | L | R, G, A, K, Q, N, H |
| 42 | D | R, G, A, K, Q, N, H |
| 43 | K | R, G, A, Q, N, H |
| 44 | V | R, G, A, K, Q, N, H |
| 45 | L | R, G, A, K, Q, N, H |
| 46 | D | R, G, A, K, Q, N, H |
| 47 | E | R, G, A, K, Q, N, H |
| 48 | M | R, G, A, K, Q, N, H |
| 49 | F | R, G, A, K, Q, N, H |
| 50 | G | R, A, K, Q, N, H |
| 51 | A | R, G, K, Q, N, H |
| 52 | H | R, G, A, K, Q, N |
| 53 | D | R, G, A, K, Q, N, H |
| 54 | L | R, G, A, K, Q, N, H |
| 55 | R | G, A, K, Q, N, H |
| 56 | N | R, G, A, K, Q, H |
| 57 | V | R, G, A, K, Q, N, H |
| 58 | L | R, G, A, K, Q, N, H |
| 59 | T | R, G, A, K, Q, N, H |
| 60 | C | R, G, A, K, Q, N, H |
| 61 | I | R, G, A, K, Q, N, H |
| 62 | N | R, G, A, K, Q, H |
| 63 | R | G, A, K, Q, N, H |
| 64 | A | R, G, K, Q, N, H |
| 65 | R | G, A, K, Q, N, H |
| 66 | S | R, G, A, K, Q, N, H |
| 67 | E | R, G,A, K, Q, N, H |
| 68 | M | R, G, A, K, Q, N, H |
| 69 | I | R, G, A, K, Q, N, H |
| 70 | T | R, G, A, K, Q, N, H |
| 71 | A | R, G, K, Q, N, H |
| 72 | A | R, G, K, Q, N, H |
| 73 | L | R, G, A, K, Q, N, H |

TABLE 2-continued

Single Amino Acid Substitutions in Variants of SEQ ID NO: 3.

| Position | Wild-Type Residue | Substitutions |
|---|---|---|
| 74 | G | R, A, K, Q, N, H |
| 75 | E | R, G, A, K, Q, N, H |
| 76 | H | R, G, A, K, Q, N |
| 77 | Q | R, G, A, K, N, H |
| 78 | S | R, G, A, K, Q, N, H |
| 79 | Y | R, G, A, K, Q, N, H |
| 80 | K | R, G, A, Q, N, H |
| 81 | K | R, G, A, Q, N, H |
| 82 | A | R, G, K, Q, N, H |
| 83 | T | R, G, A, K, Q, N, H |
| 84 | A | R, G, K, Q, N, H |
| 85 | D | R, G, A, K, Q, N, H |
| 86 | L | R, G, A, K, Q, N, H |
| 87 | A | R, G, K, Q, N, H |
| 88 | A | R, G, K, Q, N, H |
| 89 | L | R, G, A, K, Q, N, H |
| 90 | H | R, G, A, K, Q, N |
| 91 | Q | R, G, A, K, N, H |
| 92 | R | G, A, K, Q, N, H |
| 93 | R | G, A, K, Q, N, H |
| 94 | D | R, G, A, K, Q, N, H |
| 95 | K | R, G, A, Q, N, H |
| 96 | L | R, G, A, K, Q, N, H |
| 97 | E | R, G, A, K, Q, N, H |
| 98 | A | R, G, K, Q, N, H |
| 99 | Q | R, G, A, K, N, H |
| 100 | I | R, G, A, K, Q, N, H |
| 101 | R | G, A, K, Q, N, H |
| 102 | Q | R, G, A, K, N, H |
| 103 | Q | R, G, A, K, N, H |
| 104 | N | R, G, A, K, Q, H |
| 105 | S | R, G, A, K, Q, N, H |
| 106 | A | R, G, K, Q, N, H |
| 107 | S | R, G, A, K, Q, N, H |
| 108 | R | G, A, K, Q, N, H |
| 109 | K | R, G, A, Q, N, H |
| 110 | R | G, A, K, Q, N, H |
| 111 | L | R, G, A, K, Q, N, H |
| 112 | G | R, A, K, Q, N, H |
| 113 | R | G, A, K, Q, N, H |
| 114 | H | R, G, A, K, Q, N |
| 115 | S | R, G, A, K, Q, N, H |
| 116 | P | R, G, A, K, Q, N, H |
| 117 | L | R, G, A, K, Q, N, H |
| 118 | S | R, G, A, K, Q, N, H |
| 119 | S | R, G, A, K, Q, N, H |
| 120 | E | R, G, A, K, Q, N, H |
| 121 | L | R, G, A, K, Q, N, H |
| 122 | D | R, G, A, K, Q, N, H |
| 123 | T | R, G, A, K, Q, N, H |
| 124 | V | R, G, A, K, Q, N, H |
| 125 | R | G, A, K, Q, N, H |
| 126 | K | R, G, A, Q, N, H |
| 127 | R | G, A, K, Q, N, H |
| 128 | I | R, G, A, K, Q, N, H |
| 129 | D | R, G, A, K, Q, N, H |
| 130 | E | R, G, A, K, Q, N, H |
| 131 | G | R, A, K, Q, N, H |
| 132 | R | G, A, K, Q, N, H |
| 133 | T | R, G, A, K, Q, N, H |
| 134 | A | R, G, K, Q, N, H |
| 135 | L | R, G, A, K, Q, N, H |
| 136 | K | R, G, A, Q, N, H |
| 137 | K | R, G, A, Q, N, H |
| 138 | L | R, G, A, K, Q, N, H |
| 139 | R | G, A, K, Q, N, H |
| 140 | R | G, A, K, Q, N, H |
| 141 | K | R, G, A, Q, N, H |
| 142 | L | R, G, A, K, Q, N, H |
| 143 | L | R, G, A, K, Q, N, H |
| 144 | K | R, G, A, Q, N, H |
| 145 | K | R, G, A, Q, N, H |
| 146 | D | R, G, A, K, Q, N, H |

TABLE 2-continued

Single Amino Acid Substitutions in Variants of SEQ ID NO: 3.

| Position | Wild-Type Residue | Substitutions |
|---|---|---|
| 147 | P | R, G, A, K, Q, N, H |
| 148 | A | R, G, K, Q, N, H |
| 149 | L | R, G, A, K, Q, N, H |
| 150 | K | R, G, A, Q, N, H |
| 151 | A | R, G, K, Q, N, H |
| 152 | V | R, G, A, K, Q, N, H |
| 153 | V | R, G, A, K, Q, N, H |
| 154 | E | R, G, A, K, Q, N, H |
| 155 | A | R, G, K, Q, N, H |
| 156 | A | R, G, K, Q, N, H |
| 157 | D | R, G, A, K, Q, N, H |
| 158 | D | R, G, A, K, Q, N, H |
| 159 | M | R, G, A, K, Q, N, H |
| 160 | A | R, G, K, Q, N, H |
| 161 | K | R, G, A, Q, N, H |
| 162 | R | G, A, K, Q, N, H |
| 163 | E | R, G, A, K, Q, N, H |
| 164 | T | R, G, A, K, Q, N, H |
| 165 | T | R, G, A, K, Q, N, H |
| 166 | R | G, A, K, Q, N, H |
| 167 | A | R, G, K, Q, N, H |
| 168 | E | R, G, A, K, Q, N, H |
| 169 | D | R, G, A, K, Q, N, H |
| 170 | A | R, G, K, Q, N, H |
| 171 | C | R, G, A, K, Q, N, H |
| 172 | G | R, A, K, Q, N, H |
| 173 | L | R, G, A, K, Q, N, H |
| 174 | Y | R, G, A, K, Q, N, H |
| 175 | W | R, G, A, K, Q, N, H |
| 176 | C | R, G, A, K, Q, N, H |
| 177 | T | R, G, A, K, Q, N, H |
| 178 | R | G, A, K, Q, N, H |
| 179 | N | R, G, A, K, Q, H |
| 180 | E | R, G, A, K, Q, N, H |
| 181 | Q | R, G, A, K, N, H |
| 182 | T | R, G, A, K, Q, N, H |
| 183 | G | R, A, K, Q, N, H |
| 184 | K | R, G, A, Q, N, H |
| 185 | R | G, A, K, Q, N, H |
| 186 | A | R, G, K, Q, N, H |
| 187 | K | R, G, A, Q, N, H |
| 188 | L | R, G, A, K, Q, N, H |
| 189 | R | G, A, K, Q, N, H |
| 190 | R | G, A, K, Q, N, H |
| 191 | F | R, G, A, K, Q, N, H |
| 192 | K | R, G, A, Q, N, H |
| 193 | K | R, G, A, Q, N, H |
| 194 | W | R, G, A, K, Q, N, H |
| 195 | R | G, A, K, Q, N, H |
| 196 | D | R, G, A, K, Q, N, H |
| 197 | S | R, G, A, K, Q, N, H |
| 198 | E | R, G, A, K, Q, N, H |
| 199 | A | R, G, K, Q, N, H |
| 200 | T | R, G, A, K, Q, N, H |
| 201 | I | R, G, A, K, Q, N, H |
| 202 | S | R, G, A, K, Q, N, H |
| 203 | V | R, G, A, K, Q, N, H |
| 204 | Q | R, G, A, K, N, H |
| 205 | I | R, G, A, K, Q, N, H |
| 206 | P | R, G, A, K, Q, N, H |
| 207 | G | R, A, K, Q, N, H |
| 208 | G | R, A, K, Q, N, H |
| 209 | L | R, G, A, K, Q, N, H |
| 210 | T | R, G, A, K, Q, N, H |
| 211 | V | R, G, A, K, Q, N, H |
| 212 | E | R, G, A, K, Q, N, H |
| 213 | Q | R, G, A, K, N, H |
| 214 | L | R, G, A, K, Q, N, H |
| 215 | L | R, G, A, K, Q, N, H |
| 216 | G | R, A, K, Q, N, H |
| 217 | G | R, A, K, Q, N, H |
| 218 | E | R, G, A, K, Q, N, H |
| 219 | N | R, G, A, K, Q, H |

TABLE 2-continued

Single Amino Acid Substitutions in Variants of SEQ ID NO: 3.

| Position | Wild-Type Residue | Substitutions |
|---|---|---|
| 220 | N | R, G, A, K, Q, H |
| 221 | Q | R, G, A, K, N, H |
| 222 | A | R, G, K, Q, N, H |
| 223 | R | G, A, K, Q, N, H |
| 224 | L | R, G, A, K, Q, N, H |
| 225 | E | R, G, A, K, Q, N, H |
| 226 | L | R, G, A, K, Q, N, H |
| 227 | R | G, A, K, Q, N, H |
| 228 | P | R, G, A, K, Q, N, H |
| 229 | E | R, G, A, K, Q, N, H |
| 230 | G | R, A, K, Q, N, H |
| 231 | V | R, G, A, K, Q, N, H |
| 232 | W | R, G, A, K, Q, N, H |
| 233 | V | R, G, A, K, Q, N, H |
| 234 | Q | R, G, A, K, N, H |
| 235 | G | R, A, K, Q, N, H |
| 236 | A | R, G, K, Q, N, H |
| 237 | R | G, A, K, Q, N, H |
| 238 | K | R, G, A, Q, N, H |
| 239 | R | G, A, K, Q, N, H |
| 240 | K | R, G, A, Q, N, H |
| 241 | V | R, G, A, K, Q, N, H |
| 242 | E | R, G, A, K, Q, N, H |
| 243 | P | R, G, A, K, Q, N, H |
| 244 | A | R, G, K, Q, N, H |
| 245 | E | R, G, A, K, Q, N, H |
| 246 | A | R, G, K, Q, N, H |
| 247 | A | R, G, K, Q, N, H |
| 248 | R | G, A, K, Q, N, H |
| 249 | N | R, G, A, K, Q, H |
| 250 | K | R, G, A, Q, N, H |
| 251 | L | R, G, A, K, Q, N, H |
| 252 | R | G, A, K, Q, N, H |
| 253 | L | R, G, A, K, Q, N, H |
| 254 | D | R, G, A, K, Q, N, H |
| 255 | E | R, G, A, K, Q, N, H |
| 256 | D | R, G, A, K, Q, N, H |
| 257 | G | R, A, K, Q, N, H |
| 258 | Y | R, G, A, K, Q, N, H |
| 259 | P | R, G, A, K, Q, N, H |
| 260 | M | R, G, A, K, Q, N, H |
| 261 | R | G, A, K, Q, N, H |
| 262 | K | R, G, A, Q, N, H |
| 263 | L | R, G, A, K, Q, N, H |
| 264 | G | R, A, K, Q, N, H |
| 265 | T | R, G, A, K, Q, N, H |
| 266 | A | R, G, K, Q, N, H |
| 267 | I | R, G, A, K, Q, N, H |
| 268 | L | R, G, A, K, Q, N, H |
| 269 | H | R, G, A, K, Q, N |
| 270 | L | R, G, A, K, Q, N, H |
| 271 | R | G, A, K, Q, N, H |
| 272 | C | R, G, A, K, Q, N, H |
| 273 | M | R, G, A, K, Q, N, H |
| 274 | S | R, G, A, K, Q, N, H |
| 275 | D | R, G, A, K, Q, N, H |
| 276 | E | R, G, A, K, Q, N, H |
| 277 | D | R, G, A, K, Q, N, H |
| 278 | G | R, A, K, Q, N, H |
| 279 | K | R, G, A, Q, N, H |
| 280 | P | R, G, A, K, Q, N, H |
| 281 | I | R, G, A, K, Q, N, H |
| 282 | W | R, G, A, K, Q, N, H |
| 283 | A | R, G, K, Q, N, H |
| 284 | E | R, G, A, K, Q, N, H |
| 285 | V | R, G, A, K, Q, N, H |
| 286 | P | R, G, A, K, Q, N, H |
| 287 | I | R, G, A, K, Q, N, H |
| 288 | T | R, G, A, K, Q, N, H |
| 289 | Y | R, G, A, K, Q, N, H |
| 290 | H | R, G, A, K, Q, N |
| 291 | R | G, A, K, Q, N, H |
| 292 | E | R, G, A, K, Q, N, H |

TABLE 2-continued

Single Amino Acid Substitutions in Variants of SEQ ID NO: 3.

| Position | Wild-Type Residue | Substitutions |
|---|---|---|
| 293 | I | R, G, A, K, Q, N, H |
| 294 | P | R, G, A, K, Q, N, H |
| 295 | A | R, G, K, Q, N, H |
| 296 | D | R, G, A, K, Q, N, H |
| 297 | A | R, G, K, Q, N, H |
| 298 | K | R, G, A, Q, N, H |
| 299 | I | R, G, A, K, Q, N, H |
| 300 | K | R, G, A, Q, N, H |
| 301 | R | G, A, K, Q, N, H |
| 302 | C | R, G, A, K, Q, N, H |
| 303 | Y | R, G, A, K, Q, N, H |
| 304 | L | R, G, A, K, Q, N, H |
| 305 | H | R, G, A, K, Q, N |
| 306 | R | G, A, K, Q, N, H |
| 307 | F | R, G, A, K, Q, N, H |
| 308 | R | G, A, K, Q, N, H |
| 309 | V | R, G, A, K, Q, N, H |
| 310 | G | R, A, K, Q, N, H |
| 311 | N | R, G, A, K, Q, H |
| 312 | R | G, A, K, Q, N, H |
| 313 | Y | R, G, A, K, Q, N, H |
| 314 | H | R, G, A, K, Q, N |
| 315 | W | R, G, A, K, Q, N, H |
| 316 | S | R, G, A, K, Q, N, H |
| 317 | V | R, G, A, K, Q, N, H |
| 318 | R | G, A, K, Q, N, H |
| 319 | F | R, G, A, K, Q, N, H |
| 320 | S | R, G, A, K, Q, N, H |
| 321 | L | R, G, A, K, Q, N, H |
| 322 | E | R, G, A, K, Q, N, H |
| 323 | R | G, A, K, Q, N, H |
| 324 | G | R, A, K, Q, N, H |
| 325 | K | R, G, A, Q, N, H |
| 326 | K | R, G, A, Q, N, H |
| 327 | G | R, A, K, Q, N, H |
| 328 | D | R, G, A, K, Q, N, H |
| 329 | D | R, G, A, K, Q, N, H |
| 330 | S | R, G, A, K, Q, N, H |
| 331 | W | R, G, A, K, Q, N, H |
| 332 | L | R, G, A, K, Q, N, H |
| 333 | H | R, G, A, K, Q, N |
| 334 | P | R, G, A, K, Q, N, H |
| 335 | R | G, A, K, Q, N, H |
| 336 | V | R, G, A, K, Q, N, H |
| 337 | A | R, G, K, Q, N, H |
| 338 | T | R, G, A, K, Q, N, H |
| 339 | T | R, G, A, K, Q, N, H |
| 340 | G | R, A, K, Q, N, H |
| 341 | T | R, G, A, K, Q, N, H |
| 342 | A | R, G, K, Q, N, H |
| 343 | A | R, G, K, Q, N, H |
| 344 | I | R, G, A, K, Q, N, H |
| 345 | D | A |
| 346 | I | R, G, A, K, Q, N, H |
| 347 | G | R, A, K, Q, N, H |
| 348 | W | R, G, A, K, Q, N, H |
| 349 | R | G, A, K, Q, N, H |
| 350 | W | R, G, A, K, Q, N, H |
| 351 | F | R, G, A, K, Q, N, H |
| 352 | P | R, G, A, K, Q, N, H |
| 353 | D | R, G, A, K, Q, N, H |
| 354 | R | G, A, K, Q, N, H |
| 355 | L | R, G, A, K, Q, N, H |
| 356 | R | G, A, K, Q, N, H |
| 357 | V | R, G, A, K, Q, N, H |
| 358 | A | R, G, K, Q, N, H |
| 359 | V | R, G, A, K, Q, N, H |
| 360 | W | R, G, A, K, Q, N, H |
| 361 | A | R, G, K, Q, N, H |
| 362 | G | R, A, K, Q, N, H |
| 363 | S | R, G, A, K, Q, N, H |
| 364 | D | R, G, A, K, Q, N, H |
| 365 | G | R, A, K, Q, N, H |

TABLE 2-continued

Single Amino Acid Substitutions in Variants of SEQ ID NO: 3.

| Position | Wild-Type Residue | Substitutions |
|---|---|---|
| 366 | A | R, G, K, Q, N, H |
| 367 | E | R, G, A, K, Q, N, H |
| 368 | G | R, A, K, Q, N, H |
| 369 | E | R, G, A, K, Q, N, H |
| 370 | L | R, G, A, K, Q, N, H |
| 371 | C | R, G, A, K, Q, N, H |
| 372 | L | R, G, A, K, Q, N, H |
| 373 | P | R, G, A, K, Q, N, H |
| 374 | K | R, G, A, Q, N, H |
| 375 | W | R, G, A, K, Q, N, H |
| 376 | W | R, G, A, K, Q, N, H |
| 377 | L | R, G, A, K, Q, N, H |
| 378 | D | R, G, A, K, Q, N, H |
| 379 | E | R, G, A, K, Q, N, H |
| 380 | M | R, G, A, K, Q, N, H |
| 381 | Y | R, G, A, K, Q, N, H |
| 382 | S | R, G, A, K, Q, N, H |
| 383 | V | R, G, A, K, Q, N, H |
| 384 | R | G, A, K, Q, N, H |
| 385 | L | R, G, A, K, Q, N, H |
| 386 | D | R, G, A, K, Q, N, H |
| 387 | Q | R, G, A, K, N, H |
| 388 | R | G, A, K, Q, N, H |
| 389 | E | R, G, A, K, Q, N, H |
| 390 | R | G, A, K, Q, N, H |
| 391 | D | R, G, A, K, Q, N, H |
| 392 | V | R, G, A, K, Q, N, H |
| 393 | L | R, G, A, K, Q, N, H |
| 394 | F | R, G, A, K, Q, N, H |
| 395 | N | R, G, A, K, Q, H |
| 396 | E | R, G, A, K, Q, N, H |
| 397 | I | R, G, A, K, Q, N, H |
| 398 | V | R, G, A, K, Q, N, H |
| 399 | S | R, G, A, K, Q, N, H |
| 400 | L | R, G, A, K, Q, N, H |
| 401 | V | R, G, A, K, Q, N, H |
| 402 | L | R, G, A, K, Q, N, H |
| 403 | P | R, G, A, K, Q, N, H |
| 404 | W | R, G, A, K, Q, N, H |
| 405 | F | R, G, A, K, Q, N, H |
| 406 | R | G, A, K, Q, N, H |
| 407 | S | R, G, A, K, Q, N, H |
| 408 | R | G, A, K, Q, N, H |
| 409 | R | G, A, K, Q, N, H |
| 410 | G | R, A, K, Q, N, H |
| 411 | E | R, G, A, K, Q, N, H |
| 412 | L | R, G, A, K, Q, N, H |
| 413 | S | R, G, A, K, Q, N, H |
| 414 | D | R, G, A, K, Q, N, H |
| 415 | Y | R, G, A, K, Q, N, H |
| 416 | V | R, G, A, K, Q, N, H |
| 417 | V | R, G, A, K, Q, N, H |
| 418 | Q | R, G, A, K, N, H |
| 419 | A | R, G, K, Q, N, H |
| 420 | I | R, G, A, K, Q, N, H |
| 421 | K | R, G, A, Q, N, H |
| 422 | T | R, G, A, K, Q, N, H |
| 423 | M | R, G, A, K, Q, N, H |
| 424 | H | R, G, A, K, Q, N |
| 425 | S | R, G, A, K, Q, N, H |
| 426 | W | R, G, A, K, Q, N, H |
| 427 | R | G, A, K, Q, N, H |
| 428 | D | R, G, A, K, Q, N, H |
| 429 | K | R, G, A, Q, N, H |
| 430 | G | R, A, K, Q, N, H |
| 431 | R | G, A, K, Q, N, H |
| 432 | L | R, G, A, K, Q, N, H |
| 433 | A | R, G, K, Q, N, H |
| 434 | A | R, G, K, Q, N, H |
| 435 | L | R, G, A, K, Q, N, H |
| 436 | S | R, G, A, K, Q, N, H |
| 437 | M | R, G, A, K, Q, N, H |
| 438 | R | G, A, K, Q, N, H |

TABLE 2-continued

Single Amino Acid Substitutions in Variants of SEQ ID NO: 3.

| Position | Wild-Type Residue | Substitutions |
|---|---|---|
| 439 | W | R, G, A, K, Q, N, H |
| 440 | R | G, A, K, Q, N, H |
| 441 | D | R, G, A, K, Q, N, H |
| 442 | D | R, G, A, K, Q, N, H |
| 443 | L | R, G, A, K, Q, N, H |
| 444 | A | R, G, K, Q, N, H |
| 445 | A | R, G, K, Q, N, H |
| 446 | D | R, G, A, K, Q, N, H |
| 447 | P | R, G, A, K, Q, N, H |
| 448 | G | R, A, K, Q, N, H |
| 449 | A | R, G, K, Q, N, H |
| 450 | N | R, G, A, K, Q, H |
| 451 | P | R, G, A, K, Q, N, H |
| 452 | A | R, G, K, Q, N, H |
| 453 | H | R, G, A, K, Q, N |
| 454 | V | R, G, A, K, Q, N, H |
| 455 | A | R, G, K, Q, N, H |
| 456 | M | R, G, A, K, Q, N, H |
| 457 | S | R, G, A, K, Q, N, H |
| 458 | I | R, G, A, K, Q, N, H |
| 459 | R | G, A, K, Q, N, H |
| 460 | L | R, G, A, K, Q, N, H |
| 461 | E | R, G, A, K, Q, N, H |
| 462 | E | R, G, A, K, Q, N, H |
| 463 | W | R, G, A, K, Q, N, H |
| 464 | R | G, A, K, Q, N, H |
| 465 | K | R, G, A, Q, N, H |
| 466 | R | G, A, K, Q, N, H |
| 467 | D | R, G, A, K, Q, N, H |
| 468 | K | R, G, A, Q, N, H |
| 469 | H | R, G, A, K, Q, N |
| 470 | I | R, G, A, K, Q, N, H |
| 471 | W | R, G, A, K, Q, N, H |
| 472 | C | R, G, A, K, Q, N, H |
| 473 | E | R, G, A, K, Q, N, H |
| 474 | E | R, G, A, K, Q, N, H |
| 475 | V | R, G, A, K, Q, N, H |
| 476 | N | R, G, A, K, Q, H |
| 477 | L | R, G, A, K, Q, N, H |
| 478 | R | G, A, K, Q, N, H |
| 479 | S | R, G, A, K, Q, N, H |
| 480 | Q | R, G, A, K, N, H |
| 481 | L | R, G, A, K, Q, N, H |
| 482 | Q | R, G, A, K, N, H |
| 483 | G | R, A, K, Q, N, H |
| 484 | S | R, G, A, K, Q, N, H |
| 485 | R | G, A, K, Q, N, H |
| 486 | K | R, G, A, Q, N, H |
| 487 | D | R, G, A, K, Q, N, H |
| 488 | L | R, G, A, K, Q, N, H |
| 489 | Y | R, G, A, K, Q, N, H |
| 490 | R | G, A, K, Q, N, H |
| 491 | R | G, A, K, Q, N, H |
| 492 | F | R, G, A, K, Q, N, H |
| 493 | A | R, G, K, Q, N, H |
| 494 | A | R, G, K, Q, N, H |
| 495 | M | R, G, A, K, Q, N, H |
| 496 | L | R, G, A, K, Q, N, H |
| 497 | T | R, G, A, K, Q, N, H |
| 498 | S | R, G, A, K, Q, N, H |
| 499 | R | G, A, K, Q, N, H |
| 500 | Y | R, G, A, K, Q, N, H |
| 501 | G | R, A, K, Q, N, H |
| 502 | R | G, A, K, Q, N, H |
| 503 | I | R, G, A, K, Q, N, H |
| 504 | V | R, G, A, K, Q, N, H |
| 505 | V | R, G, A, K, Q, N, H |
| 506 | E | A |
| 507 | E | R, G, A, K, Q, N, H |
| 508 | F | R, G, A, K, Q, N, H |
| 509 | D | R, G, A, K, Q, N, H |
| 510 | L | R, G, A, K, Q, N, H |
| 511 | S | R, G, A, K, Q, N, H |

TABLE 2-continued

Single Amino Acid Substitutions in Variants of SEQ ID NO: 3.

| Position | Wild-Type Residue | Substitutions |
|---|---|---|
| 512 | A | R, G, K, Q, N, H |
| 513 | V | R, G, A, K, Q, N, H |
| 514 | Q | R, G, A, K, N, H |
| 515 | K | R, G, A, Q, N, H |
| 516 | L | R, G, A, K, Q, N, H |
| 517 | P | R, G, A, K, Q, N, H |
| 518 | P | R, G, A, K, Q, N, H |
| 519 | A | R, G, K, Q, N, H |
| 520 | S | R, G, A, K, Q, N, H |
| 521 | I | R, G, A, K, Q, N, H |
| 522 | D | R, G, A, K, Q, N, H |
| 523 | D | R, G, A, K, Q, N, H |
| 524 | G | R, A, K, Q, N, H |
| 525 | T | R, G, A, K, Q, N, H |
| 526 | Y | R, G, A, K, Q, N, H |
| 527 | S | R, G, A, K, Q, N, H |
| 528 | R | G, A, K, Q, N, H |
| 529 | V | R, G, A, K, Q, N, H |
| 530 | K | R, G, A, Q, N, H |
| 531 | R | G, A, K, Q, N, H |
| 532 | H | R, G, A, K, Q, N |
| 533 | K | R, G, A, Q, N, H |
| 534 | G | R, A, K, Q, N, H |
| 535 | D | R, G, A, K, Q, N, H |
| 536 | A | R, G, K, Q, N, H |
| 537 | A | R, G, K, Q, N, H |
| 538 | C | R, G, A, K, Q, N, H |
| 539 | S | R, G, A, K, Q, N, H |
| 540 | H | R, G, A, K, Q, N |
| 541 | L | R, G, A, K, Q, N, H |
| 542 | V | R, G, A, K, Q, N, H |
| 543 | G | R, A, K, Q, N, H |
| 544 | A | R, G, K, Q, N, H |
| 545 | L | R, G, A, K, Q, N, H |
| 546 | K | R, G, A, Q, N, H |
| 547 | D | R, G, A, K, Q, N, H |
| 548 | A | R, G, K, Q, N, H |
| 549 | A | R, G, K, Q, N, H |
| 550 | R | G, A, K, Q, N, H |
| 551 | Q | R, G, A, K, N, H |
| 552 | L | R, G, A, K, Q, N, H |
| 553 | D | R, G, A, K, Q, N, H |
| 554 | K | R, G, A, Q, N, H |
| 555 | K | R, G, A, Q, N, H |
| 556 | N | R, G, A, K, Q, H |
| 557 | P | R, G, A, K, Q, N, H |
| 558 | K | R, G, A, Q, N, H |
| 559 | W | R, G, A, K, Q, N, H |
| 560 | T | R, G, A, K, Q, N, H |
| 561 | T | R, G, A, K, Q, N, H |
| 562 | K | R, G, A, Q, N, H |
| 563 | R | G, A, K, Q, N, H |
| 564 | C | R, G, A, K, Q, N, H |
| 565 | H | R, G, A, K, Q, N |
| 566 | V | R, G, A, K, Q, N, H |
| 567 | C | R, G, A, K, Q, N, H |
| 568 | G | R, A, K, Q, N, H |
| 569 | K | R, G, A, Q, N, H |
| 570 | T | R, G, A, K, Q, N, H |
| 571 | E | R, G, A, K, Q, N, H |
| 572 | R | G, A, K, Q, N, H |
| 573 | K | R, G, A, Q, N, H |
| 574 | W | R, G, A, K, Q, N, H |
| 575 | E | R, G, A, K, Q, N, H |
| 576 | N | R, G, A, K, Q, H |
| 577 | P | R, G, A, K, Q, N, H |
| 578 | G | R, A, K, Q, N, H |
| 579 | E | R, G, A, K, Q, N, H |
| 580 | L | R, G, A, K, Q, N, H |
| 581 | E | R, G, A, K, Q, N, H |
| 582 | H | R, G, A, K, Q, N |
| 583 | T | R, G, A, K, Q, N, H |
| 584 | C | R, G, A, K, Q, N, H |

TABLE 2-continued

Single Amino Acid Substitutions in Variants of SEQ ID NO: 3.

| Position | Wild-Type Residue | Substitutions |
|---|---|---|
| 585 | K | R, G, A, Q, N, H |
| 586 | H | R, G, A, K, Q, N |
| 587 | C | R, G, A, K, Q, N, H |
| 588 | G | R, A, K, Q, N, H |
| 589 | V | R, G, A, K, Q, N, H |
| 590 | L | R, G, A, K, Q, N, H |
| 591 | W | R, G, A, K, Q, N, H |
| 592 | D | R, G, A, K, Q, N, H |
| 593 | R | G, A, K, Q, N, H |
| 594 | D | R, G, A, K, Q, N, H |
| 595 | V | R, G, A, K, Q, N, H |
| 596 | N | R, G, A, K, Q, H |
| 597 | A | R, G, K, Q, N, H |
| 598 | A | R, G, K, Q, N, H |
| 599 | R | G, A, K, Q, N, H |
| 600 | N | R, G, A, K, Q, H |
| 601 | I | R, G, A, K, Q, N, H |
| 602 | L | R, G, A, K, Q, N, H |
| 603 | A | R, G, K, Q, N, H |
| 604 | A | R, G, K, Q, N, H |
| 605 | S | R, G, A, K, Q, N, H |
| 606 | G | R, A, K, Q, N, H |
| 607 | V | R, G, A, K, Q, N, H |
| 608 | A | R, G, K, Q, N, H |
| 609 | V | R, G, A, K, Q, N, H |
| 610 | D | R, G, A, K, Q, N, H |
| 611 | W | R, G, A, K, Q, N, H |
| 612 | T | R, G, A, K, Q, N, H |
| 613 | R | G, A, K, Q, N, H |
| 614 | P | R, G, A, K, Q, N, H |
| 615 | P | R, G, A, K, Q, N, H |
| 616 | L | R, G, A, K, Q, N, H |
| 617 | A | R, G, K, Q, N, H |
| 618 | P | R, G, A, K, Q, N, H |
| 619 | A | R, G, K, Q, N, H |
| 620 | A | R, G, K, Q, N, H |
| 621 | R | G, A, K, Q, N, H |
| 622 | M | R, G, A, K, Q, N, H |
| 623 | T | R, G, A, K, Q, N, H |
| 624 | Y | R, G, A, K, Q, N, H |
| 625 | P | R, G, A, K, Q, N, H |
| 626 | Q | R, G, A, K, N, H |
| 627 | V | R, G, A, K, Q, N, H |
| 628 | E | R, G, A, K, Q, N, H |
| 629 | N | R, G, A, K, Q, H |
| 630 | R | G, A, K, Q, N, H |
| 631 | E | R, G, A, K, Q, N, H |
| 632 | M | R, G, A, K, Q, N, H |
| 633 | R | G, A, K, Q, N, H |
| 634 | R | G, A, K, Q, N, H |
| 635 | S | R, G, A, K, Q, N, H |
| 636 | R | G, A, K, Q, N, H |
| 637 | R | G, A, K, Q, N, H |
| 638 | R | G, A, K, Q, N, H |
| 639 | K | R, G, A, Q, N, H |
| 640 | E | R, G, A, K, Q, N, H |
| 641 | A | R, G, K, Q, N, H |
| 642 | L | R, G, A, K, Q, N, H |
| 643 | E | R, G, A, K, Q, N, H |
| 644 | T | R, G, A, K, Q, N, H |
| 645 | T | R, G, A, K, Q, N, H |
| 646 | R | G, A, K, Q, N, H |
| 647 | A | R, G, K, Q, N, H |
| 648 | S | R, G, A, K, Q, N, H |
| 649 | G | R, A, K, Q, N, H |
| 650 | D | R, G, A, K, Q, N, H |
| 651 | R | G, A, K, Q, N, H |
| 652 | Q | R, G, A, K, N, H |
| 653 | T | R, G, A, K, Q, N, H |
| 654 | A | R, G, K, Q, N, H |

Some of the beneficial alterations described herein fall within a hotspot located at approximately residues 500-580 of a nuclease polypeptide of SEQ ID NO: 3, which is near the to a RuvC 'lid' separating the TS-spacer helix and ssDNA NTS. Without wishing to be bound by theory, in some embodiments, a substitution described herein has one or more of the following benefits to enzyme function: stabilizing ssDNA NTS entering active site groove; removing H-bond interaction with TS-spacer helix; adding a favorable charge interaction with the TS-spacer helix; and removing charge repulsion with ssDNA TS proceeding from spacer helix.

In some embodiments, the variant polypeptide comprises a D509R amino acid substitution. In some embodiments, the variant polypeptide comprises a S511R amino acid substitution. In some embodiments, the variant polypeptide comprises a I521R amino acid substitution. In some embodiments, the variant polypeptide comprises a D535G amino acid substitution. In some embodiments, the variant polypeptide comprises a Q514G amino acid substitution. In some embodiments, the variant polypeptide comprises a L516R amino acid substitution. In some embodiments, the variant polypeptide comprises a L516G amino acid substitution. In some embodiments, the variant polypeptide comprises a E198R amino acid substitution. In some embodiments, the variant polypeptide comprises a S527R amino acid substitution. In some embodiments, the variant polypeptide comprises a D509K amino acid substitution. In some embodiments, the variant polypeptide comprises a D509G amino acid substitution. In some embodiments, the variant polypeptide comprises a L580G amino acid substitution. In some embodiments, the variant polypeptide comprises a V359R amino acid substitution. In some embodiments, the variant polypeptide comprises a D535K amino acid substitution. In some embodiments, the variant polypeptide comprises a Y381R amino acid substitution. In some embodiments, the variant polypeptide comprises a R354G amino acid substitution. In some embodiments, the variant polypeptide comprises a M380K amino acid substitution. In some embodiments, the variant polypeptide comprises a M380R amino acid substitution. In some embodiments, the variant polypeptide comprises a V383R amino acid substitution. In some embodiments, the variant polypeptide comprises a L580R amino acid substitution. In some embodiments, the variant polypeptide comprises a E367R amino acid substitution. In some embodiments, the variant polypeptide comprises a I521K amino acid substitution. In some embodiments, the variant polypeptide comprises a E367G amino acid substitution. In some embodiments, the variant polypeptide comprises a E507R amino acid substitution. In some embodiments, the variant polypeptide comprises a I521G amino acid substitution. In some embodiments, the variant polypeptide comprises a W350R amino acid substitution. In some embodiments, the variant polypeptide comprises a D535R amino acid substitution. In some embodiments, the variant polypeptide comprises a R528K amino acid substitution. In some embodiments, the variant polypeptide comprises a S527K amino acid substitution. In some embodiments, the variant polypeptide comprises a L385G amino acid substitution. In some embodiments, the variant polypeptide comprises a W350G amino acid substitution. In some embodiments, the variant polypeptide comprises a L516K amino acid substitution. In some embodiments, the variant polypeptide comprises a Y381G amino acid substitution. In some embodiments, the variant polypeptide comprises a H532R amino acid substitution. In some embodiments, the variant polypeptide comprises a D129R amino acid substitution. In some embodiments, the variant polypeptide comprises a P615R amino acid substitution. In some embodiments, the variant polypeptide comprises a G578R amino acid substitution. In some embodiments, the variant polypeptide comprises a M380G amino acid substitution. In some embodiments, the variant polypeptide comprises a V595G amino acid substitution. In some embodiments, the variant polypeptide comprises a R531G amino acid substitution. In some embodiments, the variant polypeptide comprises a D129G amino acid substitution. In some embodiments, the variant polypeptide comprises a R531K amino acid substitution. In some embodiments, the variant polypeptide comprises a D158G amino acid substitution. In some embodiments, the variant polypeptide comprises a N476G amino acid substitution. In some embodiments, the variant polypeptide comprises a G578K amino acid substitution. In some embodiments, the variant polypeptide comprises a A512R amino acid substitution. In some embodiments, the variant polypeptide comprises a P618R amino acid substitution. In some embodiments, the variant polypeptide comprises a V595R amino acid substitution. In some embodiments, the variant polypeptide comprises a V595K amino acid substitution. In some embodiments, the variant polypeptide comprises a V383G amino acid substitution. In some embodiments, the variant polypeptide comprises a A597G amino acid substitution. In some embodiments, the variant polypeptide comprises a Y381K amino acid substitution. In some embodiments, the variant polypeptide comprises a P618G amino acid substitution. In some embodiments, the variant polypeptide comprises a E198K amino acid substitution. In some embodiments, the variant polypeptide comprises a T288R amino acid substitution. In some embodiments, the variant polypeptide comprises a E507K amino acid substitution. In some embodiments, the variant polypeptide comprises a L385R amino acid substitution. In some embodiments, the variant polypeptide comprises a C538G amino acid substitution. In some embodiments, the variant polypeptide comprises a P615G amino acid substitution. In some embodiments, the variant polypeptide comprises a D386R amino acid substitution. In some embodiments, the variant polypeptide comprises a S511K amino acid substitution. In some embodiments, the variant polypeptide comprises a C371G amino acid substitution. In some embodiments, the variant polypeptide comprises a K136G amino acid substitution. In some embodiments, the variant polypeptide comprises a N220R amino acid substitution. In some embodiments, the variant polypeptide comprises a S78K amino acid substitution. In some embodiments, the variant polypeptide comprises a K141G amino acid substitution. In some embodiments, the variant polypeptide comprises a K240R amino acid substitution. In some embodiments, the variant polypeptide comprises a D277R amino acid substitution. In some embodiments, the variant polypeptide comprises a T165R amino acid substitution. In some embodiments, the variant polypeptide comprises a K374R amino acid substitution.

In some embodiments, the variant polypeptide further comprises a second alteration relative to the amino acid sequence of SEQ ID NO: 3. In some embodiments, the alteration comprises L580G and the second alteration comprises L385G. In some embodiments the alteration comprises L580G and the second alteration comprises A512R. In some embodiments the alteration comprises S527R and the second alteration comprises C538G. In some embodiments the alteration comprises D129R and the second alteration comprises P618R. In some embodiments the alteration comprises Q514G and the second alteration comprises A512R. In some embodiments the alteration comprises S527R and the second alteration comprises L385G. In some embodiments the alteration comprises G578R and the second alteration comprises D158G. In some embodiments the alteration comprises S511R and the second alteration comprises P618R. In some embodiments the alteration comprises D158G and the second alteration comprises A512R. In some embodiments the alteration comprises R354G and the second alteration comprises A512R. In some embodiments the alteration comprises A512R and the second alteration comprises P618R. In some embodiments the alteration comprises V359R and the second alteration comprises A512R. In some embodiments the alteration comprises E367R and the second alteration comprises A512R. In some embodiments the alteration comprises Q514G and the second alteration comprises N476G. In some embodiments the alteration comprises S511R and the second alteration comprises A512R. In some embodiments the alteration comprises E198R and the second alteration comprises R354G. In some embodiments the alteration comprises Q514G and the second alteration comprises C538G. In some embodiments the alteration comprises S527R and the second alteration comprises T288R. In some embodiments the alteration comprises R354G and the second alteration comprises D158G. In some embodiments the alteration comprises R354G and the second alteration comprises L385G. In some embodiments the alteration comprises G578R and the second alteration comprises A512R. In some embodiments the alteration comprises R354G and the second alteration comprises E507R. In some embodiments the alteration comprises S527R and the second alteration comprises G578R. In some embodiments the alteration comprises S511R and the second alteration comprises C538G. In some embodiments the alteration comprises I521R and the second alteration comprises V383R. In some embodiments the alteration comprises S511R and the second alteration comprises I521R. In some embodiments the alteration comprises L385G and the second alteration comprises G578R. In some embodiments the alteration comprises L580G and the second alteration comprises N476G. In some embodiments the alteration comprises Q514G and the second alteration comprises T288R. In some embodiments the alteration comprises D535G and the second alteration comprises A512R. In some embodiments the alteration comprises D509R and the second alteration comprises M380R. In some embodiments the alteration comprises S527R and the second alteration comprises C371G. In some embodiments the alteration comprises Q514G and the second alteration comprises D158G. In some embodiments the alteration comprises E198R and the second alteration comprises C538G. In some embodiments the alteration comprises S511R and the second alteration comprises L385G. In some embodiments the alteration comprises S527R and the second alteration comprises N476G. In some embodiments the alteration comprises L516R and the second alteration comprises A512R. In some embodiments the alteration comprises S511R and the second alteration comprises C371G. In some embodiments the alteration comprises L516R and the second alteration comprises C538G. In some embodiments the alteration comprises E198R and the second alteration comprises C371G. In some embodiments the alteration comprises Q514G and the second alteration comprises V383R. In some embodiments the alteration comprises L516R and the second alteration comprises N476G. In some embodiments the alteration comprises D509R and the second alteration comprises T288R. In some embodiments the alteration comprises D509R and the second alteration comprises G578R. In some embodiments the alteration comprises D158G and the second alteration comprises C371G. In some embodiments the alteration comprises I521R and the second alteration comprises N476G. In some embodiments the alteration comprises E198R and the second alteration comprises M380R. In some embodiments the alteration comprises D129R and the second alteration comprises N476G. In some embodiments the alteration comprises M380R and the second alteration comprises A512R. In some embodiments the alteration comprises R354G and the second alteration comprises D129R. In some embodiments the alteration comprises S527R and the second alteration comprises L580G. In some embodiments the alteration comprises R354G and the second alteration comprises N476G. In some embodiments the alteration comprises Q514G and the second alteration comprises P618R. In some embodiments the alteration comprises V383R and the second alteration comprises L385G. In some embodiments the alteration comprises E198R and the second alteration comprises V359R. In some embodiments the alteration comprises D535G and the second alteration comprises N476G. In some embodiments the alteration comprises Q514G and the second alteration comprises L385G. In some embodiments the alteration comprises S511R and the second alteration comprises N476G. In some embodiments the alteration comprises D158G and the second alteration comprises A597G. In some embodiments the alteration comprises L516R and the second alteration comprises G578R. In some embodiments the alteration comprises E198R and the second alteration comprises L580G. In some embodiments the alteration comprises E198R and the second alteration comprises L385G. In some embodiments the alteration comprises L580G and the second alteration comprises V383R. In some embodiments the alteration comprises I521R and the second alteration comprises C371G. In some embodiments the alteration comprises V359R and the second alteration comprises R354G. In some embodiments the alteration comprises Y381R and the second alteration comprises G578R. In some embodiments the alteration comprises E198R and the second alteration comprises V383R. In some embodiments the alteration comprises L580G and the second alteration comprises D386R. In some embodiments the alteration comprises L385G and the second alteration comprises P615R. In some embodiments the alteration comprises V383R and the second alteration comprises G578R. In some embodiments the alteration comprises D535G and the second alteration comprises T288R. In some embodiments the alteration comprises Y381R and the second alteration comprises P618R. In some embodiments the alteration comprises A512R and the second alteration comprises A597G. In some embodiments the alteration comprises Q514G and the second alteration comprises L580G. In some embodiments the alteration comprises S527R and the second alteration comprises P615R. In some embodiments the alteration comprises E198R and the second alteration comprises P615R. In some embodiments the alteration comprises I521R and the second alteration comprises T288R. In some embodiments the alteration comprises Y381R and the second alteration comprises C538G. In some embodiments the alteration comprises S527R and the second alteration comprises A512R. In some embodiments the alteration comprises Y381R and the second alteration comprises C371G. In some embodiments the alteration comprises I521R and the second alteration comprises L385G. In some embodiments the alteration comprises L516R and the second alteration comprises T288R. In some embodiments the alteration comprises L516R and the second alteration comprises D158G. In some embodiments the alteration comprises S527R and the second alteration comprises P618R. In some embodiments the alteration comprises S527R and the second alteration comprises R354G. In some embodiments the alteration comprises Y381R and the second alteration comprises V383R. In some embodiments the alteration comprises A512R and the second alteration comprises C371G. In some embodiments the alteration comprises S511R and the second alteration comprises T288R. In some embodiments the alteration comprises S511R and the second alteration comprises Q514G. In some embodiments the alteration comprises L516R and the second alteration comprises V383R. In some embodiments the alteration comprises A512R and the second alteration comprises C538G. In some embodiments the alteration comprises I521R and the second alteration comprises M380R. In some embodiments the alteration comprises D535G and the second alteration comprises C538G. In some embodiments the alteration comprises E198R and the second alteration comprises T288R. In some embodiments the alteration comprises Q514G and the second alteration comprises M380R. In some embodiments the alteration comprises S527R and the second alteration comprises V383R. In some embodiments the alteration comprises L580G and the second alteration comprises Y381R. In some embodiments the alteration comprises S511R and the second alteration comprises G578R. In some embodiments the alteration comprises Y381R and the second alteration comprises R354G. In some embodiments the alteration comprises L516R and the second alteration comprises L385G. In some embodiments the alteration comprises D535G and the second alteration comprises E198R. In some embodiments the alteration comprises S527R and the second alteration comprises M380R. In some embodiments the alteration comprises L580G and the second alteration comprises M380R. In some embodiments the alteration comprises N476G and the second alteration comprises A597G. In some embodiments the alteration comprises I521R and the second alteration comprises C538G. In some embodiments the alteration comprises R354G and the second alteration comprises G578R. In some embodiments the alteration comprises S511R and the second alteration comprises D386R. In some embodiments the alteration comprises P615R and the second alteration comprises C538G. In some embodiments the alteration comprises L580G and the second alteration comprises T288R. In some embodiments the alteration comprises E507R and the second alteration comprises C538G. In some embodiments the alteration comprises E198R and the second alteration comprises A597G. In some embodiments the alteration comprises P615R and the second alteration comprises G578R. In some embodiments the alteration comprises S511R and the second alteration comprises R354G. In some embodiments the alteration comprises D509R and the second alteration comprises D386R. In some embodiments the alteration comprises S511R and the second alteration comprises L580G. In some embodiments the alteration comprises E198R and the second alteration comprises S527R. In some embodiments the alteration comprises V359R and the second alteration comprises G578R. In some embodiments the alteration comprises I521R and the second alteration comprises A512R. In some embodiments the alteration comprises D509R and the second alteration comprises C538G. In some embodiments the alteration comprises L385G and the second alteration comprises P618R. In some embodiments the alteration comprises P615R and the second alteration comprises A512R. In some embodiments the alteration comprises V383R and the second alteration comprises A512R. In some embodiments the alteration comprises L580G and the second alteration comprises C538G. In some embodiments the alteration comprises G578R and the second alteration comprises C538G. In some embodiments the alteration comprises D535G and the second alteration comprises L385G. In some embodiments the alteration comprises L516R and the second alteration comprises D386R. In some embodiments the alteration comprises L516R and the second alteration comprises E507R. In some embodiments the alteration comprises S511R and the second alteration comprises Y381R. In some embodiments the alteration comprises G578R and the second alteration comprises N476G. In some embodiments the alteration comprises E507R and the second alteration comprises C371G. In some embodiments the alteration comprises G578R and the second alteration comprises T288R. In some embodiments the alteration comprises L385G and the second alteration comprises A597G. In some embodiments the alteration comprises I521R and the second alteration comprises D535G. In some embodiments the alteration comprises S527R and the second alteration comprises A597G. In some embodiments the alteration comprises I521R and the second alteration comprises E198R. In some embodiments the alteration comprises S511R and the second alteration comprises E198R. In some embodiments the alteration comprises S511R and the second alteration comprises M380R. In some embodiments the alteration comprises S511R and the second alteration comprises E507R. In some embodiments the alteration comprises D129R and the second alteration comprises A512R. In some embodiments the alteration comprises G578R and the second alteration comprises C371G. In some embodiments the alteration comprises D509R and the second alteration comprises L385G. In some embodiments the alteration comprises I521R and the second alteration comprises P618R. In some embodiments the alteration comprises S511R and the second alteration comprises V383R. In some embodiments the alteration comprises L385G and the second alteration comprises A512R. In some embodiments the alteration comprises D509R and the second alteration comprises P618R. In some embodiments the alteration comprises Y381R and the second alteration comprises L385G. In some embodiments the alteration comprises E367R and the second alteration comprises L385G. In some embodiments the alteration comprises Q514G and the second alteration comprises D129R. In some embodiments the alteration comprises E198R and the second alteration comprises E367R. In some embodiments the alteration comprises D129R and the second alteration comprises C371G. In some embodiments the alteration comprises S527R and the second alteration comprises D386R. In some embodiments the alteration comprises Q514G and the second alteration comprises E507R. In some embodiments the alteration comprises V359R and the second alteration comprises L385G. In some embodiments the alteration comprises M380R and the second alteration comprises L385G. In some embodiments the alteration comprises Q514G and the second alteration comprises R354G. In some embodiments the alteration comprises E198R and the second alteration comprises Y381R. In some embodiments the alteration comprises M380R and the second alteration comprises D129R. In some embodiments the alteration comprises L580G and the second alteration comprises D129R. In some embodiments the alteration comprises D129R and the second alteration comprises G578R. In some embodiments the alteration comprises S511R and the second alteration comprises A597G. In some embodiments the alteration comprises D535G and the second alteration comprises D158G. In some embodiments the alteration comprises N476G and the second alteration comprises A512R. In some embodiments the alteration comprises Q514G and the second alteration comprises L516R. In some embodiments the alteration comprises E507R and the second alteration comprises P618R. In some embodiments the alteration comprises V383R and the second alteration comprises D129R. In some embodiments the alteration comprises L385G and the second alteration comprises C538G. In some embodiments the alteration comprises I521R and the second alteration comprises D158G. In some embodiments the alteration comprises L516R and the second alteration comprises L580G. In some embodiments the alteration comprises S527R and the second alteration comprises D158G. In some embodiments the alteration comprises H532R and the second alteration comprises A512R. In some embodiments the alteration comprises I521R and the second alteration comprises R354G. In some embodiments the alteration comprises I521R and the second alteration comprises Y381R. In some embodiments the alteration comprises D129R and the second alteration comprises P615R. In some embodiments the alteration comprises V359R and the second alteration comprises E507R. In some embodiments the alteration comprises E507R and the second alteration comprises G578R. In some embodiments the alteration comprises L516R and the second alteration comprises P618R. In some embodiments the alteration comprises R354G and the second alteration comprises M380R. In some embodiments the alteration comprises R354G and the second alteration comprises D386R. In some embodiments the alteration comprises I521R and the second alteration comprises G578R. In some embodiments the alteration comprises Y381R and the second alteration comprises A512R. In some embodiments the alteration comprises A512R and the second alteration comprises D386R. In some embodiments the alteration comprises M380R and the second alteration comprises G578R. In some embodiments the alteration comprises Y381R and the second alteration comprises E507R. In some embodiments the alteration comprises L580G and the second alteration comprises E507R. In some embodiments the alteration comprises V359R and the second alteration comprises Y381R. In some embodiments the alteration comprises P615R and the second alteration comprises N476G. In some embodiments the alteration comprises D158G and the second alteration comprises N476G. In some embodiments the alteration comprises Y381R and the second alteration comprises P615R. In some embodiments the alteration comprises V595G and the second alteration comprises A512R. In some embodiments the alteration comprises V383R and the second alteration comprises D158G. In some embodiments the alteration comprises E507R and the second alteration comprises D158G. In some embodiments the alteration comprises V383R and the second alteration comprises C538G. In some embodiments the alteration comprises V383R and the second alteration comprises E507R. In some embodiments the alteration comprises E198R and the second alteration comprises D386R. In some embodiments the alteration comprises D129R and the second alteration comprises D386R. In some embodiments the alteration comprises M380R and the second alteration comprises D158G. In some embodiments the alteration comprises E198R and the second alteration comprises P618R. In some embodiments the alteration comprises Q514G and the second alteration comprises E198R. In some embodiments the alteration comprises I521R and the second alteration comprises S527R. In some embodiments the alteration comprises E198R and the second alteration comprises A512R. In some embodiments the alteration comprises L385G and the second alteration comprises C371G. In some embodiments the alteration comprises H532R and the second alteration comprises C538G. In some embodiments the alteration comprises N476G and the second alteration comprises C371G. In some embodiments the alteration comprises Y381R and the second alteration comprises N476G. In some embodiments the alteration comprises M380R and the second alteration comprises V383R. In some embodiments the alteration comprises H532R and the second alteration comprises T288R. In some embodiments the alteration comprises Q514G and the second alteration comprises D386R. In some embodiments the alteration comprises R354G and the second alteration comprises T288R. In some embodiments the alteration comprises Y381R and the second alteration comprises D158G. In some embodiments the alteration comprises M380R and the second alteration comprises E507R. In some embodiments the alteration comprises P615R and the second alteration comprises C371G. In some embodiments the alteration comprises S527R and the second alteration comprises D129R. In some embodiments the alteration comprises M380R and the second alteration comprises C538G. In some embodiments the alteration comprises L580G and the second alteration comprises R354G. In some embodiments the alteration comprises L385G and the second alteration comprises T288R. In some embodiments the alteration comprises L580G and the second alteration comprises G578R. In some embodiments the alteration comprises E507R and the second alteration comprises L385G. In some embodiments the alteration comprises E507R and the second alteration comprises P615R. In some embodiments the alteration comprises E198R and the second alteration comprises E507R. In some embodiments the alteration comprises S511R and the second alteration comprises D158G. In some embodiments the alteration comprises G578R and the second alteration comprises P618R. In some embodiments the alteration comprises D509R and the second alteration comprises P615R. In some embodiments the alteration comprises D158G and the second alteration comprises D386R. In some embodiments the alteration comprises I521R and the second alteration comprises Q514G. In some embodiments the alteration comprises D535G and the second alteration comprises D386R. In some embodiments the alteration comprises P615R and the second alteration comprises D386R. In some embodiments the alteration comprises D535G and the second alteration comprises G578R. In some embodiments the alteration comprises D535G and the second alteration comprises S527R. In some embodiments the alteration comprises Y381R and the second alteration comprises D386R. In some embodiments the alteration comprises D129R and the second alteration comprises D158G. In some embodiments the alteration comprises Q514G and the second alteration comprises G578R. In some embodiments the alteration comprises L516R and the second alteration comprises D129R. In some embodiments the alteration comprises L385G and the second alteration comprises D129R. In some embodiments the alteration comprises L385G and the second alteration comprises D158G. In some embodiments the alteration comprises E198R and the second alteration comprises H532R. In some embodiments the alteration comprises Q514G and the second alteration comprises C371G. In some embodiments the alteration comprises G578R and the second alteration comprises D386R. In some embodiments the alteration comprises R354G and the second alteration comprises A597G. In some embodiments the alteration comprises Q514G and the second alteration comprises A597G. In some embodiments the alteration comprises E367R and the second alteration comprises E507R. In some embodiments the alteration comprises L580G and the second alteration comprises C371G. In some embodiments the alteration comprises E367R and the second alteration comprises G578R. In some embodiments the alteration comprises L516R and the second alteration comprises M380R. In some embodiments the alteration comprises H532R and the second alteration comprises N476G. In some embodiments the alteration comprises V359R and the second alteration comprises D129R. In some embodiments the alteration comprises S511R and the second alteration comprises P615R. In some embodiments the alteration comprises Q514G and the second alteration comprises Y381R. In some embodiments the alteration comprises M380R and the second alteration comprises N476G. In some embodiments the alteration comprises Q514G and the second alteration comprises P615R. In some embodiments the alteration comprises D158G and the second alteration comprises C538G. In some embodiments the alteration comprises Y381R and the second alteration comprises E367R. In some embodiments the alteration comprises I521R and the second alteration comprises E507R. In some embodiments the alteration comprises I521R and the second alteration comprises L516R. In some embodiments the alteration comprises L385G and the second alteration comprises N476G. In some embodiments the alteration comprises E198R and the second alteration comprises N476G. In some embodiments the alteration comprises R531G and the second alteration comprises T288R. In some embodiments the alteration comprises Y381R and the second alteration comprises T288R. In some embodiments the alteration comprises Y381R and the second alteration comprises V595G. In some embodiments the alteration comprises P615R and the second alteration comprises D158G. In some embodiments the alteration comprises D509R and the second alteration comprises E198R. In some embodiments the alteration comprises E507R and the second alteration comprises V595G. In some embodiments the alteration comprises L580G and the second alteration comprises P615R. In some embodiments the alteration comprises D509R and the second alteration comprises L580G. In some embodiments the alteration comprises V359R and the second alteration comprises D158G. In some embodiments the alteration comprises S527R and the second alteration comprises Y381R. In some embodiments the alteration comprises D509R and the second alteration comprises C371G. In some embodiments the alteration comprises E198R and the second alteration comprises G578R. In some embodiments the alteration comprises D535G and the second alteration comprises D129R. In some embodiments the alteration comprises L516R and the second alteration comprises P615R. In some embodiments the alteration comprises D129R and the second alteration comprises T288R. In some embodiments the alteration comprises R354G and the second alteration comprises V383R. In some embodiments the alteration comprises E507R and the second alteration comprises D129R. In some embodiments the alteration comprises E507R and the second alteration comprises A512R. In some embodiments the alteration comprises N476G and the second alteration comprises C538G. In some embodiments the alteration comprises I521R and the second alteration comprises L580G. In some embodiments the alteration comprises L516R and the second alteration comprises C371G. In some embodiments the alteration comprises D535G and the second alteration comprises L580G. In some embodiments the alteration comprises D535G and the second alteration comprises E507R. In some embodiments the alteration comprises D129R and the second alteration comprises C538G. In some embodiments the alteration comprises R354G and the second alteration comprises C538G. In some embodiments the alteration comprises I521R and the second alteration comprises D386R. In some embodiments the alteration comprises Y381R and the second alteration comprises D129R. In some embodiments the alteration comprises V383R and the second alteration comprises N476G. In some embodiments the alteration comprises M380R and the second alteration comprises P615R. In some embodiments the alteration comprises E507R and the second alteration comprises A597G. In some embodiments the alteration comprises S527R and the second alteration comprises E507R. In some embodiments the alteration comprises I521R and the second alteration comprises D129R. In some embodiments the alteration comprises Q514G and the second alteration comprises V359R. In some embodiments the alteration comprises Y381R and the second alteration comprises A597G. In some embodiments the alteration comprises S511R and the second alteration comprises D535G. In some embodiments the alteration comprises L580G and the second alteration comprises D158G. In some embodiments the alteration comprises D509R and the second alteration comprises D158G. In some embodiments the alteration comprises E198R and the second alteration comprises D129R. In some embodiments the alteration comprises L385G and the second alteration comprises V595G. In some embodiments the alteration comprises P615R and the second alteration comprises T288R. In some embodiments the alteration comprises M380R and the second alteration comprises P618R. In some embodiments the alteration comprises V383R and the second alteration comprises C371G. In some embodiments the alteration comprises D509R and the second alteration comprises N476G. In some embodiments the alteration comprises M380R and the second alteration comprises T288R. In some embodiments the alteration comprises S511R and the second alteration comprises S527R. In some embodiments the alteration comprises D158G and the second alteration comprises T288R. In some embodiments the alteration comprises Q514G and the second alteration comprises S527R. In some embodiments the alteration comprises L516R and the second alteration comprises Y381R. In some embodiments the alteration comprises R354G and the second alteration comprises E367R. In some embodiments the alteration comprises A512R and the second alteration comprises T288R. In some embodiments the alteration comprises V359R and the second alteration comprises D386R. In some embodiments the alteration comprises S527R and the second alteration comprises V595G. In some embodiments the alteration comprises D509R and the second alteration comprises A512R. In some embodiments the alteration comprises D535G and the second alteration comprises Q514G. In some embodiments the alteration comprises W350R and the second alteration comprises N476G. In some embodiments the alteration comprises S511R and the second alteration comprises D129R. In some embodiments the alteration comprises V359R and the second alteration comprises P615R. In some embodiments the alteration comprises I521R and the second alteration comprises P615R. In some embodiments the alteration comprises M380R and the second alteration comprises A597G. In some embodiments the alteration comprises E367R and the second alteration comprises D386R. In some embodiments the alteration comprises M380R and the second alteration comprises D386R. In some embodiments the alteration comprises L516R and the second alteration comprises S527R. In some embodiments the alteration comprises L385G and the second alteration comprises D386R. In some embodiments the alteration comprises V383R and the second alteration comprises T288R. In some embodiments the alteration comprises V359R and the second alteration comprises M380R. In some embodiments the alteration comprises L385G and the second alteration comprises H532R. In some embodiments the alteration comprises S511R and the second alteration comprises V359R. In some embodiments the alteration comprises R354G and the second alteration comprises P615R. In some embodiments the alteration comprises L516R and the second alteration comprises A597G. In some embodiments the alteration comprises E507R and the second alteration comprises D386R. In some embodiments the alteration comprises I521R and the second alteration comprises A597G. In some embodiments the alteration comprises V595G and the second alteration comprises D386R. In some embodiments the alteration comprises N476G and the second alteration comprises P618R. In some embodiments the alteration comprises E367R and the second alteration comprises D129R. In some embodiments the alteration comprises D535G and the second alteration comprises M380R. In some embodiments the alteration comprises S527R and the second alteration comprises H532R. In some embodiments the alteration comprises D509R and the second alteration comprises I521R. In some embodiments the alteration comprises E198R and the second alteration comprises V595G. In some embodiments the alteration comprises E198R and the second alteration comprises D158G. In some embodiments the alteration comprises D509R and the second alteration comprises A597G. In some embodiments the alteration comprises A597G and the second alteration comprises T288R. In some embodiments the alteration comprises D509R and the second alteration comprises D129R. In some embodiments the alteration comprises P615R and the second alteration comprises A597G. In some embodiments the alteration comprises S511R and the second alteration comprises E367R. In some embodiments the alteration comprises L516R and the second alteration comprises E198R. In some embodiments the alteration comprises D535G and the second alteration comprises A597G. In some embodiments the alteration comprises H532R and the second alteration comprises D158G. In some embodiments the alteration comprises H532R and the second alteration comprises D129R. In some embodiments the alteration comprises D535G and the second alteration comprises Y381R. In some embodiments the alteration comprises E507R and the second alteration comprises T288R. In some embodiments the alteration comprises H532R and the second alteration comprises G578R. In some embodiments the alteration comprises D509R and the second alteration comprises L516R. In some embodiments the alteration comprises G578R and the second alteration comprises A597G. In some embodiments the alteration comprises L580G and the second alteration comprises A597G. In some embodiments the alteration comprises R531G and the second alteration comprises C371G. In some embodiments the alteration comprises D535G and the second alteration comprises C371G. In some embodiments the alteration comprises E507R and the second alteration comprises N476G. In some embodiments the alteration comprises L516R and the second alteration comprises H532R. In some embodiments the alteration comprises V383R and the second alteration comprises A597G. In some embodiments the alteration comprises G578R and the second alteration comprises V595G. In some embodiments the alteration comprises D509R and the second alteration comprises Y381R. In some embodiments the alteration comprises D158G and the second alteration comprises P618R. In some embodiments the alteration comprises P618R and the second alteration comprises C538G. In some embodiments the alteration comprises P618R and the second alteration comprises C371G. In some embodiments the alteration comprises N476G and the second alteration comprises D386R. In some embodiments the alteration comprises V359R and the second alteration comprises P618R. In some embodiments the alteration comprises D509R and the second alteration comprises Q514G. In some embodiments the alteration comprises H532R and the second alteration comprises D386R. In some embodiments the alteration comprises L580G and the second alteration comprises W350R. In some embodiments the alteration comprises S527R and the second alteration comprises V359R. In some embodiments the alteration comprises T288R and the second alteration comprises C371G. In some embodiments the alteration comprises I521R and the second alteration comprises H532R. In some embodiments the alteration comprises W350R and the second alteration comprises A512R. In some embodiments the alteration comprises V595G and the second alteration comprises D158G. In some embodiments the alteration comprises Y381R and the second alteration comprises M380R. In some embodiments the alteration comprises M380R and the second alteration comprises R531G. In some embodiments the alteration comprises D535G and the second alteration comprises L516R. In some embodiments the alteration comprises M380R and the second alteration comprises C371G. In some embodiments the alteration comprises V595G and the second alteration comprises C538G. In some embodiments the alteration comprises L516R and the second alteration comprises R354G. In some embodiments the alteration comprises D129R and the second alteration comprises V595G. In some embodiments the alteration comprises D509R and the second alteration comprises S527R. In some embodiments the alteration comprises V383R and the second alteration comprises P615R. In some embodiments the alteration comprises Y381R and the second alteration comprises H532R. In some embodiments the alteration comprises D129R and the second alteration comprises A597G. In some embodiments the alteration comprises L516R and the second alteration comprises R531G. In some embodiments the alteration comprises D386R and the second alteration comprises C371G. In some embodiments the alteration comprises H532R and the second alteration comprises C371G. In some embodiments the alteration comprises W350R and the second alteration comprises C538G. In some embodiments the alteration comprises V383R and the second alteration comprises W350R. In some embodiments the alteration comprises P615R and the second alteration comprises P618R. In some embodiments the alteration comprises S511R and the second alteration comprises H532R. In some embodiments the alteration comprises R354G and the second alteration comprises P618R. In some embodiments the alteration comprises G578R and the second alteration comprises R531G. In some embodiments the alteration comprises E367R and the second alteration comprises D158G. In some embodiments the alteration comprises V359R and the second alteration comprises A597G. In some embodiments the alteration comprises L580G and the second alteration comprises P618R. In some embodiments the alteration comprises I521R and the second alteration comprises W350R. In some embodiments the alteration comprises W350R and the second alteration comprises G578R. In some embodiments the alteration comprises Q514G and the second alteration comprises E367R. In some embodiments the alteration comprises S511R and the second alteration comprises V595G. In some embodiments the alteration comprises C538G and the second alteration comprises D386R. In some embodiments the alteration comprises A597G and the second alteration comprises D386R. In some embodiments the alteration comprises H532R and the second alteration comprises P615R. In some embodiments the alteration comprises V359R and the second alteration comprises V595G. In some embodiments the alteration comprises M380R and the second alteration comprises H532R. In some embodiments the alteration comprises W350R and the second alteration comprises P618R. In some embodiments the alteration comprises H532R and the second alteration comprises P618R. In some embodiments the alteration comprises Q514G and the second alteration comprises H532R. In some embodiments the alteration comprises L580G and the second alteration comprises H532R. In some embodiments the alteration comprises W350R and the second alteration comprises T288R. In some embodiments the alteration comprises D509R and the second alteration comprises E507R. In some embodiments the alteration comprises P618R and the second alteration comprises D386R. In some embodiments the alteration comprises E507R and the second alteration comprises W350R. In some embodiments the alteration comprises A597G and the second alteration comprises C538G. In some embodiments the alteration comprises S511R and the second alteration comprises L516R. In some embodiments the alteration comprises W350R and the second alteration comprises L385G. In some embodiments the alteration comprises W350R and the second alteration comprises D158G. In some embodiments the alteration comprises P618R and the second alteration comprises A597G. In some embodiments the alteration comprises Q514G and the second alteration comprises V595G. In some embodiments the alteration comprises E198R and the second alteration comprises W350R. In some embodiments the alteration comprises D509R and the second alteration comprises V383R. In some embodiments the alteration comprises D509R and the second alteration comprises R354G.

In some embodiments, the variant polypeptide comprises D535G, L516R, and I521R substitutions. In some embodiments, the variant polypeptide comprises D509R, L516R, and I521R substitutions. In some embodiments, the variant polypeptide comprises D535G, L516R, and Q514G substitutions. In some embodiments, the variant polypeptide comprises D535G, Q514G, and I521R substitutions. In some embodiments, the variant polypeptide comprises Q514G, I521R, L580G, and E198R substitutions. In some embodiments, the variant polypeptide comprises D535G, Q514G, I521R, and E198R substitutions. In some embodiments, the variant polypeptide comprises D535G, L516R, Q514G, and I521R substitutions. In some embodiments, the variant polypeptide comprises Q514G, I521R, S527R, and E198R substitutions. In some embodiments, the variant polypeptide comprises D509R, D535G, L516R, Q514G, and I521R substitutions. In some embodiments, the variant polypeptide comprises D535G, L516R, I521R, and S527R substitutions. In some embodiments, the variant polypeptide comprises D535G, I521R, L580G, and E198R substitutions. In some embodiments, the variant polypeptide comprises D509R, D535G, and L516R substitutions. In some embodiments, the variant polypeptide comprises I521R, S527R, E198R, and M380R substitutions. In some embodiments, the variant polypeptide comprises D509R, L516R, and Q514G substitutions. In some embodiments, the variant polypeptide comprises D509R, Q514G, and I521R substitutions. In some embodiments, the variant polypeptide comprises D535G, L516R, Q514G, and S511R substitutions. In some embodiments, the variant polypeptide comprises D535G, L516R, Q514G, and S527R substitutions. In some embodiments, the variant polypeptide comprises I521R, S527R, L580G, and E198R substitutions. In some embodiments, the variant polypeptide comprises D535G, L516R, S527R, and M380R substitutions. In some embodiments, the variant polypeptide comprises Q514G, S527R, L580G, and E198R substitutions. In some embodiments, the variant polypeptide comprises L516R, Q514G, I521R, and M380R substitutions. In some embodiments, the variant polypeptide comprises D509R, L516R, Q514G, And S527R substitutions. In some embodiments, the variant polypeptide comprises D509R, I521R, L580G, and E198R substitutions. In some embodiments, the variant polypeptide comprises S527R, L580G, E198R, and M380R substitutions. In some embodiments, the variant polypeptide comprises L516R, S527R, L580G, and E198R substitutions. In some embodiments, the variant polypeptide comprises D509R, Q514G, I521R, and E198R substitutions. In some embodiments, the variant polypeptide comprises D535G, Q514G, I521R, and S527R substitutions. In some embodiments, the variant polypeptide comprises Q514G, L580G, E198R, and M380R substitutions. In some embodiments, the variant polypeptide comprises D509R, L516R, I521R, and E198R substitutions. In some embodiments, the variant polypeptide comprises L516R, Q514G, I521R, and L580G substitutions. In some embodiments, the variant polypeptide comprises D509R, D535G, Q514G, and E198R substitutions. In some embodiments, the variant polypeptide comprises L516R, I521R, S527R, and L580G substitutions. In some embodiments, the variant polypeptide comprises D535G, I521R, S527R, and M380R substitutions. In some embodiments, the variant polypeptide comprises L516R, I521R, L580G, and E198R substitutions. In some embodiments, the variant polypeptide comprises D509R, D535G, and I521R substitutions. In some embodiments, the variant polypeptide comprises D535G, S527R, L580G, and E198R substitutions. In some embodiments, the variant polypeptide comprises D509R, D535G, and Q514G substitutions. In some embodiments, the variant polypeptide comprises S527R, L580G, E198R, and R354G substitutions. In some embodiments, the variant polypeptide comprises Q514G, I521R, S527R, and L580G substitutions. In some embodiments, the variant polypeptide comprises D535G, Q514G, E198R, and M380R substitutions. In some embodiments, the variant polypeptide comprises L516R, Q514G, L580G, and E198R substitutions. In some embodiments, the variant polypeptide comprises I521R, S527R, E198R, and R354G substitutions. In some embodiments, the variant polypeptide comprises I521R, S527R, R354G, and M380R substitutions. In some embodiments, the variant polypeptide comprises I521R, L580G, E198R, and M380R substitutions. In some embodiments, the variant polypeptide comprises L516R, Q514G, S527R, and L580G substitutions. In some embodiments, the variant polypeptide comprises D535G, Q514G, S527R, and E198R substitutions. In some embodiments, the variant polypeptide comprises D509R, Q514G, L580G, and E198R substitutions. In some embodiments, the variant polypeptide comprises K136G, N220R, and M380R substitutions. In some embodiments, the variant polypeptide comprises S78K, E198R, and R354G substitutions. In some embodiments, the variant polypeptide comprises K141G, N220R, and M380R substitutions. In some embodiments, the variant polypeptide comprises K141G, K240R, and M380R substitutions. In some embodiments, the variant polypeptide comprises K141G, D277R, and M380R substitutions. In some embodiments, the variant polypeptide comprises K136G, D277R, and M380R substitutions. In some embodiments, the variant polypeptide comprises S78K, E198R, and L385R substitutions. In some embodiments, the variant polypeptide comprises L580G, L385G, S511R, and A512R substitutions. In some embodiments, the variant polypeptide comprises S78K, E198R, and M380R substitutions. In some embodiments, the variant polypeptide comprises K136G, K240R, and M380R substitutions. In some embodiments, the variant polypeptide comprises T165R, N220R, and M380R substitutions. In some embodiments, the variant polypeptide comprises L580G, L385G, Q514G, and A512R substitutions. In some embodiments, the variant polypeptide comprises D129R, P618R, S511R, and A512R substitutions. In some embodiments, the variant polypeptide comprises S78K, E198R, and K374R substitutions. In some embodiments, the variant polypeptide comprises T165R, D277R, and M380R substitutions. In some embodiments, the variant polypeptide comprises L580G, L385G, G578R, and D158G substitutions. In some embodiments, the variant polypeptide comprises D129R, P618R, R354G, and A512R substitutions. In some embodiments, the variant polypeptide comprises T165R, K240R, and M380R substitutions. In some embodiments, the variant polypeptide comprises K141G, K240R, and L385R substitutions. In some embodiments, the variant polypeptide comprises K136G, N220R, and L385R substitutions. In some embodiments, the variant polypeptide comprises D129R, P618R, Q514G, and A512R substitutions. In some embodiments, the variant polypeptide comprises D129R, P618R, S527R, and L385G substitutions. In some embodiments, the variant polypeptide comprises K141G, N220R, and L385R substitutions. In some embodiments, the variant polypeptide comprises L580G, L385G, Q514G, and N476G substitutions. In some embodiments, the variant polypeptide comprises L580G, L385G, A512R, and P618R substitutions. In some embodiments, the variant polypeptide comprises K141G, D277R, and L385R substitutions. In some embodiments, the variant polypeptide comprises D129R, P618R, D158G, and A512R substitutions. In some embodiments, the variant polypeptide comprises K136G, N220R, and K374R substitutions. In some embodiments, the variant polypeptide comprises K136G, D277R, and L385R substitutions. In some embodiments, the variant polypeptide comprises K136G, K240R, and L385R substitutions. In some embodiments, the variant polypeptide comprises L580G, L385G, S527R, and C538G substitutions. In some embodiments, the variant polypeptide comprises T165R, K240R, and L385R substitutions. In some embodiments, the variant polypeptide comprises D129R, P618R, V359R, and A512R substitutions.

In some embodiments, the variant polypeptide comprises an alteration that increases interactions of the variant polypeptide to the RNA guide. In some embodiments, the alteration that increases interactions with the RNA guide is an arginine, lysine, glutamine, asparagine, or histidine substitution. In some embodiments, the variant polypeptide comprises an alteration that increases interactions of the variant polypeptide to the target nucleic acid. In some embodiments, the alteration that increases interactions with the target nucleic acid is an arginine, lysine, glutamine, asparagine, or histidine substitution. In some embodiments, the variant polypeptide comprises an alanine substitution. In some embodiments, the alanine substitution does not affect the geometry of the variant polypeptide backbone. In some embodiments, the variant polypeptide comprises a glycine substitution. In some embodiments, the glycine substitution alters the Ramachandran bond angles of the variant polypeptide backbone.

In some embodiments, the variant polypeptide comprises at least one RuvC motif or a RuvC domain. As used herein, a "biologically active portion" is a portion that retains at least one function (e.g. completely, partially, minimally) of the parent polypeptide (e.g., a "minimal" or "core" domain). In some embodiments, the variant polypeptide retains enzymatic activity at least as active as the parent polypeptide. Accordingly, in some embodiments, a variant polypeptide has enzymatic activity greater than the parent polypeptide.

In some embodiments, the variant polypeptide has reduced nuclease activity or is a nuclease dead polypeptide. As used herein, catalytic residues of a polypeptide disclosed herein comprise D345, E506, and D594. In some embodiments, a variant polypeptide comprising a substitution at D345 and/or E506 and/or D594 (e.g., D345A and/or E506A and/or D594A) exhibits reduced nuclease activity or no nuclease activity relative to a parent polypeptide. In some embodiments, residue R593 contributes to nuclease activity. In some embodiments, a substitution at R593 alters nuclease activity, e.g., results in reduced nuclease activity.

In some embodiments, the variant polypeptide of the present disclosure has enzymatic activity equivalent to or greater than the parent polypeptide. In some embodiments, the variant polypeptide of the present disclosure has enzymatic activity at a temperature range from about 20° C. to about 90° C. In some embodiments, the variant polypeptide of the present disclosure has enzymatic activity at a temperature of about 20° C. to about 25° C. or at a temperature of about 37° C.

In some embodiments, the variant polypeptide comprises at least one alteration that enhances affinity to RNA (e.g., RNA affinity), as compared to a parent polypeptide. In some embodiments, the variant polypeptide exhibits enhanced RNA affinity, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant polypeptide exhibits enhanced RNA affinity, as compared to a parent polypeptide, in a buffer having a pH in a range of about 7.3 to about 8.6. In some embodiments, the variant polypeptide exhibits enhanced RNA affinity, as compared to a parent polypeptide, when the Tm value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent polypeptide. In one embodiment, the variant polypeptide exhibits enhanced RNA affinity when the Tm value of the variant polypeptide is at least 8° C. greater than the Tm value of the parent polypeptide.

In some embodiments, the variant polypeptide comprises at least one alteration that enhances complex formation with an RNA guide (e.g., binary complex formation), as compared to a parent polypeptide. In some embodiments, the variant polypeptide exhibits enhanced binary complex formation, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant polypeptide exhibits enhanced binary complex formation, as compared to a parent polypeptide, in a buffer having a pH in a range of about 7.3 to about 8.6. In some embodiments, the variant polypeptide exhibits enhanced binary complex formation, as compared to a parent polypeptide, when the Tm value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent polypeptide. In one embodiment, the variant polypeptide exhibits enhanced binary complex formation when the Tm value of the variant polypeptide is at least 8° C. greater than the Tm value of the parent polypeptide.

In some embodiments, the variant polypeptide comprises at least one alteration that enhances binding activity to an RNA guide, as compared to a parent polypeptide. In some embodiments, the variant polypeptide exhibits enhanced RNA guide binding activity, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant polypeptide exhibits enhanced RNA guide binding activity, as compared to a parent polypeptide, in a buffer having a pH in a range of about 7.3 to about 8.6. In some embodiments, the variant polypeptide exhibits enhanced RNA guide binding activity, as compared to a parent polypeptide, when the Tm value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent polypeptide. In one embodiment, the variant polypeptide exhibits enhanced RNA guide binding activity when the Tm value of the variant polypeptide is at least 8° C. greater than the Tm value of the parent polypeptide.

In some embodiments, the variant polypeptide comprises at least one alteration that enhances binding specificity to an RNA guide, as compared to a parent polypeptide. In some embodiments, the variant polypeptide exhibits enhanced RNA guide binding specificity, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant polypeptide exhibits enhanced RNA guide binding specificity, as compared to a parent polypeptide, in a buffer having a pH in a range of about 7.3 to about 8.6. In some embodiments, the variant polypeptide exhibits enhanced RNA guide binding specificity, as compared to a parent polypeptide, when the Tm value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent polypeptide. In one embodiment, the variant polypeptide exhibits enhanced RNA guide binding specificity when the Tm value of the variant polypeptide is at least 8° C. greater than the Tm value of the parent polypeptide.

In some embodiments, the variant polypeptide comprises at least one alteration that enhances protein-RNA interactions, as compared to a parent polypeptide. In some embodiments, the variant polypeptide exhibits enhanced protein-RNA interactions, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant polypeptide exhibits enhanced protein-RNA interactions, as compared to a parent polypeptide, in a buffer having a pH in a range of about 7.3 to about 8.6. In some embodiments, the variant polypeptide exhibits enhanced protein-RNA interactions, as compared to a parent polypeptide, when the Tm value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent polypeptide. In one embodiment, the variant polypeptide exhibits enhanced protein-RNA interactions when the Tm value of the variant polypeptide is at least 8° C. greater than the Tm value of the parent polypeptide.

In some embodiments, the variant polypeptide comprises at least one alteration that enhances protein stability, as compared to a parent polypeptide. In some embodiments, the variant polypeptide exhibits enhanced protein stability, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant polypeptide exhibits enhanced protein stability, as compared to a parent polypeptide, in a buffer having a pH in a range of about 7.3 to about 8.6. In some embodiments, the variant polypeptide exhibits enhanced protein stability, as compared to a parent polypeptide, when the Tm value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent polypeptide. In one embodiment, the variant polypeptide exhibits enhanced protein stability when the Tm value of the variant polypeptide is at least 8° C. greater than the Tm value of the parent polypeptide.

In some embodiments, the variant polypeptide comprises at least one alteration that decreases dissociation from an RNA guide (e.g., binary complex dissociation), as compared to a parent polypeptide. In some embodiments, the variant polypeptide exhibits decreased dissociation from an RNA guide, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant polypeptide exhibits decreased dissociation from an RNA guide, as compared to a parent polypeptide, in a buffer having a pH in a range of about 7.3 to about 8.6. In some embodiments, the variant polypeptide exhibits decreased dissociation from an RNA guide, as compared to a parent polypeptide, when the Tm value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent polypeptide. In one embodiment, the variant polypeptide exhibits decreased dissociation from an RNA guide when the Tm value of the variant polypeptide is at least 8° C. greater than the Tm value of the parent polypeptide. In some embodiments, the variant polypeptide exhibits decreased dissociation from an RNA guide, as compared to a parent polypeptide, over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours. In some embodiments, a variant CRISPR nuclease ribonucleoprotein (RNP) complex does not exchange the RNA guide with a different RNA.

In some embodiments, the variant polypeptide comprises at least one alteration that enhances ternary complex formation with an RNA guide and a target nucleic acid, as compared to a parent polypeptide. In some embodiments, the variant polypeptide exhibits enhanced ternary complex formation, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant polypeptide exhibits enhanced ternary complex formation, as compared to a parent polypeptide, in a buffer having a pH in a range of about 7.3 to about 8.6. In some embodiments, the variant polypeptide exhibits enhanced ternary complex formation, as compared to a parent polypeptide, when the Tm value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent polypeptide. In one embodiment, the variant polypeptide exhibits enhanced ternary complex formation when the Tm value of the variant polypeptide is at least 8° C. greater than the Tm value of the parent polypeptide.

In some embodiments, the variant polypeptide comprises at least one alteration such that a binary complex comprising the variant polypeptide (e.g., a variant binary complex) exhibits enhanced binding affinity to a target nucleic acid, as compared to a parent binary complex. In some embodiments, the variant binary complex exhibits enhanced binding affinity to a target nucleic acid, as compared to a parent binary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant binary complex exhibits enhanced binding affinity to a target nucleic acid, as compared to a parent binary complex, in a buffer having a pH in a range of about 7.3 to about 8.6. In some embodiments, the variant binary complex exhibits enhanced binding affinity to a target nucleic acid, as compared to a parent binary complex, when the Tm value of the variant binary complex is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent binary complex. In one embodiment, the variant binary complex exhibits enhanced binding affinity to a target nucleic acid when the Tm value of the variant binary complex is at least 8° C. greater than the Tm value of the parent binary complex.

In some embodiments, the variant polypeptide comprises at least one alteration such that a binary complex comprising the variant polypeptide (e.g., a variant binary complex) exhibits enhanced on-target binding activity, as compared to a parent binary complex. In some embodiments, the variant binary complex exhibits enhanced on-target binding activity, as compared to a parent binary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant binary complex exhibits enhanced on-target binding activity, as compared to a parent binary complex, in a buffer having a pH in a range of about 7.3 to about 8.6. In some embodiments, the variant binary complex exhibits enhanced on-target binding activity, as compared to a parent binary complex, when the Tm value of the variant binary complex is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent binary complex. In one embodiment, the variant binary complex exhibits enhanced on-target binding activity when the Tm value of the variant binary complex is at least 8° C. greater than the Tm value of the parent binary complex.

In some embodiments, the variant polypeptide comprises at least one alteration such that a binary complex comprising the variant polypeptide (e.g., a variant binary complex) exhibits enhanced on-target binding specificity, as compared to a parent binary complex. In some embodiments, the variant binary complex exhibits enhanced on-target binding specificity, as compared to a parent binary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant binary complex exhibits enhanced on-target binding specificity, as compared to a parent binary complex, in a buffer having a pH in a range of about 7.3 to about 8.6. In some embodiments, the variant binary complex exhibits enhanced on-target binding specificity, as compared to a parent binary complex, when the Tm value of the variant binary complex is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent binary complex. In one embodiment, the variant binary complex exhibits enhanced on-target binding specificity when the Tm value of the variant binary complex is at least 8° C. greater than the Tm value of the parent binary complex.

In some embodiments, the variant polypeptide comprises at least one alteration such that a binary complex comprising the variant polypeptide (e.g., a variant binary complex) exhibits decreased off-target binding to a non-target nucleic acid, as compared to a parent binary complex. In some embodiments, the variant binary complex exhibits decreased off-target binding to a non-target nucleic acid, as compared to a parent binary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant binary complex exhibits decreased off-target binding to a non-target nucleic acid, as compared to a parent binary complex, in a buffer having a pH in a range of about 7.3 to about 8.6. In some embodiments, the variant binary complex exhibits decreased off-target binding to a non-target nucleic acid, as compared to a parent binary complex, when the Tm value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent polypeptide. In one embodiment, the variant binary complex exhibits decreased off-target binding to a non-target nucleic acid when the Tm value of the variant binary complex is at least 8° C. greater than the Tm value of the parent polypeptide.

In some embodiments, the variant polypeptide comprises at least one alteration such that a binary complex comprising the variant polypeptide (e.g., a variant binary complex) exhibits decreased dissociation from the target nucleic acid, as compared to a parent binary complex. In some embodiments, the variant binary complex exhibits decreased dissociation from the target nucleic acid, as compared to a parent binary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant binary complex exhibits decreased dissociation from the target nucleic acid, as compared to a parent binary complex, in a buffer having a pH in a range of about 7.3 to about 8.6. In some embodiments, the variant binary complex exhibits decreased dissociation from the target nucleic acid, as compared to a parent binary complex, when the Tm value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent polypeptide. In one embodiment, the variant binary complex exhibits decreased dissociation from the target nucleic acid when the Tm value of the variant binary complex is at least 8° C. greater than the Tm value of the parent polypeptide.

In some embodiments, the variant polypeptide comprises at least one alteration such that a ternary complex comprising the variant polypeptide (e.g., a variant ternary complex) exhibits enhanced stability, as compared to a parent ternary complex. In some embodiments, the variant ternary complex exhibits enhanced stability, as compared to a parent ternary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant ternary complex exhibits enhanced stability, as compared to a parent ternary complex, in a buffer having a pH in a range of about 7.3 to about 8.6. In some embodiments, the variant ternary complex exhibits enhanced stability, as compared to a parent ternary complex, when the Tm value of the variant ternary complex is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent ternary complex. In one embodiment, the variant ternary complex exhibits enhanced stability when the Tm value of the variant ternary complex is at least 8° C. greater than the Tm value of the parent ternary complex.

Although the changes described herein may be one or more amino acid changes, changes to the variant polypeptide may also be of a substantive nature, such as fusion of polypeptides as amino- and/or carboxyl-terminal extensions. For example, variant polypeptide may contain additional peptides, e.g., one or more peptides. Examples of additional peptides may include epitope peptides for labelling, such as a polyhistidine tag (His-tag), Myc, and FLAG. In some embodiments, the variant polypeptide described herein can be fused to a detectable moiety such as a fluorescent protein (e.g., green fluorescent protein (GFP) or yellow fluorescent protein (YFP)).

In some embodiments, the variant polypeptide comprises at least one (e.g., two, three, four, five, six, or more) nuclear localization signal (NLS). In some embodiments, the variant polypeptide comprises at least one (e.g., two, three, four, five, six, or more) nuclear export signal (NES). In some embodiments, the variant polypeptide comprises at least one (e.g., two, three, four, five, six, or more) NLS and at least one (e.g., two, three, four, five, six, or more) NES.

In some embodiments, the variant polypeptide described herein can be self-inactivating. See, Epstein et al., "Engineering a Self-Inactivating CRISPR System for AAV Vectors," Mol. Ther., 24 (2016): S50, which is incorporated by reference in its entirety.

In some embodiments, the nucleotide sequence encoding the variant polypeptide described herein can be codon-optimized for use in a particular host cell or organism. For example, the nucleic acid can be codon-optimized for any non-human eukaryote including mice, rats, rabbits, dogs, livestock, or non-human primates. Codon usage tables are readily available, for example, at the "Codon Usage Database" available at world wide web address: kasuza.orjp/codon and these tables can be adapted in a number of ways. See Nakamura et al. *Nucl. Acids Res.* 28:292 (2000), which is incorporated herein by reference in its entirety. Computer algorithms for codon optimizing a particular sequence for expression in a particular host cell are also available, such as Gene Forge (Aptagen; Jacobus, PA).

RNA Guide

In some embodiments, a composition or complex as described herein comprises a targeting moiety (e.g., an RNA guide, antisense, oligonucleotides, peptide oligonucleotide conjugates) that binds the target nucleic acid and interacts with the variant polypeptide. The targeting moiety may bind a target nucleic acid (e.g., with specific binding affinity to the target nucleic acid).

In some embodiments, the targeting moiety comprises, or is, an RNA guide. In some embodiments, the RNA guide directs the variant polypeptide described herein to a particular nucleic acid sequence. Those skilled in the art reading the below examples of particular kinds of RNA guides will understand that, in some embodiments, an RNA guide is site-specific. That is, in some embodiments, an RNA guide associates specifically with one or more target nucleic acid sequences (e.g., specific DNA or genomic DNA sequences) and not to non-targeted nucleic acid sequences (e.g., non-specific DNA or random sequences).

In some embodiments, the composition as described herein comprises an RNA guide that associates with the variant polypeptide described herein and directs the variant polypeptide to a target nucleic acid sequence (e.g., DNA). In some embodiments, the RNA guide can associate with a polypeptide described herein (e.g., a polypeptide of having an amino acid sequence of SEQ ID NO: 3, or a variant thereof). In some embodiments, the RNA guide directs the polypeptide to a target nucleic acid sequence (e.g., DNA).

The RNA guide may target (e.g., associate with, be directed to, contact, or bind) one or more nucleotides of a target sequence, e.g., a site-specific sequence or a site-specific target. In some embodiments, the variant ribonucleoprotein (e.g., variant CRISPR nuclease polypeptide plus an RNA guide) is activated upon binding to a target nucleic acid that is complementary to a DNA-targeting sequence in the RNA guide (e.g., a sequence-specific substrate or target nucleic acid).

In some embodiments, a spacer or spacer sequence is a portion in an RNA guide that is the RNA equivalent of the target sequence (a DNA sequence). Typically, the spacer contains a sequence capable of binding to the non-PAM strand via base-pairing at the site complementary to the target sequence (in the PAM strand). In some instances, the spacer may be at least 75% identical to the target sequence (e.g., at least 80%, at least 85%, at least 90%, at least 95%, at least 98%, or at least 99%), when considering T to be equivalent to U for the purpose of this comparison. In some instances, the spacer may be 100% identical to the target sequence when considering T to be equivalent to U for the purpose of this comparison.

In some instances, a polynucleotide is complementary to another when a first polynucleotide (e.g., a spacer sequence of an RNA guide) has a certain level of complementarity to a second polynucleotide (e.g., the complementary sequence of a target sequence) such that the first and second polynucleotides can form a double-stranded complex via base-pairing to permit an effector polypeptide that is complexed with the first polynucleotide to act on (e.g., cleave) the second polynucleotide. In some embodiments, the first polynucleotide may be substantially complementary to the second polynucleotide. In some embodiments, the first polynucleotide has at least about 80%, 81%, 82%, 83%, 84%, 85%, 86%, 87%, 88%, 89%, 90%, 91%, 92%, 93%, 94%, 95%, 96%, 97%, 98%, or 99% complementarity to the second polynucleotide. In some embodiments, the first polynucleotide is completely complementary to the second polynucleotide, i.e., having 100% complementarity to the second polynucleotide.

In some embodiments, an RNA guide comprises a spacer having a length of from about 11 nucleotides to about 100 nucleotides. For example, the DNA-targeting segment can have a length of from about 11 nucleotides to about 80 nucleotides, from about 11 nucleotides to about 50 nucleotides, from about 11 nucleotides to about 40 nucleotides, from about 11 nucleotides to about 30 nucleotides, from about 11 nucleotides to about 25 nucleotides, from about 11 nucleotides to about 20 nucleotides, or from about 11 nucleotides to about 19 nucleotides. For example, the spacer can have a length of from about 19 nucleotides to about 20 nucleotides, from about 19 nucleotides to about 25 nucleotides, from about 19 nucleotides to about 30 nucleotides, from about 19 nucleotides to about 35 nucleotides, from about 19 nucleotides to about 40 nucleotides, from about 19 nucleotides to about 45 nucleotides, from about 19 nucleotides to about 50 nucleotides, from about 19 nucleotides to about 60 nucleotides, from about 19 nucleotides to about 70 nucleotides, from about 19 nucleotides to about 80 nucleotides, from about 19 nucleotides to about 90 nucleotides, from about 19 nucleotides to about 100 nucleotides, from about 20 nucleotides to about 25 nucleotides, from about 20 nucleotides to about 30 nucleotides, from about 20 nucleotides to about 35 nucleotides, from about 20 nucleotides to about 40 nucleotides, from about 20 nucleotides to about 45 nucleotides, from about 20 nucleotides to about 50 nucleotides, from about 20 nucleotides to about 60 nucleotides, from about 20 nucleotides to about 70 nucleotides, from about 20 nucleotides to about 80 nucleotides, from about 20 nucleotides to about 90 nucleotides, or from about 20 nucleotides to about 100 nucleotides.

In some embodiments, the spacer of the RNA guide may be generally designed to have a length of between 11 and 50 nucleotides (e.g., 11, 12, 13, 14, 15, 16, 17, 18, 19, 20, 21, 22, 23, 24, 25, 26, 27, 28, 29, 30, 31, 32, 33, 34, or 35 nucleotides) and be complementary to a specific target nucleic acid sequence. In some particular embodiments, the RNA guide may be designed to be complementary to a specific DNA strand, e.g., of a genomic locus. In some embodiments, the DNA targeting sequence is designed to be complementary to a specific DNA strand, e.g., of a genomic locus.

The RNA guide may be substantially identical to a complementary strand of a reference nucleic acid sequence. In some embodiments, the RNA guide comprises a sequence having least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to a complementary strand of a reference nucleic acid sequence, e.g., target nucleic acid. The percent identity between two such nucleic acids can be determined manually by inspection of the two optimally aligned nucleic acid sequences or by using software programs or algorithms (e.g., BLAST, ALIGN, CLUSTAL) using standard parameters.

In some embodiments, the RNA guide has at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to a complementary strand of a target nucleic acid.

In some embodiments, the RNA guide comprises a spacer that is a length of between 11 and 50 nucleotides (e.g., 11, 12, 13, 14, 15, 16, 17, 18, 19, 20, 21, 22, 23, 24, 25, 26, 27, 28, 29, 30, 31, 32, 33, 34, or 35 nucleotides) and at least 80%, at least 90%, at least 95%, at least 96%, at least 97%, at least 98%, at least 99% complementary to a target nucleic acid. In some embodiments, the RNA guide comprises a sequence at least 80%, at least 90%, at least 95%, at least 96%, at least 97%, at least 98%, at least 99% complementary to a target DNA sequence. In some embodiments, the RNA guide comprises a sequence at least 80%, at least 90%, at least 95%, at least 96%, at least 97%, at least 98%, at least 99% complementary to a target genomic sequence. In some embodiments, the RNA guide comprises a sequence, e.g., RNA sequence, that is a length of up to 50 and at least 80%, at least 90%, at least 95%, at least 96%, at least 97%, at least 98%, at least 99% complementary to a target nucleic acid. In some embodiments, the RNA guide comprises a sequence at least 80%, at least 90%, at least 95%, at least 96%, at least 97%, at least 98%, at least 99% complementary to a target DNA sequence. In some embodiments, the RNA guide comprises a sequence at least 80%, at least 90%, at least 95%, at least 96%, at least 97%, at least 98%, at least 99% complementary to a target genomic sequence.

In certain embodiments, the RNA guide includes, consists essentially of, or comprises a direct repeat sequence linked to a DNA targeting sequence. In some embodiments, the RNA guide includes a direct repeat sequence and a DNA targeting sequence or a direct repeat-DNA targeting sequence-direct repeat sequence. In some embodiments, the RNA guide includes a truncated direct repeat sequence and a DNA targeting sequence, which is typical of processed or mature crRNA. In some embodiments, the variant polypeptide described herein forms a complex with the RNA guide, and the RNA guide directs the complex to associate with site-specific target nucleic acid that is complementary to at least a portion of the RNA guide.

In some embodiments, the direct repeat sequence is at least 90% identical to a sequence set forth in Table 3 or a portion of a sequence set forth in Table 3. In some embodiments, the direct repeat sequence is at least 95% (e.g., at least 97%, at least 99%, or at least 100%) identical to a sequence set forth in Table 3 or a portion of a sequence set forth in Table 3. In some embodiments, the direct repeat sequence is identical to a sequence set forth in Table 3 or a portion of a sequence set forth in Table 3. In some embodiments, the direct repeat sequence comprises the nucleotide sequence set forth in any one of SEQ ID NOs: 4-6.

TABLE 3

Direct repeat sequences.

| Sequence identifier | Direct Repeat Sequence |
|---|---|
| SEQ ID NO: 4 | CUCGCGGUCCCAUCGGAACGGGUUGUGGUUCCGAC |
| SEQ ID NO: 5 | CUCGCGGUCCCAUCGGAACGGGUUUGUGGUUCCGAC |
| SEQ ID NO: 6 | GGUCCCAUCGGAACGGGUUGUGGUUCCGAC |

In some embodiments, the direct repeat sequence comprises a sequence having at least 90% identity to UGUGGUUCCGAC (SEQ ID NO: 7). In some embodiments, the direct repeat sequence comprises the sequence set forth in SEQ ID NO: 7.

In some embodiments, PAMs corresponding to a variant polypeptide of the present disclosure include 5'-NTN-3', 5'-HTN-3', or 5'-TNA-3'. As used herein, N's can each be any nucleotide (e.g., A, G, T, or C) or a subset thereof (e.g., R (A or G), Y (C or T), K (G or T), B (G, T, or C), H (A, C, or T). In some embodiments, the PAM comprises 5'-CTG-3'. In some embodiments, the PAM comprises 5'-CTC-3'. In some embodiments, a binary complex comprising a variant polypeptide of the present disclosure binds to a target nucleic acid adjacent to a 5'-NTN-3', 5'-HTN-3', or 5'-TNA-3' sequence. In some embodiments, a binary complex comprising a variant polypeptide of the present disclosure binds to a target nucleic acid adjacent to a 5'-CTG-3' or 5'-CTC-3' sequence.

In some embodiments, the composition or complex described herein includes one or more (e.g., two, three, four, five, six, seven, eight, or more) RNA guides, e.g., a plurality of RNA guides.

In some embodiments, the RNA guide has an architecture similar to, for example, RNA guides of International Publication Nos. WO 2014/093622 and WO 2015/070083, the entire contents of each of which are incorporated herein by reference.

Unless otherwise noted, all compositions and complexes and polypeptides provided herein are made in reference to the active level of that composition or complex or polypeptide, and are exclusive of impurities, for example, residual solvents or by-products, which may be present in commercially available sources. Enzymatic component weights are based on total active protein. All percentages and ratios are calculated by weight unless otherwise indicated. All percentages and ratios are calculated based on the total composition unless otherwise indicated. In the exemplified composition, the enzymatic levels are expressed by pure enzyme by weight of the total composition and unless otherwise specified, the ingredients are expressed by weight of the total compositions.

Modifications

The RNA guide or any of the nucleic acid sequences encoding the variant polypeptides may include one or more covalent modifications with respect to a reference sequence, in particular the parent polyribonucleotide, which are included within the scope of this disclosure.

Exemplary modifications can include any modification to the sugar, the nucleobase, the internucleoside linkage (e.g. to a linking phosphate/to a phosphodiester linkage/to the phosphodiester backbone), and any combination thereof. Some of the exemplary modifications provided herein are described in detail below.

The RNA guide or any of the nucleic acid sequences encoding components of the variant polypeptides may include any useful modification, such as to the sugar, the nucleobase, or the internucleoside linkage (e.g. to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

In some embodiments, the modification may include a chemical or cellular induced modification. For example, some nonlimiting examples of intracellular RNA modifications are described by Lewis and Pan in "RNA modifications and structures cooperate to guide RNA-protein interactions" from Nat Reviews Mol Cell Biol, 2017, 18:202-210.

Different sugar modifications, nucleotide modifications, and/or internucleoside linkages (e.g., backbone structures) may exist at various positions in the sequence. One of ordinary skill in the art will appreciate that the nucleotide analogs or other modification(s) may be located at any position(s) of the sequence, such that the function of the sequence is not substantially decreased. The sequence may include from about 1% to about 100% modified nucleotides (either in relation to overall nucleotide content, or in relation to one or more types of nucleotide, i.e. any one or more of A, G, U or C) or any intervening percentage (e.g., from 1% to 20%>, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, sugar modifications (e.g., at the 2' position or 4' position) or replacement of the sugar at one or more ribonucleotides of the sequence may, as well as backbone modifications, include modification or replacement of the phosphodiester linkages. Specific examples of a sequence include, but are not limited to, sequences including modified backbones or no natural internucleoside linkages such as internucleoside modifications, including modification or replacement of the phosphodiester linkages. Sequences having modified backbones include, among others, those that do not have a phosphorus atom in the backbone. For the purposes of this application, and as sometimes referenced in the art, modified RNAs that do not have a phosphorus atom in their internucleoside backbone can also be considered to be oligonucleosides. In particular embodiments, a sequence will include ribonucleotides with a phosphorus atom in its internucleoside backbone.

Modified sequence backbones may include, for example, phosphorothioates, chiral phosphorothioates, phosphorodithioates, phosphotriesters, aminoalkylphosphotriesters, methyl and other alkyl phosphonates such as 3'-alkylene phosphonates and chiral phosphonates, phosphinates, phosphoramidates such as 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments, the sequence may be negatively or positively charged.

The modified nucleotides, which may be incorporated into the sequence, can be modified on the internucleoside linkage (e.g., phosphate backbone). Herein, in the context of the polynucleotide backbone, the phrases "phosphate" and "phosphodiester" are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage as described herein. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The a-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment.

In specific embodiments, a modified nucleoside includes an alpha-thio-nucleoside (e.g., 5'-O-(1-thiophosphate)-adenosine, 5'-O-(1-thiophosphate)-cytidine (a-thio-cytidine), 5'-O-(1-thiophosphate)-guanosine, 5'-O-(1-thiophosphate)-uridine, or 5'-O-(1-thiophosphate)-pseudouridine).

Other internucleoside linkages that may be employed according to the present disclosure, including internucleoside linkages which do not contain a phosphorous atom, are described herein.

In some embodiments, the sequence may include one or more cytotoxic nucleosides. For example, cytotoxic nucleosides may be incorporated into sequence, such as bifunctional modification. Cytotoxic nucleoside may include, but are not limited to, adenosine arabinoside, 5-azacytidine, 4'-thio-aracytidine, cyclopentenylcytosine, cladribine, clofarabine, cytarabine, cytosine arabinoside, 1-(2-C-cyano-2-deoxy-beta-D-arabino-pentofuranosyl)-cytosine, decitabine, 5-fluorouracil, fludarabine, floxuridine, gemcitabine, a combination of tegafur and uracil, tegafur ((RS)-5-fluoro-1-(tetrahydrofuran-2-yl)pyrimidine-2,4(1H,3H)-dione), troxacitabine, tezacitabine, 2'-deoxy-2'-methylidenecytidine (DMDC), and 6-mercaptopurine. Additional examples include fludarabine phosphate, N4-behenoyl-1-beta-D-arabinofuranosylcytosine, N4-octadecyl-1-beta-D-arabinofuranosylcytosine, N4-palmitoyl-1-(2-C-cyano-2-deoxy-beta-D-arabino-pentofuranosyl) cytosine, and P-4055 (cytarabine 5'-elaidic acid ester).

In some embodiments, the sequence includes one or more post-transcriptional modifications (e.g., capping, cleavage, polyadenylation, splicing, poly-A sequence, methylation, acylation, phosphorylation, methylation of lysine and arginine residues, acetylation, and nitrosylation of thiol groups and tyrosine residues, etc.). The one or more post-transcriptional modifications can be any post-transcriptional modification, such as any of the more than one hundred different nucleoside modifications that have been identified in RNA (Rozenski, J, Crain, P, and McCloskey, J. (1999). The RNA Modification Database: 1999 update. Nucl Acids Res 27:196-197) In some embodiments, the first isolated nucleic acid comprises messenger RNA (mRNA). In some embodiments, the mRNA comprises at least one nucleoside selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In some embodiments, the mRNA comprises at least one nucleoside selected from the group consisting of 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine. In some embodiments, the mRNA comprises at least one nucleoside selected from the group consisting of 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl) adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthioadenine, and 2-methoxy-adenine. In some embodiments, mRNA comprises at least one nucleoside selected from the group consisting of inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

The sequence may or may not be uniformly modified along the entire length of the molecule. For example, one or more or all types of nucleotide (e.g., naturally-occurring nucleotides, purine or pyrimidine, or any one or more or all of A, G, U, C, I, pU) may or may not be uniformly modified in the sequence, or in a given predetermined sequence region thereof. In some embodiments, the sequence includes a pseudouridine. In some embodiments, the sequence includes an inosine, which may aid in the immune system characterizing the sequence as endogenous versus viral RNAs. The incorporation of inosine may also mediate improved RNA stability/reduced degradation. See for example, Yu, Z. et al. (2015) RNA editing by ADAR1 marks dsRNA as "self". Cell Res. 25, 1283-1284, which is incorporated by reference in its entirety.

Target Nucleic Acid

The methods disclosed herein are applicable for a variety of target nucleic acids. In some embodiments, the target nucleic acid is a DNA, such as a DNA locus. In some embodiments, the target nucleic acid is an RNA, such as an RNA locus or mRNA. In some embodiments, the target nucleic acid is single-stranded (e.g., single-stranded DNA). In some embodiments, the target nucleic acid is double-stranded (e.g., double-stranded DNA). In some embodiments, the target nucleic acid comprises both single-stranded and double-stranded regions. In some embodiments, the target nucleic acid is linear. In some embodiments, the target nucleic acid is circular. In some embodiments, the target nucleic acid comprises one or more modified nucleotides, such as methylated nucleotides, damaged nucleotides, or nucleotides analogs. In some embodiments, the target nucleic acid is not modified.

The target nucleic acid may be of any length, such as about at least any one of 100 bp, 200 bp, 500 bp, 1000 bp, 2000 bp, 5000 bp, 10 kb, 20 kb, 50 kb, 100 kb, 200 kb, 500 kb, 1 Mb, or longer. The target nucleic acid may also comprise any sequence. In some embodiments, the target nucleic acid is GC-rich, such as having at least about any one of 40%, 45%, 50%, 55%, 60%, 65%, or higher GC content. In some embodiments, the target nucleic acid has a GC content of at least about 70%, 80%, or more. In some embodiments, the target nucleic acid is a GC-rich fragment in a non-GC-rich target nucleic acid. In some embodiments, the target nucleic acid is not GC-rich. In some embodiments, the target nucleic acid has one or more secondary structures or higher-order structures. In some embodiments, the target nucleic acid is not in a condensed state, such as in a chromatin, to render the target nucleic acid inaccessible by the variant polypeptide/RNA guide complex.

In some embodiments, the target nucleic acid is present in a cell. In some embodiments, the target nucleic acid is present in the nucleus of the cell. In some embodiments, the target nucleic acid is endogenous to the cell. In some embodiments, the target nucleic acid is a genomic DNA. In some embodiments, the target nucleic acid is a chromosomal DNA. In one embodiment, the target nucleic acid is an extrachromosomal nucleic acid. In some embodiments, the target nucleic acid is a protein-coding gene or a functional region thereof, such as a coding region, or a regulatory element, such as a promoter, enhancer, a 5' or 3' untranslated region, etc. In some embodiments, the target nucleic acid is a non-coding gene, such as transposon, miRNA, tRNA, ribosomal RNA, ribozyme, or lincRNA. In some embodiments, the target nucleic acid is a plasmid.

In some embodiments, the target nucleic acid is exogenous to a cell. In some embodiments, the target nucleic acid is a viral nucleic acid, such as viral DNA or viral RNA. In some embodiments, the target nucleic acid is a horizontally transferred plasmid. In some embodiments, the target nucleic acid is integrated in the genome of the cell. In some embodiments, the target nucleic acid is not integrated in the genome of the cell. In some embodiments, the target nucleic acid is a plasmid in the cell. In some embodiments, the target nucleic acid is present in an extrachromosomal array.

In some embodiments, the target nucleic acid is an isolated nucleic acid, such as an isolated DNA or an isolated RNA. In some embodiments, the target nucleic acid is present in a cell-free environment. In some embodiments, the target nucleic acid is an isolated vector, such as a plasmid. In some embodiments, the target nucleic acid is an ultrapure plasmid.

The target nucleic acid is a segment of the target nucleic acid that hybridizes to the RNA guide. In some embodiments, the target nucleic acid has only one copy of the target nucleic acid. In some embodiments, the target nucleic acid has more than one copy, such as at least about any one of 2, 3, 4, 5, 10, 100, or more copies of the target nucleic acid. For example, a target nucleic acid comprising a repeated sequence in a genome of a viral nucleic acid or a bacterium may be targeted by the variant ribonucleoprotein.

In some embodiments, the target nucleic acid is present in a readily accessible region of the target nucleic acid. In some embodiments, the target nucleic acid is in an exon of a target gene. In some embodiments, the target nucleic acid is across an exon-intron junction of a target gene. In some embodiments, the target nucleic acid is present in a non-coding region, such as a regulatory region of a gene. In some embodiments, wherein the target nucleic acid is exogenous to a cell, the target nucleic acid comprises a sequence that is not found in the genome of the cell.

Suitable DNA/RNA binding conditions include physiological conditions normally present in a cell. Other suitable DNA/RNA binding conditions (e.g., conditions in a cell-free system) are known in the art; see, e.g., Sambrook, supra. The strand of the target nucleic acid that is complementary to and hybridizes with the RNA guide is referred to as the "complementary strand" and the strand of the target nucleic acid that is complementary to the "complementary strand" (and is therefore not complementary to the RNA guide) is referred to as the "noncomplementary strand" or "non-complementary strand".

In some embodiments, the target nucleic acid comprises a nucleotide sequence of any one of SEQ ID NOs: 8, 10, 12, 14, 16, 18, 20, and 22.

Binary Complex

A binary complex described herein, in some embodiments, comprises a variant polypeptide that associates with at least one RNA guide, wherein each RNA guide targets a target nucleic acid such as DNA. In some embodiments, the variant polypeptide/RNA guide complex (e.g., variant binary complex) comprises enzymatic activity, such as nuclease activity, that may nick or cleave the target nucleic acid. The variant polypeptide and the RNA guide, either alone or together, do not naturally occur. Complex formation between the variant polypeptide and the RNA guide can enhance stability and/or protein-RNA interactions between the two, as compared to a parent polypeptide and RNA guide.

Generally, the variant polypeptide and the targeting moiety (e.g., RNA guide) bind to each other in a molar ratio of about 1:1 to form the variant binary complex. Binding of the variant polypeptide and the targeting moiety (e.g., RNA guide) to form the variant binary complex is referred to as loading the RNA guide to the polypeptide.

In some embodiments, the binary complex follows a one-guide rule, i.e., the variant polypeptide does not dissociate from the bound RNA guide in the complex, or switch RNA guide with a free, unbound RNA. In some embodiments, the ternary complex follows a one-binary complex rule, i.e., the variant binary complex does not dissociate from the bound target nucleic acid (e.g., target DNA substrate) or switch the target nucleic acid with a free, unbound nucleic acid.

Functionality of Binary Complexes

In some aspects, the variant binary complex comprises a variant polypeptide with at least one alteration or mutation that enhances at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability.

In some aspects, the variant binary complex comprises a variant polypeptide with at least one alteration or mutation and the variant binary complex has decreased at least one of off-target binding to a non-target nucleic acid, activity at a non-target locus of a target nucleic acid, binary complex dissociation, dissociation from the target nucleic acid.

In some aspects, a variant polypeptide and a targeting moiety (e.g., RNA guide) form a variant binary complex, and the variant binary complex exhibits increased at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability, as compared to a parent binary complex.

In some embodiments, the variant binary complex comprises a variant polypeptide with at least one alteration or mutation that increases at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability of the variant binary complex at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% greater than the enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability of a parent binary complex.

In some embodiments, the variant binary complex exhibits enhanced at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability, as compared to a parent binary complex, at a temperature in the range of about 20° C. to about 65° C., e.g., about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C.

In some embodiments, the variant binary complex exhibits enhanced at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability, as compared to a parent binary complex, in a buffer having a pH in a range of about 7.3 to about 8.6 (e.g., 7.3, 7.4, 7.5, 7.6, 7.7, 7.8, 7.9, 8.0, 8.1, 8.2, 8.3, 8.4, 8.5, 8.6, or any value within a range between any combination of these values).

In some embodiments, the variant binary complex exhibits enhanced at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability, as compared to a parent binary complex, when the Tm value of the variant binary complex is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent binary complex. In one embodiment, the variant binary complex exhibits enhanced at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability when the Tm value of the variant binary complex is at least 8° C. greater than the Tm value of the parent binary complex.

In some embodiments, the variant binary complex exhibits increased at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability at about 37° C. over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours as compared to a parent binary complex. In some embodiments, a variant binary complex exhibits increased at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability over a range of incubation times as compared to a parent binary complex.

In some aspects, a variant polypeptide and a targeting moiety (e.g., RNA guide) form a variant binary complex, and the variant binary complex exhibits decreased at least one of off-target binding to a non-target nucleic acid, activity at a non-target locus of a target nucleic acid, binary complex dissociation, and/or dissociation from the target nucleic acid, as compared to a parent binary complex. In some embodiments, the variant binary complex exhibits decreased at least one of off-target binding to a non-target nucleic acid, activity at a non-target locus of a target nucleic acid, binary complex dissociation, and/or dissociation from the target nucleic acid may be at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% less than the off-target binding to a non-target nucleic acid, activity at a non-target locus of a target nucleic acid, binary complex dissociation, and/or dissociation from the target nucleic acid of a parent binary complex.

In some embodiments, the variant binary complex exhibits decreased at least one of off-target binding to a non-target nucleic acid, activity at a non-target locus of a target nucleic acid, binary complex dissociation, and/or dissociation from the target nucleic acid at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% less than the off-target binding to a non-target nucleic acid, activity at a non-target locus of a target nucleic acid, binary complex dissociation, and/or dissociation from the target nucleic acid of a parent binary complex.

In some embodiments, the variant binary complex exhibits decreased at least one of off-target binding to a non-target nucleic acid, activity at a non-target locus of a target nucleic acid, binary complex dissociation, and/or dissociation from the target nucleic acid, as compared to a parent binary complex, at a temperature in the range of about 20° C. to about 65° C., e.g., about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C.

In some embodiments, the variant binary complex exhibits decreased at least one of off-target binding to a non-target nucleic acid, activity at a non-target locus of a target nucleic acid, binary complex dissociation, and/or dissociation from the target nucleic acid, as compared to a parent binary complex, in a buffer having a pH in a range of about 7.3 to about 8.6 (e.g., 7.3, 7.4, 7.5, 7.6, 7.7, 7.8, 7.9, 8.0, 8.1, 8.2, 8.3, 8.4, 8.5, 8.6, or any value within a range between any combination of these values).

In some embodiments, the variant binary complex exhibits decreased at least one of off-target binding to a non-target nucleic acid, activity at a non-target locus of a target nucleic acid, binary complex dissociation, and/or dissociation from the target nucleic acid, as compared to a parent binary complex, when the Tm value of the variant binary complex is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent binary complex. In one embodiment, the variant binary complex exhibits at least one of decreased off-target binding to a non-target nucleic acid, activity at a non-target locus of a target nucleic acid, binary complex dissociation, and/or dissociation from the target nucleic acid when the Tm value of the variant binary complex is at least 8° C. greater than the Tm value of the parent binary complex.

In some embodiments, the variant binary complex exhibits decreased at least one of complex (variant binary complex or variant ternary complex) dissociation and/or dissociation from a target locus at about 37° C. over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours as compared to a complex formed by a parent polypeptide and RNA guide. In some embodiments, a variant binary complex exhibits decreased at least one of complex (variant binary complex or variant ternary complex) dissociation and/or dissociation from a target locus over a range of incubation times as compared to a complex formed by a parent polypeptide and RNA guide.

In some embodiments, the variant binary complex exhibits decreased at least one of complex (variant binary complex or variant ternary complex) dissociation and/or dissociation from a target locus at about 37° C. over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours as compared to a parent binary complex. In some embodiments, the variant binary complex exhibits decreased at least one of complex (variant binary complex or variant ternary complex) dissociation and/or dissociation from a target locus over a range of incubation times as compared to a parent binary complex.

Ternary Complex

A ternary complex described herein, in some embodiments, comprises a variant polypeptide that associates with at least one RNA guide (i.e., forms a variant binary complex), wherein each RNA guide targets and associates with a target nucleic acid such as DNA (i.e., forms a variant ternary complex). In some embodiments, the variant polypeptide/RNA guide complex (e.g., variant binary complex) comprises enzymatic activity, such as nuclease activity, that may nick or cleave the target nucleic acid of the variant ternary complex. In some embodiments, the variant ternary complex comprises enzymatic activity, such as nuclease activity. The variant polypeptide, the RNA guide, and the target nucleic acid, either alone or together, do not naturally occur.

Generally, the variant binary complex, e.g., the variant polypeptide and the targeting moiety, binds to a target nucleic acid in a molar ratio of about 1:1 to form the variant ternary complex. Binding of the variant binary complex to the target nucleic acid, e.g., target DNA substrate, to form the variant ternary complex is referred to as loading the variant binary complex to the target nucleic acid.

Generally, the variant polypeptide, the targeting moiety (e.g., RNA guide), and the target nucleic acid associate with each other in a molar ratio of about 1:1:1 to form the variant ternary complex.

In some embodiments, a target nucleic acid includes one or more target loci of a variant binary complex or plurality of variant binary complexes. In some embodiments, a target nucleic acid includes one or more non-target loci of a variant binary complex or plurality of variant binary complexes.

Functionality of Ternary Complexes

In some aspects, the variant ternary complex comprises a variant polypeptide with at least one alteration or mutation and the variant ternary complex has enhanced at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability.

In some aspects, the variant ternary complex comprises a variant polypeptide with at least one alteration or mutation and the variant ternary complex has decreased at least one of dissociation from a target locus, off-target binding to a non-target nucleic acid, activity at a non-target locus of a target nucleic acid, and/or ternary complex dissociation.

In some aspects, a variant binary complex and a target nucleic acid (e.g., DNA) form a variant ternary complex, and the variant ternary complex exhibits increased at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability, as compared to a parent binary complex.

In some embodiments, the variant ternary complex exhibits at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability of the variant ternary complex at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% greater than the enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability of a parent binary complex.

In some embodiments, the variant ternary complex exhibits enhanced at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability, as compared to a parent ternary complex, at a temperature in the range of about 20° C. to about 65° C., e.g., about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C.

In some embodiments, the variant ternary complex exhibits enhanced at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability, as compared to a parent ternary complex, in a buffer having a pH in a range of about 7.3 to about 8.6 (e.g., 7.3, 7.4, 7.5, 7.6, 7.7, 7.8, 7.9, 8.0, 8.1, 8.2, 8.3, 8.4, 8.5, 8.6, or any value within a range between any combination of these values).

In some embodiments, the variant ternary complex exhibits enhanced at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability, as compared to a parent ternary complex, when the Tm value of the variant ternary complex is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of a parent ternary complex. In one embodiment, the variant ternary complex exhibits enhanced at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability when the Tm value of the variant ternary complex is at least 8° C. greater than the Tm value of the parent ternary complex.

In some embodiments, the variant ternary complex exhibits increased at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability at about 37° C. over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours as compared to a parent ternary complex. In some embodiments, a variant ternary complex exhibits increased at least one of enzymatic activity, target nucleic acid complex formation, target nucleic acid binding activity, target nucleic acid affinity, target nucleic acid binding specificity, protein-nucleic acid interactions, ternary complex formation, on-target binding activity, on-target binding specificity, and/or stability over a range of incubation times as compared to a parent ternary complex.

In some aspects, a variant binary complex and a target nucleic acid (e.g., DNA) form a variant ternary complex, and the variant ternary complex exhibits decreased at least one of dissociation from a target locus, off-target binding to a non-target nucleic acid, activity at a non-target locus of a target nucleic acid, and/or ternary complex dissociation, as compared to a parent binary complex.

In some embodiments, the variant ternary complex exhibits decreased at least one of dissociation from a target locus, off-target binding to a non-target nucleic acid, activity at a non-target locus of a target nucleic acid, and/or ternary complex dissociation of the variant ternary complex may be at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% less than the dissociation from a target locus, off-target binding to a non-target nucleic acid, activity at a non-target locus of a target nucleic acid, and/or ternary complex dissociation of a parent binary complex.

In some embodiments, the variant ternary complex exhibits decreased at least one of dissociation from a target locus, off-target binding to a non-target nucleic acid, activity at a non-target locus of a target nucleic acid, and/or ternary complex dissociation at a temperature of about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. as compared to a parent ternary complex.

In some embodiments, the variant ternary complex exhibits decreased at least one of dissociation from a target locus, off-target binding to a non-target nucleic acid, activity at a non-target locus of a target nucleic acid, and/or ternary complex dissociation over a range of temperatures, from about 20° C. to about 65° C. as compared to a parent ternary complex. In some embodiments, the variant ternary complex exhibits decreased at least one of dissociation from a target locus, off-target binding to a non-target nucleic acid, activity at a non-target locus of a target nucleic acid, and/or ternary complex dissociation at about 37° C. over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours as compared to a parent ternary complex. In some embodiments, the variant ternary complex exhibits decreased at least one of dissociation from a target locus, off-target binding to a non-target nucleic acid, activity at a non-target locus of a target nucleic acid, and/or ternary complex dissociation over a range of incubation times as compared to a parent ternary complex.

In some embodiments, the variant ternary complex exhibits decreased at least one of dissociation from a target locus, off-target binding to a non-target nucleic acid, activity at a non-target locus of a target nucleic acid, and/or ternary complex dissociation in a buffer having a pH in a range of about 7.3 to about 8.6 than a parent ternary complex. In one embodiment, the variant ternary complex exhibits decreased at least one of dissociation from a target locus, off-target binding to a non-target nucleic acid, activity at a non-target locus of a target nucleic acid, and/or ternary complex dissociation in a pH of about 7.3, 7.4, 7.5, 7.6, 7.7, 7.8, 7.9, 8.0, 8.1, 8.2, 8.3, 8.4, 8.5, or 8.6 than a parent ternary complex.

In some embodiments, the variant ternary complex exhibits decreased at least one of dissociation from a target locus, off-target binding to a non-target nucleic acid, activity at a non-target locus of a target nucleic acid, and/or ternary complex dissociation when a Tm value of the variant ternary complex is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the Tm value of the reference molecule or Tm of a reference value, e.g., of Tm of a parent ternary complex. In one embodiment, the variant ternary complex exhibits decreased at least one of dissociation from a target locus, off-target binding to a non-target nucleic acid, activity at a non-target locus of a target nucleic acid, and/or ternary complex dissociation when a Tm value of the variant ternary complex is at least 8° C. greater than the Tm value of the reference molecule or Tm of a reference value, e.g., Tm of a parent ternary complex.

In some embodiments, the variant ternary complex exhibits increased stability at about 37° C. over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours as compared to a parent ternary complex. In some embodiments, a variant ternary complex exhibits increased stability over a range of incubation times as compared to a parent ternary complex.

In some aspects, a variant binary complex exhibits decreased activity at a non-target locus of a target nucleic acid as compared to a parent binary complex. In some embodiments, non-target activity is assessed at a PAM-adjacent sequence of a particular Levenshtein distance (e.g., an edit distance of 1, 2, 3, or 4) from an on-target locus sequence. In some embodiments, activity at a non-target locus by a variant binary complex may be at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% less than activity at the non-target locus by a parent binary complex.

Preparation

In some embodiments, the variant polypeptide of the present disclosure can be prepared by (a) culturing bacteria which produce the variant polypeptide of the present disclosure, isolating the variant polypeptide, optionally, purifying the variant polypeptide, and complexing the variant polypeptide with RNA guide. The variant polypeptide can be also prepared by (b) a known genetic engineering technique, specifically, by isolating a gene encoding the variant polypeptide of the present disclosure from bacteria, constructing a recombinant expression vector, and then transferring the vector into an appropriate host cell that expresses the RNA guide for expression of a recombinant protein that complexes with the RNA guide in the host cell. Alternatively, the variant polypeptide can be prepared by (c) an in vitro coupled transcription-translation system and then complexes with RNA guide. Bacteria that can be used for preparation of the variant polypeptide of the present disclosure are not particularly limited as long as they can produce the variant polypeptide of the present disclosure. Some nonlimiting examples of the bacteria include E. coli cells described herein.

Vectors

The present disclosure provides a vector for expressing the variant polypeptide described herein or nucleic acids encoding the variant polypeptide described herein may be incorporated into a vector. In some embodiments, a vector of the disclosure includes a nucleotide sequence encoding the variant polypeptide.

The present disclosure also provides a vector that may be used for preparation of the variant polypeptide or compositions comprising the variant polypeptide as described herein. In some embodiments, the disclosure includes the composition or vector described herein in a cell. In some embodiments, the disclosure includes a method of expressing the composition comprising the variant polypeptide, or vector or nucleic acid encoding the variant polypeptide, in a cell. The method may comprise the steps of providing the composition, e.g., vector or nucleic acid, and delivering the composition to the cell.

Expression of natural or synthetic polynucleotides is typically achieved by operably linking a polynucleotide encoding the gene of interest, e.g., a nucleotide sequence encoding the variant polypeptide, to a promoter and incorporating the construct into an expression vector. The expression vector is not particularly limited as long as it includes a polynucleotide encoding the variant polypeptide of the present disclosure and can be suitable for replication and integration in eukaryotic cells.

Typical expression vectors may include transcription and translation terminators, initiation sequences, and promoters useful for expression of the desired polynucleotide. For example, plasmid vectors carrying a recognition sequence for RNA polymerase (pSP64, pBluescript, etc.) may be used. Vectors including those derived from retroviruses such as lentivirus are suitable tools to achieve long-term gene transfer since they allow long-term, stable integration of a transgene and its propagation in daughter cells. Examples of vectors include expression vectors, replication vectors, probe generation vectors, and sequencing vectors. The expression vector may be provided to a cell in the form of a viral vector.

Viral vector technology is well known in the art and described in a variety of virology and molecular biology manuals. Viruses which are useful as vectors include, but are not limited to, phage viruses, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers.

The kind of the vector is not particularly limited, and a vector that can be expressed in host cells can be appropriately selected. To be more specific, depending on the kind of the host cell, a promoter sequence to ensure the expression of the variant polypeptide from the polynucleotide is appropriately selected, and this promoter sequence and the polynucleotide are inserted into any of various plasmids etc. for preparation of the expression vector.

Additional promoter elements, e.g., enhancing sequences, regulate the frequency of transcriptional initiation. Typically, these are located in the region 30-110 bp upstream of the start site, although a number of promoters have recently been shown to contain functional elements downstream of the start site as well. Depending on the promoter, it appears that individual elements can function either cooperatively or independently to activate transcription.

Further, the disclosure should not be limited to the use of constitutive promoters. Inducible promoters are also contemplated as part of the disclosure. The use of an inducible promoter provides a molecular switch capable of turning on expression of the polynucleotide sequence which it is operatively linked when such expression is desired or turning off the expression when expression is not desired. Examples of inducible promoters include, but are not limited to a metallothionine promoter, a glucocorticoid promoter, a progesterone promoter, and a tetracycline promoter.

The expression vector to be introduced can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate transcriptional control sequences to enable expression in the host cells. Examples of such a marker include a dihydrofolate reductase gene and a neomycin resistance gene for eukaryotic cell culture; and a tetracycline resistance gene and an ampicillin resistance gene for culture of *E. coli* and other bacteria. By use of such a selection marker, it can be confirmed whether the polynucleotide encoding the variant polypeptide of the present disclosure has been transferred into the host cells and then expressed without fail.

The preparation method for recombinant expression vectors is not particularly limited, and examples thereof include methods using a plasmid, a phage, or a cosmid.

Methods of Expression

The present disclosure includes a method for protein expression, comprising translating the variant polypeptide described herein.

In some embodiments, a host cell described herein is used to express the variant polypeptide. The host cell is not particularly limited, and various known cells can be preferably used. Specific examples of the host cell include bacteria such as *E. coli*, yeasts (budding yeast, *Saccharomyces cerevisiae*, and fission yeast, *Schizosaccharomyces pombe*), nematodes (*Caenorhabditis elegans*), *Xenopus laevis* oocytes, and animal cells (for example, CHO cells, COS cells and HEK293 cells). The method for transferring the expression vector described above into host cells, i.e., the transformation method, is not particularly limited, and known methods such as electoporation, the calcium phosphate method, the liposome method and the DEAE dextran method can be used.

After a host is transformed with the expression vector, the host cells may be cultured, cultivated, or bred, for production of the variant polypeptide. After expression of the variant polypeptide, the host cells can be collected and variant polypeptide purified from the cultures etc. according to conventional methods (for example, filtration, centrifugation, cell disruption, gel filtration chromatography, ion exchange chromatography, etc.).

In some embodiments, the methods for variant polypeptide expression comprises translation of at least 5 amino acids, at least 10 amino acids, at least 15 amino acids, at least 20 amino acids, at least 50 amino acids, at least 100 amino acids, at least 150 amino acids, at least 200 amino acids, at least 250 amino acids, at least 300 amino acids, at least 400 amino acids, at least 500 amino acids, at least 600 amino acids, at least 700 amino acids, at least 800 amino acids, at least 900 amino acids, or at least 1000 amino acids of the variant polypeptide. In some embodiments, the methods for protein expression comprises translation of about 5 amino acids, about 10 amino acids, about 15 amino acids, about 20 amino acids, about 50 amino acids, about 100 amino acids, about 150 amino acids, about 200 amino acids, about 250 amino acids, about 300 amino acids, about 400 amino acids, about 500 amino acids, about 600 amino acids, about 700 amino acids, about 800 amino acids, about 900 amino acids, about 1000 amino acids or more of the variant polypeptide.

A variety of methods can be used to determine the level of production of a mature variant polypeptide in a host cell. Such methods include, but are not limited to, for example, methods that utilize either polyclonal or monoclonal antibodies specific for the variant polypeptide or a labeling tag as described elsewhere herein. Exemplary methods include, but are not limited to, enzyme-linked immunosorbent assays (ELISA), radioimmunoassays (RIA), fluorescent immunoassays (FIA), and fluorescent activated cell sorting (FACS). These and other assays are well known in the art (See, e.g., Maddox et al., J. Exp. Med. 158:1211 [1983]).

The present disclosure provides methods of in vivo expression of the variant polypeptide in a cell, comprising providing a polyribonucleotide encoding the variant polypeptide to a host cell wherein the polyribonucleotide encodes the variant polypeptide, expressing the variant polypeptide in the cell, and obtaining the variant polypeptide from the cell.

Introduction of Alteration or Mutation

Nucleic acid sequences encoding variant polypeptides or variant polypeptides may be generated by synthetic methods known in the art. Using the nucleic acid sequence encoding the parent polypeptide itself as a framework, alternations or mutations can be inserted one or more at a time to alter the nucleic acid sequence encoding the parent polypeptide. Along the same lines, the parent polypeptide may be altered or mutated by introducing the changes into the polypeptide sequence as it is synthetically synthesized. This may be accomplished by methods well known in the art.

The production and introduction of alteration or mutation into a parent polypeptide sequence can be accomplished using any methods known by those of skill in the art. In particular, in some embodiments, oligonucleotide primers for PCR may be used for the rapid synthesis of a DNA template including the one or more alterations or mutations in the nucleic acid sequence encoding for the variant polypeptide. Site-specific mutagenesis may also be used as a technique useful in the preparation of individual peptides, or biologically functional equivalent proteins or peptides, through specific mutagenesis of the underlying DNA. The technique further provides a ready ability to prepare and test variants, incorporating one or more of the foregoing considerations, by introducing one or more nucleotide sequence changes into the DNA. Site-specific mutagenesis allows the production of variants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

Introduction of structural variations, such as fusion of polypeptides as amino- and/or carboxyl-terminal extensions can be accomplished in a similar fashion as introduction of alterations or mutations into the parent polypeptide. The additional peptides may be added to the parent polypeptide or variant polypeptide by including the appropriate nucleic acid sequence encoding the additional peptides to the nucleic acid sequence encoding the parent polypeptide or variant polypeptide. Optionally, the additional peptides may be appended directly to the variant polypeptide through synthetic polypeptide production.

In an aspect, the disclosure also provides methods for introducing an alteration or mutation into the parent polypeptide sequence to produce a variant polypeptide that has increased on-target binding with two or more loci (e.g., 2, 3, 4, 5, 6, 7, 8, 9, or more) of a target nucleic acid, as compared to a parent polypeptide.

In an aspect, the disclosure also provides methods for introducing an alteration or mutation into the parent polypeptide sequence to produce a plurality of variant polypeptides (e.g., separate variant polypeptides having the same amino acid sequence), that when individually complexed with a plurality of distinct RNA guides, have increased on-target binding with two or more loci of a target nucleic acid, as compared to a plurality of parent polypeptides and RNA guides.

In an aspect, the disclosure also provides methods for introducing an alteration or mutation into the parent polypeptide sequence to produce a variant polypeptide that has increased on-target ternary complex formation with two or more target loci of a target nucleic acid, as compared to a parent polypeptide.

In an aspect, the disclosure also provides methods for introducing an alteration or mutation into the parent polypeptide sequence to produce a plurality of variant polypeptides (e.g., separate variant polypeptides having the same amino acid sequence), that when individually complexed with a plurality of distinct RNA guides, have increased ternary complex formation with two or more loci of a target nucleic acid, as compared to a plurality of parent polypeptides and RNA guides.

In an aspect, the disclosure also provides methods for introducing an alteration or mutation into the parent polypeptide sequence to produce a variant polypeptide that exhibits targeting of an increased number of target nucleic acids or target loci, as compared to a parent polypeptide.

In an aspect, the disclosure also provides methods for introducing an alteration or mutation into the parent polypeptide sequence to produce a plurality of variant polypeptides (e.g., separate variant polypeptides having the same amino acid sequence), that when individually complexed with a plurality of distinct RNA guides, exhibit targeting of an increased number of target nucleic acids or target loci, as compared to a plurality of parent polypeptides and RNA guides.

In an aspect, the disclosure also provides methods for introducing an alteration or mutation into the parent polypeptide sequence to enhance stability of the variant polypeptide. Stability of the variant polypeptide can be determined by or may include a technique not limited to thermal denaturation assays, thermal shift assays, differential scanning calorimetry (DSC), differential scanning fluorimetry (DSF), isothermal titration calorimetry (ITC), pulse-chase methods, bleach-chase methods, cycloheximide-chase methods, circular dichroism (CD) spectroscopy, crystallization, and fluorescence-based activity assays.

Variant Selection for Functionality

In an aspect, the disclosure provides methods for introducing an alteration or mutation into the parent polypeptide sequence to enhance binary complex formation, RNA guide binding activity, and/or RNA guide binding specificity.

In an aspect, the disclosure also provides methods for introducing an alteration or mutation into the parent polypeptide sequence to enhance ternary complex formation, on-target binding affinity, on-target binding activity, on-target binding, and/or on-target binding specificity. In an aspect, the disclosure also provides methods for introducing an alteration or mutation into the parent polypeptide sequence to enhance on-target binding affinity (e.g., affinity or time it takes to interact with target), on-target binding activity (e.g., nuclease activity when interacting with target), on-target binding (e.g., strength of interaction with target), and/or on-target binding specificity (e.g., preference for specific target) of a binary complex (e.g., ribonucleoprotein).

In some embodiments, an alteration or mutation is introduced to the parent polypeptide sequence to produce a variant polypeptide that has increased on-target binding and/or activity. Also, in such embodiments, off-target binding and/or activity can be decreased in the variant polypeptide, as compared to the parent polypeptide. Moreover, there can be increased or decreased specificity as to on-target binding vs. off-target binding.

In some embodiments, an alteration or mutation is introduced to the parent polypeptide sequence to produce a variant polypeptide, that when complexed with an RNA guide, has increased on-target binding. Also, in such embodiments, off-target binding can be decreased in the complex comprising the variant polypeptide and RNA guide. Moreover, there can be increased or decreased specificity as to on-target binding/activity vs. off-target binding/activity.

In certain embodiments, an alteration or mutation is introduced to the parent polypeptide sequence to produce a variant polypeptide that enhances stability and/or protein-RNA interactions. In certain embodiments, variant polypeptide includes at least one alteration that promotes stability and/or RNA interactions as well as enzymatic activity of the variant polypeptide, as compared to a parent polypeptide.

In certain embodiments, an alteration or mutation is introduced to the parent polypeptide sequence to produce a variant polypeptide that (a) lacks enzymatic activity, yet (b) retains enhanced stability and/or protein-RNA interactions. In certain embodiments, variant polypeptide includes at least one alteration that promotes stability and/or RNA interactions, but not enzymatic activity of the variant polypeptide, as compared to a parent polypeptide.

In certain embodiments, an alteration or mutation is introduced to the parent polypeptide sequence to produce a variant polypeptide that (a) enhances enzymatic activity, and (b) enhances binary complex formation, RNA guide binding activity, and/or RNA guide binding specificity. In certain embodiments, variant polypeptide includes at least one alteration that promotes RNA guide complex formation, RNA guide binding activity, and/or RNA guide binding specificity as well as enzymatic activity of the variant polypeptide, as compared to a parent polypeptide.

In certain embodiments, an alteration or mutation is introduced to the parent polypeptide sequence to produce a variant polypeptide that (a) lacks enzymatic activity, yet (b) retains enhanced binary complex formation, RNA guide binding activity, and/or RNA guide binding specificity. In certain embodiments, variant polypeptide includes at least one alteration that promotes binary complex formation, RNA guide binding activity, and/or RNA guide binding specificity, but not enzymatic activity of the variant polypeptide, as compared to a parent polypeptide.

In certain embodiments, an alteration or mutation is introduced to the parent polypeptide sequence to produce a variant polypeptide that (a) enhances enzymatic activity, and (b) enhances on-target ternary complex formation, on-target binding affinity, on-target binding activity, and/or on-target binding specificity. In certain embodiments, variant polypeptide includes at least one alteration that promotes on-target ternary complex formation, on-target binding affinity, on-target binding activity, and/or on-target binding specificity as well as enzymatic activity of the variant polypeptide, as compared to a parent polypeptide.

In certain embodiments, an alteration or mutation is introduced to the parent polypeptide sequence to produce a variant polypeptide that (a) lacks enzymatic activity, yet (b) retains enhanced on-target ternary complex formation, on-target binding affinity, on-target binding activity, and/or on-target binding specificity. In certain embodiments, variant polypeptide includes at least one alteration that promotes on-target ternary complex formation, on-target binding affinity, on-target binding activity, and/or on-target binding specificity, but not enzymatic activity of the variant polypeptide, as compared to a parent polypeptide.

In some embodiments, at least one alteration is introduced into the parent polypeptide of SEQ ID NO: 3 to produce a variant polypeptide that exhibits (a) decreased enzymatic activity and (b) enhanced RNA affinity relative to the parent polypeptide of SEQ ID NO: 3. In some embodiments, at least one alteration is introduced into the parent polypeptide of SEQ ID NO: 3 to produce a variant polypeptide that exhibits (a) increased enzymatic activity and (b) enhanced RNA affinity, relative to the parent polypeptide of SEQ ID NO: 3. In some embodiments, at least one alteration is introduced into the parent polypeptide of SEQ ID NO: 3 to produce a variant polypeptide that exhibits (a) retained enzymatic activity and (b) enhanced RNA affinity, relative to the parent polypeptide of SEQ ID NO: 3.

In some embodiments, at least one alteration is introduced into the parent polypeptide of SEQ ID NO: 3 to produce a variant polypeptide that exhibits (a) decreased enzymatic activity and (b) enhanced binary complex formation relative to the parent polypeptide of SEQ ID NO: 3. In some embodiments, at least one alteration is introduced into the parent polypeptide of SEQ ID NO: 3 to produce a variant polypeptide that exhibits (a) increased enzymatic activity and (b) enhanced binary complex formation, relative to the parent polypeptide of SEQ ID NO: 3. In some embodiments, at least one alteration is introduced into the parent polypeptide of SEQ ID NO: 3 to produce a variant polypeptide that exhibits (a) retained enzymatic activity and (b) enhanced binary complex formation, relative to the parent polypeptide of SEQ ID NO: 3.

In some embodiments, at least one alteration is introduced into the parent polypeptide of SEQ ID NO: 3 to produce a variant polypeptide that exhibits (a) decreased enzymatic activity and (b) enhanced RNA guide binding activity relative to the parent polypeptide of SEQ ID NO: 3. In some embodiments, at least one alteration is introduced into the parent polypeptide of SEQ ID NO: 3 to produce a variant polypeptide that exhibits (a) increased enzymatic activity and (b) enhanced RNA guide binding activity, relative to the parent polypeptide of SEQ ID NO: 3. In some embodiments, at least one alteration is introduced into the parent polypeptide of SEQ ID NO: 3 to produce a variant polypeptide that exhibits (a) retained enzymatic activity and (b) enhanced RNA guide binding activity, relative to the parent polypeptide of SEQ ID NO: 3.

In some embodiments, at least one alteration is introduced into the parent polypeptide of SEQ ID NO: 3 to produce a variant polypeptide that exhibits (a) decreased enzymatic activity and (b) enhanced RNA guide binding specificity relative to the parent polypeptide of SEQ ID NO: 3. In some embodiments, at least one alteration is introduced into the parent polypeptide of SEQ ID NO: 3 to produce a variant polypeptide that exhibits (a) increased enzymatic activity and (b) enhanced RNA guide binding specificity, relative to the parent polypeptide of SEQ ID NO: 3. In some embodiments, at least one alteration is introduced into the parent polypeptide of SEQ ID NO: 3 to produce a variant polypeptide that exhibits (a) retained enzymatic activity and (b) enhanced RNA guide binding specificity, relative to the parent polypeptide of SEQ ID NO: 3.

In some embodiments, at least one alteration is introduced into the parent polypeptide of SEQ ID NO: 3 to produce a variant polypeptide that exhibits (a) decreased enzymatic activity and (b) enhanced protein-RNA interactions relative to the parent polypeptide of SEQ ID NO: 3. In some embodiments, at least one alteration is introduced into the parent polypeptide of SEQ ID NO: 3 to produce a variant polypeptide that exhibits (a) increased enzymatic activity and (b) enhanced protein-RNA interactions, relative to the parent polypeptide of SEQ ID NO: 3. In some embodiments, at least one alteration is introduced into the parent polypeptide of SEQ ID NO: 3 to produce a variant polypeptide that exhibits (a) retained enzymatic activity and (b) enhanced protein-RNA interactions, relative to the parent polypeptide of SEQ ID NO: 3.

In some embodiments, at least one alteration is introduced into the parent polypeptide of SEQ ID NO: 3 to produce a variant polypeptide that exhibits (a) decreased enzymatic activity and (b) enhanced protein stability relative to the parent polypeptide of SEQ ID NO: 3. In some embodiments, at least one alteration is introduced into the parent polypeptide of SEQ ID NO: 3 to produce a variant polypeptide that exhibits (a) increased enzymatic activity and (b) enhanced protein stability, relative to the parent polypeptide of SEQ ID NO: 3. In some embodiments, at least one alteration is introduced into the parent polypeptide of SEQ ID NO: 3 to produce a variant polypeptide that exhibits (a) retained enzymatic activity and (b) enhanced protein stability, relative to the parent polypeptide of SEQ ID NO: 3.

In some embodiments, at least one alteration is introduced into the parent polypeptide of SEQ ID NO: 3 to produce a variant polypeptide that exhibits (a) decreased enzymatic activity and (b) decreased dissociation from an RNA guide relative to the parent polypeptide of SEQ ID NO: 3. In some embodiments, at least one alteration is introduced into the parent polypeptide of SEQ ID NO: 3 to produce a variant polypeptide that exhibits (a) increased enzymatic activity and (b) decreased dissociation from an RNA guide, relative to the parent polypeptide of SEQ ID NO: 3. In some embodiments, at least one alteration is introduced into the parent polypeptide of SEQ ID NO: 3 to produce a variant polypeptide that exhibits (a) retained enzymatic activity and (b) decreased dissociation from an RNA guide, relative to the parent polypeptide of SEQ ID NO: 3.

In some embodiments, at least one alteration is introduced into the parent polypeptide of SEQ ID NO: 3 to produce a variant polypeptide that exhibits (a) decreased enzymatic activity and (b) enhanced ternary complex formation relative to the parent polypeptide of SEQ ID NO: 3. In some embodiments, at least one alteration is introduced into the parent polypeptide of SEQ ID NO: 3 to produce a variant polypeptide that exhibits (a) increased enzymatic activity and (b) enhanced ternary complex formation, relative to the parent polypeptide of SEQ ID NO: 3. In some embodiments, at least one alteration is introduced into the parent polypeptide of SEQ ID NO: 3 to produce a variant polypeptide that exhibits (a) retained enzymatic activity and (b) enhanced ternary complex formation, relative to the parent polypeptide of SEQ ID NO: 3.

In some embodiments, at least one alteration is introduced into the parent polypeptide of SEQ ID NO: 3 to produce a variant polypeptide that forms a variant binary complex exhibiting (a) decreased enzymatic activity and (b) enhanced binding affinity to a target nucleic acid, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex exhibiting (a) increased enzymatic activity and (b) enhanced binding affinity to a target nucleic acid, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex that exhibits (a) retained enzymatic activity and (b) enhanced binding affinity to a target nucleic acid, relative to a parent binary complex comprising the polypeptide of SEQ ID NO: 3.

In some embodiments, at least one alteration is introduced into the parent polypeptide of SEQ ID NO: 3 to produce a variant polypeptide that forms a variant binary complex exhibiting (a) decreased enzymatic activity and (b) enhanced on-target binding activity, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex exhibiting (a) increased enzymatic activity and (b) enhanced on-target binding activity, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex that exhibits (a) retained enzymatic activity and (b) enhanced on-target binding activity, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex exhibiting (a) decreased enzymatic activity and (b) enhanced on-target binding specificity, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex exhibiting (a) increased enzymatic activity and (b) enhanced on-target binding specificity, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex that exhibits (a) retained enzymatic activity and (b) enhanced on-target binding specificity, relative to a parent binary complex comprising the polypeptide of SEQ ID NO: 3.

In some embodiments, at least one alteration is introduced into the parent polypeptide of SEQ ID NO: 3 to produce a variant polypeptide that forms a variant binary complex exhibiting (a) decreased enzymatic activity and (b) decreased off-target binding to a non-target nucleic acid, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex exhibiting (a) increased enzymatic activity and (b) decreased off-target binding to a non-target nucleic acid, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex exhibiting (a) retained enzymatic activity and (b) decreased off-target binding to a non-target nucleic acid, relative to a parent binary complex comprising the polypeptide of SEQ ID NO: 3.

In some embodiments, at least one alteration is introduced into the parent polypeptide of SEQ ID NO: 3 to produce a variant polypeptide that forms a variant binary complex exhibiting (a) decreased enzymatic activity and (b) decreased dissociation from the target nucleic acid, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex exhibiting (a) increased enzymatic activity and (b) decreased dissociation from the target nucleic acid, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex exhibiting (a) retained enzymatic activity and (b) decreased dissociation from the target nucleic acid, relative to a parent binary complex comprising the polypeptide of SEQ ID NO: 3.

Variant Binary Complexing

Generally, the variant polypeptide and the RNA guide bind to each other in a molar ratio of about 1:1 to form the variant binary complex. The variant polypeptide and the RNA guide, either alone or together, do not naturally occur.

In some embodiments, the variant polypeptide can be overexpressed in a host cell and purified as described herein, then complexed with the RNA guide (e.g., in a test tube) to form a variant ribonucleoprotein (RNP) (e.g., variant binary complex).

In some embodiments, the variant binary complex exhibits increased binding affinity to a target nucleic acid, increased on-target binding activity, increased on-target binding specificity, increased ternary complex formation with a target nucleic acid, and/or increased stability over a range of incubation times. In some embodiments, the variant binary complex exhibits decreased off-target binding to a non-target nucleic acid and/or decreased dissociation from a target nucleic acid over a range of incubation times. In some embodiments, the variant binary complex exhibits increased target nucleic acid complex formation, target nucleic acid activity, and/or target nucleic acid specificity over a range of incubation times.

In some embodiments, complexation of a binary complex occurs at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., or 55° C. In some embodiments, the variant polypeptide does not dissociate from the RNA guide or bind to a free RNA at about 37° C. over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours. In some embodiments, after binary complex formation, the variant ribonucleoprotein complex does not exchange the RNA guide with a different RNA.

In some embodiments, the variant polypeptide and RNA guide are complexed in a binary complexation buffer. In some embodiments, the variant polypeptide is stored in a buffer that is replaced with a binary complexation buffer to form a complex with the RNA guide. In some embodiments, the variant polypeptide is stored in a binary complexation buffer.

In some embodiments, the binary complexation buffer has a pH in a range of about 7.3 to 8.6. In one embodiment, the pH of the binary complexation buffer is about 7.3. In one embodiment, the pH of the binary complexation buffer is about 7.4. In one embodiment, the pH of the binary complexation buffer is about 7.5. In one embodiment, the pH of the binary complexation buffer is about 7.6. In one embodiment, the pH of the binary complexation buffer is about 7.7. In one embodiment, the pH of the binary complexation buffer is about 7.8. In one embodiment, the pH of the binary complexation buffer is about 7.9. In one embodiment, the pH of the binary complexation buffer is about 8.0. In one embodiment, the pH of the binary complexation buffer is about 8.1. In one embodiment, the pH of the binary complexation buffer is about 8.2. In one embodiment, the pH of the binary complexation buffer is about 8.3. In one embodiment, the pH of the binary complexation buffer is about 8.4. In one embodiment, the pH of the binary complexation buffer is about 8.5. In one embodiment, the pH of the binary complexation buffer is about 8.6.

The thermostability of the variant polypeptide can increase under favorable conditions such as the addition of an RNA guide, e.g., binding an RNA guide.

In some embodiments, the variant polypeptide can be overexpressed and complexed with the RNA guide in a host cell prior to purification as described herein. In some embodiments, mRNA or DNA encoding the variant polypeptide is introduced into a cell so that the variant polypeptide is expressed in the cell. The RNA guide, which guides the variant polypeptide to the desired target nucleic acid is also introduced into the cell, whether simultaneously, separately or sequentially from a single mRNA or DNA construct, such that the necessary ribonucleoprotein complex is formed in the cell.

Assessing Variant Binary Complex Stability and Functionality Provided herein in certain embodiments are methods for identifying an optimal variant polypeptide/RNA guide complex (referred to herein as the variant binary complex) including (a) combining a variant polypeptide and an RNA guide in a sample to form the variant binary complex; (b) measuring a value of the variant binary complex; and (c) determining the variant binary complex is optimal over the reference molecule, if the value of the variant binary complex is greater than a value of a reference molecule. In some embodiments, the value may include, but is not limited to, a stability measurement (e.g., Tm value, thermostability), a rate of binary complex formation, RNA guide binding specificity, and/or complex activity.

In some embodiments, an optimal variant polypeptide/RNA guide complex (i.e., a variant binary complex) is identified by the steps of: (a) combining a variant polypeptide and an RNA guide in a sample to form the variant binary complex; (b) detecting a Tm value of the variant binary complex; and (c) determining the variant binary complex is stable if the Tm value of the variant binary complex is greater than a Tm value of a reference molecule or a Tm reference value by at least 8° C.

The methods involving a step of measuring the thermostability of a variant polypeptide/RNA guide complex (i.e., a variant binary complex) may include, without limitation, methods of determining the stability of a variant binary complex, methods of determining a condition that promotes a stable variant binary complex, methods of screening for a stable variant binary complex, and methods for identifying an optimal RNA guide to form a stable variant binary complex. In certain embodiments, a thermostability value of a variant binary complex may be measured.

Additionally, in certain embodiments, a thermostability value of a reference molecule may also be measured. In certain embodiments, a variant binary complex may be determined to be stable if the measured thermostability value of the variant binary complex is greater than the measured thermostability value of the reference molecule or a thermostability reference value, measured under the same experimental conditions, as described herein. In certain embodiments, the reference molecule may be the variant polypeptide absent an RNA guide.

In certain embodiments, the thermostability value that is measured may be a denaturation temperature value. In these embodiments, the thermostability reference value is a denaturation temperature reference value. In certain embodiments, the thermostability value that is measured may be a Tm value. In these embodiments, the thermostability reference value may be a Tm reference value. In certain embodiments, the thermostability value may be measured using a thermal shift assay. In certain embodiments, an assay used to measure thermostability may involve a technique described herein including, but not limited to, thermal denaturation assays, thermal shift assays, differential scanning calorimetry (DSC), differential scanning fluorimetry (DSF), isothermal titration calorimetry (ITC), pulse-chase methods, bleach-chase methods, cycloheximide-chase methods, circular dichroism (CD) spectroscopy, crystallization, and fluorescence-based activity assays.

In certain embodiments, a variant binary complex may be identified if the rate of variant polypeptide/RNA guide complex formation, RNA guide binding specificity, and/or complex activity of the variant binary complex is greater than a value of the reference molecule or the reference value (e.g., a value of a parent polypeptide/RNA guide complex, referred to herein as a parent binary complex). For example, in certain embodiments, the variant binary complex may be identified if the value of a rate of variant polypeptide/RNA guide complex formation, RNA guide binding specificity, and/or complex activity of the variant binary complex is at least X % greater than a value of the reference molecule or the reference value (e.g., a value of a parent binary complex). In certain embodiments, the methods described herein may further comprise steps that include measuring the activity of the variant binary complex as described herein.

Variant Ternary Complexing

In some embodiments, the variant polypeptide, RNA guide, and target nucleic acid, as described herein, form a variant ternary complex (e.g., in a test tube or cell). Generally, the variant polypeptide, the RNA guide, and the target nucleic acid associate with each other in a molar ratio of about 1:1:1 to form the variant ternary complex. The variant polypeptide, the RNA guide, and the target nucleic acid, either alone or together, do not naturally occur.

In some embodiments, the variant binary complex (e.g., complex of variant polypeptide and RNA guide) as described herein, is further complexed with the target nucleic acid (e.g., in a test tube or cell) to form a variant ternary complex.

In some embodiments, complexation of the ternary complex occurs at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., or 55° C. In some embodiments, the variant binary complex does not dissociate from the target nucleic acid or bind to a free nucleic acid (e.g., free DNA) at about 37° C. over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours. In some embodiments, after ternary complex formation, a variant binary complex does not exchange the target nucleic acid with a different nucleic acid.

In some embodiments, the variant polypeptide, RNA guide, and target nucleic acid are complexed in a ternary complexation buffer. In some embodiments, the variant polypeptide is stored in a buffer that is replaced with a ternary complexation buffer to form a complex with the RNA guide and target nucleic acid. In some embodiments, the variant polypeptide is stored in a ternary complexation buffer.

In some embodiments, the variant binary complex and target nucleic acid are complexed in a ternary complexation buffer. In some embodiments, the variant binary complex is stored in a buffer that is replaced with a ternary complexation buffer to form a complex with the target nucleic acid. In some embodiments, the variant binary complex is stored in a ternary complexation buffer.

In some embodiments, the ternary complexation buffer has a pH in a range of about 7.3 to 8.6. In one embodiment, the pH of the ternary complexation buffer is about 7.3. In one embodiment, the pH of the ternary complexation buffer is about 7.4. In one embodiment, the pH of the ternary complexation buffer is about 7.5. In one embodiment, the pH of the ternary complexation buffer is about 7.6. In one embodiment, the pH of the ternary complexation buffer is about 7.7. In one embodiment, the pH of the ternary complexation buffer is about 7.8. In one embodiment, the pH of the ternary complexation buffer is about 7.9. In one embodiment, the pH of the ternary complexation buffer is about 8.0. In one embodiment, the pH of the ternary complexation buffer is about 8.1. In one embodiment, the pH of the ternary complexation buffer is about 8.2. In one embodiment, the pH of the ternary complexation buffer is about 8.3. In one embodiment, the pH of the ternary complexation buffer is about 8.4. In one embodiment, the pH of the ternary complexation buffer is about 8.5. In one embodiment, the pH of the ternary complexation buffer is about 8.6.

The thermostability of a variant polypeptide can increase under favorable conditions such as the addition of an RNA guide and target nucleic acid.

Assessing Variant Ternary Complex Stability and Functionality

Provided herein in certain embodiments are methods for identifying an optimal variant ternary complex including (a) combining a variant polypeptide, an RNA guide, and a target nucleic acid in a sample to form the variant ternary complex; (b) measuring a value of the variant ternary complex; and (c) determining the variant ternary complex is optimal over the reference molecule, if the value of the variant ternary complex is greater than a value of a reference molecule. In some embodiments, the value may include, but is not limited to, a stability measurement (e.g., Tm value, thermostability), a rate of ternary complex formation, a DNA binding affinity measurement, a DNA binding specificity measurement, and/or a complex activity measurement (e.g., nuclease activity measurement).

In some embodiments, an optimal variant ternary complex is identified by the steps of: (a) combining a variant polypeptide, an RNA guide, and a target nucleic acid in a sample to form the variant ternary complex; (b) detecting a Tm value of the variant ternary complex; and (c) determining the variant ternary complex is stable if the Tm value of the variant ternary complex is greater than a Tm value of a reference molecule or a Tm reference value by at least 8° C.

The methods involving a step of measuring the thermostability of a variant ternary complex may include, without limitation, methods of determining the stability of a variant ternary complex, methods of determining a condition that promotes a stable variant ternary complex, methods of screening for a stable variant ternary complex, and methods for identifying an optimal binary complex to form a stable variant ternary complex. In certain embodiments, a thermostability value of a variant ternary complex may be measured.

Additionally, in certain embodiments, a thermostability value of a reference molecule may also be measured. In certain embodiments, a variant ternary complex may be determined to be stable if the measured thermostability value of the variant ternary complex is greater than the measured thermostability value of the reference molecule or a thermostability reference value, measured under the same experimental conditions, as described herein. In certain embodiments, the reference molecule may be the variant polypeptide absent an RNA guide and/or target nucleic acid.

In certain embodiments, the thermostability value that is measured may be a denaturation temperature value. In these embodiments, the thermostability reference value is a denaturation temperature reference value. In certain embodiments, the thermostability value that is measured may be a Tm value. In these embodiments, the thermostability reference value may be a Tm reference value. In certain embodiments, the thermostability value may be measured using a thermal shift assay. In certain embodiments, an assay used to measure thermostability may involve a technique described herein including, but not limited to, differential scanning fluorimetry (DSF), differential scanning calorimetry (DSC), or isothermal titration calorimetry (ITC).

In certain embodiments, a variant ternary complex may be identified if the rate of ternary complex formation, DNA binding affinity, DNA binding specificity, and/or complex activity (e.g., nuclease activity) of the variant ternary complex is greater than a value of the reference molecule or the reference value (e.g., a value of a parent ternary complex). For example, in certain embodiments, the variant ternary complex may be identified if the value of a rate of ternary complex formation, DNA binding affinity, DNA binding specificity, and/or complex activity of the variant ternary complex is at least X % greater than a value of the reference molecule or the reference value (e.g., a value of a parent ternary complex). In certain embodiments, the methods described herein may further comprise steps that include measuring the activity of the variant ternary complex as described herein.

In one aspect, a method for modifying a target DNA molecule is provided, the method comprising contacting the target DNA molecule with the variant polypeptide disclosed herein and the RNA guide disclosed herein. In some embodiments, the target DNA molecule is in vitro. In some embodiments, the target DNA molecule is in a cell. In certain embodiments, the cell is in vitro, ex vivo, or in vivo. In some embodiments, the cell is selected from a prokaryotic cell, a eukaryotic cell, a plant cell, a mammalian cell, and a human cell.

Delivery

Compositions or complexes described herein may be formulated, for example, including a carrier, such as a carrier and/or a polymeric carrier, e.g., a liposome, and delivered by known methods to a cell (e.g., a prokaryotic, eukaryotic, plant, mammalian, etc.). Such methods include, but not limited to, transfection (e.g., lipid-mediated, cationic polymers, calcium phosphate, dendrimers); electroporation or other methods of membrane disruption (e.g., nucleofection), viral delivery (e.g., lentivirus, retrovirus, adenovirus, AAV), microinjection, microprojectile bombardment ("gene gun"), fugene, direct sonic loading, cell squeezing, optical transfection, protoplast fusion, impalefection, magnetofection, exosome-mediated transfer, lipid nanoparticle-mediated transfer, and any combination thereof.

In some embodiments, the method comprises delivering one or more nucleic acids (e.g., nucleic acids encoding the variant polypeptide, RNA guide, donor DNA, etc.), one or more transcripts thereof, and/or a pre-formed variant polypeptide/RNA guide complex (i.e., variant binary complex) to a cell. Exemplary intracellular delivery methods, include, but are not limited to: viruses or virus-like agents; chemical-based transfection methods, such as those using calcium phosphate, dendrimers, liposomes, or cationic polymers (e.g., DEAE-dextran or polyethylenimine); non-chemical methods, such as microinjection, electroporation, cell squeezing, sonoporation, optical transfection, impalefection, protoplast fusion, bacterial conjugation, delivery of plasmids or transposons; particle-based methods, such as using a gene gun, magnetofection or magnet assisted transfection, particle bombardment; and hybrid methods, such as nucleofection. In some embodiments, the present application further provides cells produced by such methods, and organisms (such as animals, plants, or fungi) comprising or produced from such cells.

Cells

Polypeptides, compositions or complexes described herein may be delivered to a variety of cells. In some embodiments, the cell is an isolated cell. In some embodiments the cell is in cell culture. In some embodiments, the cell is ex vivo. In some embodiments, the cell is obtained from a living organism, and maintained in a cell culture. In some embodiments, the cell is a single-cellular organism.

In some embodiments, the cell is a prokaryotic cell. In some embodiments, the cell is a bacterial cell or derived from a bacterial cell. In some embodiments, the bacterial cell is not related to the bacterial species from which the parent polypeptide is derived. In some embodiments, the cell is an archaeal cell or derived from an archaeal cell. In some embodiments, the cell is a eukaryotic cell. In some embodiments, the cell is a plant cell or derived from a plant cell. In some embodiments, the cell is a fungal cell or derived from a fungal cell. In some embodiments, the cell is an animal cell or derived from an animal cell. In some embodiments, the cell is an invertebrate cell or derived from an invertebrate cell. In some embodiments, the cell is a vertebrate cell or derived from a vertebrate cell. In some embodiments, the cell is a mammalian cell or derived from a mammalian cell. In some embodiments, the cell is a human cell. In some embodiments, the cell is a zebra fish cell. In some embodiments, the cell is a rodent cell. In some embodiments, the cell is synthetically made, sometimes termed an artificial cell.

In some embodiments, the cell is derived from a cell line. A wide variety of cell lines for tissue culture are known in the art. Examples of cell lines include, but are not limited to, 293T, MF7, K562, HeLa, and transgenic varieties thereof. Cell lines are available from a variety of sources known to those with skill in the art (see, e.g., the American Type Culture Collection (ATCC) (Manassas, Va.)). In some embodiments, a cell transfected with one or more nucleic acids (such as Ago-coding vector and gDNA) or Ago-gDNA complex described herein is used to establish a new cell line comprising one or more vector-derived sequences to establish a new cell line comprising modification to the target nucleic acid. In some embodiments, cells transiently or non-transiently transfected with one or more nucleic acids (such as variant polypeptide-encoding vector and RNA guide) or variant polypeptide/RNA guide complex (i.e., variant binary complex) described herein, or cell lines derived from such cells are used in assessing one or more test compounds.

In some embodiments, the method comprises introducing into a host cell one or more nucleic acids comprising nucleotide sequences encoding a DNA-targeting RNA (e.g., RNA guide) and/or the variant polypeptide. In one embodiment, a cell comprising a target DNA is in vitro, in vivo, or ex vivo. In other embodiments, nucleic acids comprising nucleotide sequences encoding a DNA-targeting RNA (e.g., RNA guide) and/or the variant polypeptide include recombinant expression vectors e.g., including but not limited to adeno-associated virus constructs, recombinant adenoviral constructs, recombinant lentiviral constructs, recombinant retroviral constructs, and the like.

In some embodiments, the cell is a primary cell. For example, cultures of primary cells can be passaged 0 times, 1 time, 2 times, 4 times, 5 times, 10 times, 15 times or more. In some embodiments, the primary cells are harvest from an individual by any known method. For example, leukocytes may be harvested by apheresis, leukocytapheresis, density gradient separation, etc. Cells from tissues such as skin, muscle, bone marrow, spleen, liver, pancreas, lung, intestine, stomach, etc. can be harvested by biopsy. An appropriate solution may be used for dispersion or suspension of the harvested cells. Such solution can generally be a balanced salt solution, (e.g. normal saline, phosphate-buffered saline (PBS), Hank's balanced salt solution, etc.), conveniently supplemented with fetal calf serum or other naturally occurring factors, in conjunction with an acceptable buffer at low concentration. Buffers can include HEPES, phosphate buffers, lactate buffers, etc. Cells may be used immediately, or they may be stored (e.g., by freezing). Frozen cells can be thawed and can be capable of being reused. Cells can be frozen in a DMSO, serum, medium buffer (e.g., 10% DMSO, 50% serum, 40% buffered medium), and/or some other such common solution used to preserve cells at freezing temperatures.

In some embodiments, the variant polypeptide has nuclease activity that induces double-stranded breaks or single-stranded breaks in a target nucleic acid, (e.g. genomic DNA). The double-stranded break can stimulate cellular endogenous DNA-repair pathways, including Homology Directed Recombination (HDR), Non-Homologous End Joining (NHEJ), or Alternative Non-Homologues End-Joining (A-NHEJ). NHEJ can repair cleaved target nucleic acid without the need for a homologous template. This can result in deletion or insertion of one or more nucleotides into the target nucleic acid. HDR can occur with a homologous template, such as the donor DNA. The homologous template can comprise sequences that are homologous to sequences flanking the target nucleic acid cleavage site. In some cases, HDR can insert an exogenous polynucleotide sequence into the cleaved target nucleic acid. The modifications of the target DNA due to NHEJ and/or HDR can lead to, for example, mutations, deletions, alterations, integrations, gene correction, gene replacement, gene tagging, transgene knock-in, gene disruption, and/or gene knock-outs.

In some embodiments, the cell culture is synchronized to enhance the efficiency of the methods. In some embodiments, cells in S and G2 phases are used for HDR-mediated gene editing. In some embodiments, the cell can be subjected to the method at any cell cycle. In some embodiments, cell over-plating significantly reduces the efficacy of the method. In some embodiments, the method is applied to a cell culture at no more than about any one of 40%, 45%, 50%, 55%, 60%, 65%, or 70% confluency. In some embodiments, binding of the variant polypeptide/RNA guide complex (i.e., variant binary complex) to the target nucleic acid in the cell recruits one or more endogenous cellular molecules or pathways other than DNA repair pathways to modify the target nucleic acid. In some embodiments, binding of the variant binary complex blocks access of one or more endogenous cellular molecules or pathways to the target nucleic acid, thereby modifying the target nucleic acid. For example, binding of the variant binary complex may block endogenous transcription or translation machinery to decrease the expression of the target nucleic acid.

In some embodiments, a method for modifying a target DNA molecule in a cell is provided. The method comprises contacting the target DNA molecule inside of a cell with a variant polypeptide described herein; and a single molecule DNA-targeting RNA comprising, in 5' to 3' order, a first nucleotide segment that hybridizes with a target sequence of the target DNA molecule; a nucleotide linker; and a second nucleotide segment that hybridizes with the first nucleotide segment to form a double-stranded RNA duplex. The variant polypeptide forms a complex with the single molecule DNA-targeting RNA inside the cell and the target DNA molecule is modified.

In one aspect, a method for modifying a target DNA molecule in a cell is provided. The method comprising introducing into the cell the variant polypeptide disclosed herein or a nucleic acid encoding the variant polypeptide, and introducing the RNA guide or a nucleic acid encoding the RNA guide described herein, or introducing the variant binary complex described herein, wherein the introducing comprises introducing a nanoparticle, a liposome, an exosome, a microvesicle, a viral vector, or any combination thereof. In some embodiments, the step of introducing into the cell comprises transfecting or transducing the cell. In some embodiments, the step of introducing comprises use of electroporation, injection, a gene gun, or any combination thereof. In some embodiments, the cell is selected from a prokaryotic cell, a eukaryotic cell, a plant cell, a mammalian cell, and a human cell. In some embodiments, the cell is in vitro, ex vivo, or in vivo.

Kits

The disclosure also provides kits that can be used, for example, to carry out a method described herein. In some embodiments, the kits include a variant polypeptide of the disclosure, e.g., a variant comprising at least one amino acid substitution of Table 2. In some embodiments, the kits include a polynucleotide that encodes such a variant polypeptide, and optionally the polynucleotide is comprised within a vector, e.g., as described herein. The kits also can optionally include an RNA guide, e.g., as described herein. The RNA guide of the kits of the disclosure can be designed to target a sequence of interest, as is known in the art. The CRISPR nuclease variant and the RNA guide can be packaged within the same vial or other vessel within a kit or can be packaged in separate vials or other vessels, the contents of which can be mixed prior to use. The kits can additionally include, optionally, a buffer and/or instructions for use of the CRISPR nuclease variant and/or RNA guide.

All references and publications cited herein are hereby incorporated by reference.

EXAMPLES

The following examples are provided to further illustrate some embodiments of the present disclosure but are not intended to limit the scope of the disclosure; it will be understood by their exemplary nature that other procedures, methodologies, or techniques known to those skilled in the art may alternatively be used.

Example 1—Engineering of Variant Constructs

In this Example, variant constructs were generated.

DNA templates comprising single mutations were constructed via two PCR steps using mutagenic forward and mutagenic reverse primers ordered from IDT. In the first step, two sets of PCR reactions were conducted in 384 plates to generate two fragments. The overlapping regions of two PCR fragments contained the desired single mutations and allowed for the assembly of the entire DNA template via a second PCR. In the second step, the purified fragments from the first step were used as the template for the overlapping PCR (OL PCR) and the Fw and Rv oligos annealing to the vector backbone as the OL PCR primers. The resulting linear DNA templates contained a T7 promoter, a T7 terminator, and the open-reading frame for the CRISPR nuclease.

These linear DNA templates were used directly in a cell-free transcription and translation system to express the CRISPR nuclease variants containing the single mutations. The variant constructs were further individually transferred into transient transfection vectors. Additionally, DNA templates comprising combinatorial mutations are prepared by PCR and subsequently transferred into transient transfection vectors.

Example 2—Florescence Polarization Assay for Variant Binary Complex Detection In this Example, the ability of a CRISPR nuclease polypeptide and an RNA guide to form a binary complex is assessed through a fluorescence polarization assay.

Linear ssDNA fragments comprising the reverse complement of the T7 RNA polymerase promoter sequence upstream of the direct repeat sequence and desired 20 bp RNA guide target are synthesized by IDT. Linear dsDNA in vitro transcription (IVT) templates are then generated by annealing a universal T7 forward oligo (95-4° C. at 5° C./minute) to the reverse complement ssDNA and filled in with Klenow fragment (New England Biolabs®) for 15 minutes at 25° C. The resulting IVT template is then transcribed into an RNA guide using the HiScribe T7 High Yield RNA Synthesis Kit (New England Biolabs®) at 37° C. for 4 hours. Following transcription, each RNA guide is purified using an RNA Clean and Concentrator Kit (Zymo) and stored at −20° C. until use.

The RNA guide is then labeled with 6-carboxyfluorescein (6-FAM) (IDT). 25 nM CRISPR nuclease polypeptide (wild-type or variant polypeptide) in 1λ assay buffer (20 mM Tris-HCl (pH 7.5), 150 mM KCl, 5 mM $MgCl_2$, 1 mM DTT) is titrated with increasing concentrations of labeled RNA guide (7.5-250 nM). Complexes are incubated at 37° C. for 30 minutes before taking fluorescence polarization measurements using a microplate reader (Infinite 200 Pro, Tecan).

Binary complex formation at different temperatures is also investigated. Further binding experiments as described above are performed isothermally at 25, 50, 60, and 70° C.

Formation of a binary complex upon titration of a CRISPR nuclease polypeptide (wild-type or variant polypeptide) with increasing concentrations of RNA guide (or formation of a binary complex upon titration of RNA guide with increasing concentrations of a CRISPR nuclease polypeptide) results in changes in fluorescence polarization signal, in millipolarization (mP) units. A binding curve is generated by plotting changes in fluorescence polarization signal over a range of RNA guide concentrations.

This Example indicates how binding affinities of CRISPR nuclease polypeptides (wild-type or variant polypeptide) to RNA guides can be determined and compared.

Example 3—RNA Electrophoretic Mobility Shift Assay for Variant Binary Complex Detection This Example describes use of an RNA electrophoretic mobility shift assay (EMSA) to determine the ability of a CRISPR nuclease polypeptide (wild-type or variant) to bind to an RNA guide.

Synthetic RNA guides from IDT™ are labeled with a 5' IRDye® 800CW using 5' EndTag Labeling Kit (Vector® Labs) and IRDyeR 800CW Maleimide (LI-COR® Biosciences), as previously detailed in Yan et al., 2018. After labeling, the RNA guides are cleaned and concentrated via phenol chloroform extraction. Concentrations are quantified by Nanodrop™.

For RNA binding assays, CRISPR nuclease polypeptides (wild-type or variant polypeptides) are diluted to 2.5 µM in 1λ binding buffer (50 mM NaCl, 10 mM Tris-HCl, 10 mM $MgCl_2$, 1 mM DTT, pH 7.9. Polypeptides are then serially diluted from 2.5 µM to 37.5 µM in 1λ binding buffer. The polypeptides are again diluted 1:10 in 1λ binding buffer plus 50 nM IR800 labeled RNA guide and mixed thoroughly. These reactions can further include 0.5-5 µg tRNA, which serves as a competitive inhibitor to decrease nonspecific binding of polypeptide to RNA and thereby facilitate accurate specific binding determinations. Reactions are incubated at 37° C. for 1 hour. 1 µL 100λ bromophenol blue is added to the reactions for dye front visualization, then the entire reaction is loaded onto a 6% DNA Retardation Gel (ThermoFisher®), which runs for 90 minutes at 80V. The gel is imaged on the Licor® Odyssey® CLx.

This assay relies on the principle that the rate at which RNA migrates through the gel is determined by its size. An RNA only sample is able to migrate a particular distance. However, if the RNA binds to a polypeptide, a band that represents a larger, less mobile RNA complex appears, which is "upshifted" on the gel.

Therefore, the intensities of two bands are measured: 1) an RNA only band and 2) a polypeptide-bound "upshifted" RNA band. If all RNA is bound to a polypeptide, only an upshifted band is observed. As the concentration of polypeptide decreases, the intensity of the upshifted band decreases, while the intensity of the RNA only band increases. In comparing RNA binding affinities for CRISPR nuclease polypeptides (wild-type or variant polypeptides), a higher polypeptide/RNA affinity is characterized by more specific binding at lower concentrations of polypeptide.

This Example indicates how binding affinities of wild-type CRISPR nuclease polypeptides to RNA guides and binding affinities of variant polypeptides to RNA guides can be determined and compared.

Example 4—In Vitro Cleavage Assay for Variant Binary Complexes

This Example describes methods for preparing CRISPR nuclease RNPs and for determining in vitro biochemical activity of CRISPR nuclease (wild-type or variant) RNPs.

CRISPR nuclease vectors are transformed into E. coli BL21 (DE3) (New England BioLabs®) and expressed under a T7 promoter. Transformed cells are initially grown overnight in 5 mL Luria Broth (Teknova)+50 µg/mL kanamycin, followed by inoculation into 1 L Terrific Broth media (Teknova)+50 µg/mL kanamycin. Cells are grown at 37° C. until an $OD_{600}$ of 0.6-0.8, then protein expression is induced with 0.5 mM IPTG. Cultures are then grown at 18° C. for an additional 14-18 hours. Cultures are harvested and pelleted via centrifugation, then resuspended in 1 mL extraction buffer per 5 g cell pellet (50 mM HEPES, pH 7.5, 500 mM NaCl, 5% glycerol, 0.5 mM TCEP). Cells are lysed via cell disruptor (Constant System Limited), then centrifuged at 20,000×g for 20 minutes at 4° C. in order to clarify the lysate. 0.2% polyethylenimine (PEI) is added to the clarified lysate and incubated at 4° C. with constant end-over-end rotation for 20 minutes. The lysate is then centrifuged again at 20,000×g for 10 minutes. The lysate is purified via ion exchange chromatography. After purification, fractions are run on SDS-PAGE gels, and fractions containing protein of the appropriate size are pooled and concentrated using 30 kD Amicon Ultra15 Centrifugal Units. Proteins are buffer exchanged into 12.5 mM HEPES pH 7.0, 120 mM NaCl, 0.5 mM TCEP, and 50% glycerol. Concentrations are then measured using the Nanodrop™ (ThermoFisher®), and proteins are stored at −20° C.

RNPs are prepared using a 2:1 ratio of synthetic crRNA (Integrated DNA Technologies) to protein. The RNPs are complexed for 30 minutes at 37° C. in 1×NEB2 buffer (50 mM NaCl, 10 mM Tris-HCl, 10 mM $MgCl_2$, 1 mM DTT, pH 7.9). After complexing, the RNPs are diluted using 1×NEB2 as a dilution buffer. Apo reactions (protein without RNA guide) are prepared in the same manner, making up the volume of crRNA with H$_2$O.

A target dsDNA substrate (Integrated DNA Technologies) is added at 20 nM to the RNP and apo samples. Reactions are mixed thoroughly then incubated at 37° C. for 1 hour, then quenched with 1 µL 20 mg/mL Proteinase K (ThermoFisher®). Reactions are incubated for another 15 minutes at 50° C., then the entire reaction is run on a 2% agarose E-gel (ThermoFisher®). Gels are visualized by ethidium bromide on a Gel Doc EZ Gel Imager (Bio-Rad®).

The intensities of two types of bands are measured: 1) a full-length (uncleaved) DNA band and 2) one or more downshifted cleaved DNA bands. An inactive RNP is characterized by a full-length DNA band. An active RNP yields one or more downshifted cleaved DNA bands. As the concentration of an active RNP decreases, the intensity of the full-length band increases, and the intensity of the cleaved band(s) decreases. In comparing activity of multiple RNPs, an RNP having higher activity than another is characterized by more intense cleaved bands at lower RNP concentrations.

The method of this Example allows for the comparison of in vitro cleavage activity of wild-type or variant CRISPR nuclease RNPs (binary complexes) on target DNA.

Example 5—In Vitro Stability Assays of Variant Polypeptides and Variant Binary Complexes In this Example, the stability of a variant RNP is assessed.

For the accelerated stability study, RNPs (5 µM) are generated in the same manner as described in Example 4, and the samples are subsequently stored at 25° C. for 48 hours.

In vitro cleavage assays (as described in Example 4) are performed on the RNP samples. These results are compared with those of Example 4 to determine the extent to which variant RNPs stored at 25° C. for 48 hours retain biochemical activity.

Apo polypeptide (without RNA guide) is also incubated at 25° C. for 48 hours. RNA EMSA assays are performed on the apo samples using the method described in Example 3. These results are compared with those of Example 3 to determine the extent to which a variant CRISPR nuclease is able to form a binary complex with an RNA guide.

Apo samples incubated at 25° C. for 48 hours are also complexed with RNA guides to form RNPs, using the method described in Example 4. In vitro cleavage assays are then performed according to the methods of Example 4. The assay results are compared with those of Example 4 to assess activity levels of variant RNPs formed with protein incubated at 25° C.

The methods of this Example allow for comparison of the stability of wild-type and variant polypeptides and wild-type and variant RNPs (binary complexes). A CRISPR nuclease polypeptide demonstrating greater specific binding to an RNA guide than another CRISPR nuclease polypeptide to the RNA guide is indicative of a more stable polypeptide. A CRISPR nuclease RNP demonstrating more robust in vitro cleavage of a target DNA than cleavage by another CRISPR nuclease polypeptide is indicative of a more stable binary complex.

Example 6—DNA Electrophoretic Mobility Shift Assay for Variant Ternary Complex Detection This Example describes use of a DNA EMSA to determine the ability of an RNA guide, a CRISPR nuclease polypeptide (wild-type or variant polypeptide), and a target DNA substrate to form a ternary complex.

CRISPR nuclease vectors are transformed into E. coli BL21 (DE3) (New England BioLabs®) and expressed under a T7 promoter. Transformed cells are initially grown overnight in 5 mL Luria Broth (Teknova)+50 µg/mL kanamycin, followed by inoculation into 1 L Terrific Broth media (Teknova)+50 µg/mL kanamycin. Cells are grown at 37° C. until an OD$_{600}$ of 0.6-0.8, then protein expression is induced with 0.5 mM IPTG. Cultures are then grown at 18° C. for an additional 14-18 hours. Cultures are harvested and pelleted via centrifugation, then resuspended in 1 mL extraction buffer per 5 g cell pellet (50 mM HEPES, pH 7.5, 500 mM NaCl, 5% glycerol, 0.5 mM TCEP). Cells are lysed via cell disruptor (Constant System Limited), then centrifuged at 20,000×g for 20 minutes at 4° C. in order to clarify the lysate. 0.2% polyethylenimine (PEI) is added to the clarified lysate and incubated at 4° C. with constant end-over-end rotation for 20 minutes. The lysate is then centrifuged again at 20,000×g for 10 minutes. The lysate is purified via ion exchange chromatography. After purification, fractions are run on SDS-PAGE gels, and fractions containing protein of the appropriate size are pooled and concentrated using 30 kD Amicon Ultra15 Centrifugal Units. Proteins are buffer exchanged into 12.5 mM HEPES pH 7.0, 120 mM NaCl, 0.5 mM TCEP, and 50% glycerol. Concentrations are then measured using the Nanodrop™ (ThermoFisher®) and proteins are stored at −20° C.

RNPs are prepared using a 2:1 ratio of synthetic RNA guide (Integrated DNA Technologies) to polypeptide. Targets adjacent to the PAM sequences disclosed herein are selected, and RNA guides are designed using a direct repeat sequence as described herein. The RNPs are complexed for 30 minutes at 37° C. in 1×NEB2 buffer (50 mM NaCl, 10 mM Tris-HCl, 10 mM MgCl$_2$, 1 mM DTT, pH 7.9). After complexing, a 5 point 1:2 serial dilution from 5 AM to 37.5 AM is performed, using 1×NEB2 as a dilution buffer. Apo reactions (polypeptide without RNA guide) are prepared in the same manner, making up the volume of RNA guide with H$_2$O.

dsDNA target substrates are generated by PCR from an oligo (Integrated DNA Technologies). Before PCR, the 5' end of the forward primer is labeled an IR800 dye, as described in Yan et al., 2018. Using Amplitaq Gold (ThermoFisher®), the dsDNA substrate is then amplified with the IR800 labeled forward primer and unlabeled reverse primer. The resulting dsDNA is purified with a DNA Clean and Concentrator®-5 Kit (Zymo Research) and quantified by Nanodrop™ (ThermoFisher®).

RNP samples and Apo (control) samples are diluted 1:10 into 1×binding buffer (50 mM NaCl, 10 mM Tris-HCl, 1 mM TCEP, 10% glycerol, 2 mM EDTA, pH 8.0) plus 20 nM IR800 labeled target DNA substrate and mixed thoroughly. Reactions are incubated at 37° C. for 1 hour. Bromophenol blue is added to the reactions for dye front visualization, then the entire reaction is loaded onto a 6% DNA Retardation Gel (ThermoFisher®), which ran for 90 minutes at 80V. The gel is imaged on the Licor® Odyssey® CLx.

In this assay, the rate at which DNA migrates through the gel is determined by its size. A DNA only sample is able to migrate a particular distance. However, if an RNP binds to the DNA, a band that represents a larger, less mobile DNA complex appears, which is "upshifted" on the gel.

This Example shows how the affinity of variant RNPs (variant binary complexes) to DNA targets (to produce a ternary complex) can be compared to the affinity of wild-type RNPs (wild-type binary complexes to the DNA targets.

Example 7—Editing of Mammalian Targets Using a 5'-CTG-3' PAM Sequence

This Example describes indel assessment on multiple target sequences adjacent to a 5'-CTG-3' PAM sequence.

The CRISPR nuclease of SEQ ID NO: 3 was cloned into a pcda3.1 backbone (Invitrogen™). RNA guides, each comprising the direct repeat sequence of SEQ ID NO: 6, were cloned into a pUC19 backbone (New England Biolabs®) under a U6 promoter. The plasmids were then maxi-prepped and diluted. The RNA guides (i.e., crRNA sequences of SEQ ID NOs: 9, 11, 13, 15, 17, 19, 21, and 23) and target sequences (i.e., SEQ ID NOs: 8, 10, 12, 14, 16, 18, 20, and 22) are shown in Table 4.

TABLE 4

Mammalian targets and corresponding crRNAs.

| Target identifier | Target sequence | crRNA sequence |
|---|---|---|
| AAVS1_T3 | GTGAACACCTAGGACGCAC CATTCT (SEQ ID NO: 8) | GGUCCCAUCGGAACGGGUUGUGGUUCCGA CGUGAACACCUAGGACGCACCAUUCU (SEQ ID NO: 9) |
| AAVS1_T5 | GCCCTGGCTTTGGCAGCCT GTGCTG (SEQ ID NO: 10) | GGUCCCAUCGGAACGGGUUGUGGUUCCGA CGCCCUGGCUUUGGCAGCCUGUGCUG (SEQ ID NO: 11) |
| EMX1_T6 | TGCCTGAAGTCGCCATCCA AAGCTT (SEQ ID NO: 12) | GGUCCCAUCGGAACGGGUUGUGGUUCCGA CUGCCUGAAGUCGCCAUCCAAAGCUU (SEQ ID NO: 13) |
| EMX1_T7 | AATAGTCCCTTGCTAAAGA AACATG (SEQ ID NO: 14) | GGUCCCAUCGGAACGGGUUGUGGUUCCGA CAAUAGUCCCUUGCUAAAGAAACAUG (SEQ ID NO: 15) |
| VEGFA_T3 | TGCTTTGTTGACATTGTCCA CACCT (SEQ ID NO: 16) | GGUCCCAUCGGAACGGGUUGUGGUUCCGA CUGCUUUGUUGACAUUGUCCACACCU (SEQ ID NO: 17) |
| VEGFA_T5 | AGTGCCCCCCCTTCTTGGG GGCTTT (SEQ ID NO: 18) | GGUCCCAUCGGAACGGGUUGUGGUUCCGA CAGUGCCCCCCCUUCUUGGGGGCUUU (SEQ ID NO: 19) |
| VEGFA_T6 | TACCTCTTTCCTTTGCCCAT ACTGG (SEQ ID NO: 20) | GGUCCCAUCGGAACGGGUUGUGGUUCCGA CUACCUCUUUCCUUUGCCCAUACUGG (SEQ ID NO: 21) |
| VEGFA_T7 | TGCCCATTGGTGGTCTGGA TAAAAG (SEQ ID NO: 22) | GGUCCCAUCGGAACGGGUUGUGGUUCCGA CUGCCCAUUGGUGGUCUGGAUAAAAG (SEQ ID NO: 23) |

Approximately 16 hours prior to transfection, 25,000 HEK293T cells in DMEM/10% FBS+Pen/Strep were plated into each well of a 96-well plate. On the day of transfection, the cells were 70-90% confluent. For each well to be transfected, a mixture of GeneJuice® transfection reagent (Millipore Sigma) and OptiMEM™ (ThermoFisher®) was prepared and then incubated at room temperature for 5 minutes (Solution 1). After incubation, the GeneJuice®:OptiMEM™ mixture was added to a separate solution comprising CRISPR nuclease plasmid and guide plasmid diluted in OptiMEM™ (Solution 2). In the case of negative controls, the crRNA was not included in Solution 2. The solution 1 and solution 2 mixtures were mixed by pipetting up and down and then incubated at room temperature for 5 minutes. Following incubation, Solution 1 and Solution 2 were added dropwise to each well of a 96 well plate containing the cells. 72 hours post transfection, cells were trypsinized by adding TrypLE™ (ThermoFisher®) to the center of each well and incubated for approximately 5 minutes. D10 media was then added to each well and mixed to resuspend cells. The cells were transferred to a 96-well PCR plate and spun down for 10 minutes. After centrifugation, supernatant was discarded, and the pellet was resuspended in 20 μL QuickExtract™ extraction reagent (Biosearch™ Technologies). The resuspended cell solution was incubated at 65° C. for 15 minutes, 68° C. for 15 minutes, and 98° C. for 10 minutes in a thermal cycler.

Samples for Next Generation Sequencing (NGS) were prepared by two rounds of PCR. The first round (PCR1) was used to amplify specific genomic regions depending on the target. PCR1 products were purified by column purification. Round 2 PCR (PCR2) was done to add Illumina adapters and indexes. Reactions were then pooled and purified by column purification. Sequencing runs were done with a 150 cycle NextSeq™ v2.5 mid or high output kit. Edited targets were defined as targets that showed indel levels above background (>0.5% in this assay).

FIG. 1 shows the percentage of NGS reads comprising an indel (% raw Indel). The average percent indels across eight different targets was 10.6%. This Example demonstrates that the CRISPR nuclease of SEQ ID NO: 3 and RNA guides comprising a direct repeat sequence of SEQ ID NO: 6 produce indels in target sequences adjacent to 5'-CTG-3' PAM sequences.

Example 8—Targeting of Mammalian Genes by CRISPR Nuclease Variants

This Example describes indel assessment on multiple targets using wild-type and variant effectors (e.g., CRISPR nuclease variants) introduced into mammalian cells by transient transfection.

CRISPR nucleases are cloned into a pcda3.1 backbone (Invitrogen™). The plasmids are then maxi-prepped and diluted to 1 µg/µL. Targets adjacent to the PAM sequences disclosed herein are selected, and RNA guides are designed using a direct repeat sequence as described herein. For RNA guide preparation, a dsDNA fragment encoding a crRNA is derived by ultramers containing the target sequence scaffold, and the U6 promoter. Ultramers are resuspended in 10 mM Tris.HCl at a pH of 7.5 to a final stock concentration of 100 µM. Working stocks are subsequently diluted to 10 µM, again using 10 mM Tris.HCl to serve as the template for the PCR reaction. The amplification of the crRNA is done in 50 µL reactions with the following components: 0.02 µl of aforementioned template, 2.5 µl forward primer, 2.5 µl reverse primer, 25 µL HiFi Polymerase (New England Biolabs®), and 20 µl water. Cycling conditions are: 1×(30s at 98° C.), 30×(10s at 98° C., 15s at 67° C.), 1×(2 min at 72° C.). PCR products are cleaned up with a 1.8×SPRI treatment and normalized to 25 ng/µL.

Approximately 16 hours prior to transfection, 100 µl of 25,000 HEK293T cells in DMEM/10% FBS+Pen/Strep are plated into each well of a 96-well plate. On the day of transfection, the cells are 70-90% confluent. For each well to be transfected, a mixture of 0.5 µl of Lipofectamine™ 2000 and 9.5 µl of OptiMEM™ is prepared and then incubated at room temperature for 5-20 minutes (Solution 1). After incubation, the Lipofectamine™: OptiMEM™ mixture is added to a separate mixture containing 182 ng of CRISPR nuclease plasmid and 14 ng of crRNA and water up to 10 µL (Solution 2). The solution 1 and solution 2 mixtures are mixed by pipetting up and down and then incubated at room temperature for 25 minutes. Following incubation, 20 µL of the Solution 1 and Solution 2 mixture are added dropwise to each well of a 96 well plate containing the cells. 72 hours post transfection, cells are trypsinized by adding 10 µL of TrypLE™ to the center of each well and incubated for approximately 5 minutes. 100 µL of D10 media is then added to each well and mixed to resuspend cells. The cells are then spun down at 500 g for 10 minutes, and the supernatant is discarded. QuickExtract™ buffer is added to ⅕ the amount of the original cell suspension volume. Cells are incubated at 65° C. for 15 minutes, 68° C. for 15 minutes, and 98° C. for 10 minutes.

Samples for Next Generation Sequencing are prepared by two rounds of PCR. The first round (PCR1) is used to amplify specific genomic regions depending on the target. PCR1 products are purified by column purification. Round 2 PCR (PCR2) is done to add Illumina adapters and indexes. Reactions are then pooled and purified by column purification. Sequencing runs are done with a 150 cycle NextSeq™ v2.5 mid or high output kit.

Edited targets are defined as targets that showed indel levels above background (>0.5% in this assay). Across the same target set, indels induced by the wild-type CRISPR nuclease and the variant CRISPR nuclease are compared to identify variant CRISPR nucleases having greater nuclease activity than the wild-type CRISPR nuclease.

Example 9—Targeting of Mammalian Genes by Variant Polypeptides

This Example describes indel assessment on multiple targets using variants introduced into mammalian cells by transient transfection.

Variants of SEQ ID NO: 3 (Tables 6-8) were cloned into a pcDNA3.1 backbone (Invitrogen®). RNA guides were cloned into a pUC19 backbone (New England Biolabs®). The plasmids were then maxi-prepped and diluted. The crRNA, target, and PAM sequences are listed in Table 5.

TABLE 5

Mammalian targets and corresponding crRNAs.

| Target | crRNA sequence | Target sequence | PAM sequence |
|---|---|---|---|
| AAVS1 | GGUCCCAUCGGAACGGGUU GUGGUUCCGACGGAGGGAU ACAUUGGUGGGG (SEQ ID NO: 24) | GGAGGGATACATTGGTGG GG (SEQ ID NO: 27) | 5'-GCTG-3' |
| VEGFA | GGUCCCAUCGGAACGGGUU GUGGUUCCGACAGGCCACA GGGACCCAACUG (SEQ ID NO: 25) | AGGCCACAGGGACCCAAC TG (SEQ ID NO: 28) | 5'-TCTC-3' |
| EMX1 | GGUCCCAUCGGAACGGGUU GUGGUUCCGACCGGCCAGU UUUUCCGUACGG (SEQ ID NO: 26) | CGGCCAGTTTTTCCGTACG G (SEQ ID NO: 29) | 5'-GCTC-3' |

Approximately 16 hours prior to transfection, 25,000 HEK293T cells in DMEM/10% FBS+Pen/Strep (D10 media) were plated into each well of a 96-well plate. On the day of transfection, the cells were 70-90% confluent. For each well to be transfected, a mixture of Lipofectamine™ 2000 (Invitrogen®) and Opti-MEM™ (Gibco™) was prepared and incubated at room temperature for 5 minutes (Solution 1). After incubation, the Lipofectamine 2000™: Opti-MEM™ mixture was added to a separate mixture containing nuclease plasmid, RNA guide plasmid, and Opti-MEM™ (Solution 2). In the case of negative controls, the RNA guide plasmid was not included in Solution 2. Solutions 1 and 2 were mixed by pipetting up and down, then incubated at room temperature for 25 minutes. Following incubation, the Solution 1 and 2 mixture was added dropwise to each well of a 96-well plate containing the cells. Approximately 72 hours post transfection, cells were trypsinized by adding TrypLE™ (Gibco™) to the center of each well and incubating at 37° C. for approximately 5 minutes. D10 media was then added to each well and mixed to resuspend cells. The resuspended cells were centrifuged at 500 g for 10 minutes to obtain a pellet, and the supernatant was discarded. The cell pellet was then resuspended in QuickExtract™ buffer (Lucigen®), and cells were incubated at 65° C. for 15 minutes, 68° C. for 15 minutes, and 98° C. for 10 minutes.

Samples for Next Generation Sequencing were prepared by two rounds of PCR. The first round (PCR1) was used to amplify specific genomic regions depending on the target. Round 2 PCR (PCR2) was performed to add Illumina adapters and indices. Reactions were then pooled and purified by column purification. Sequencing runs were performed using a 150 Cycle NextSeq 500/550 Mid or High Output v2.5 Kit (Illumina®).

TABLE 6

Exemplary single alterations increase indels relative to WT (averaged across 3 targets)

| Indels (Fold Increase) | Mutation | Indels (Fold Increase) | Mutation |
|---|---|---|---|
| 3.913 | D509R | 2.497 | L516K |
| 3.712 | S511R | 2.461 | Y381G |
| 3.572 | I521R | 2.450 | H532R |
| 3.568 | D535G | 2.438 | D129R |
| 3.532 | Q514G | 2.390 | P615R |
| 3.460 | L516R | 2.373 | G578R |
| 3.364 | L516G | 2.353 | M380G |
| 3.287 | E198R | 2.292 | V595G |
| 3.174 | S527R | 2.272 | R531G |
| 3.133 | D509K | 2.261 | D129G |
| 3.045 | D509G | 2.230 | R531K |

TABLE 6-continued

Exemplary single alterations increase indels relative to WT (averaged across 3 targets)

| Indels (Fold Increase) | Mutation | Indels (Fold Increase) | Mutation |
|---|---|---|---|
| 3.042 | L580G | 2.219 | D158G |
| 2.998 | V359R | 2.192 | N476G |
| 2.952 | D535K | 2.183 | G578K |
| 2.936 | Y381R | 2.170 | A512R |
| 2.906 | R354G | 2.165 | P618R |
| 2.883 | M380K | 2.164 | V595R |
| 2.819 | M380R | 2.163 | V595K |
| 2.788 | V383R | 2.140 | V383G |
| 2.726 | L580R | 2.131 | A597G |
| 2.714 | E367R | 2.130 | Y381K |
| 2.714 | I521K | 2.129 | P618G |
| 2.658 | E367G | 2.087 | E198K |
| 2.657 | E507R | 2.087 | T288R |
| 2.653 | I521G | 2.079 | E507K |
| 2.649 | W350R | 2.065 | L385R |
| 2.580 | D535R | 2.057 | C538G |
| 2.557 | R528K | 2.035 | P615G |
| 2.554 | S527K | 2.013 | D386R |
| 2.540 | L385G | 2.012 | S511K |
| 2.505 | W350G | 2.000 | C371G |

TABLE 7

Exemplary double alterations increase indels relative to WT (averaged across 3 targets)

| Indels (fold increase) | Mutation | Indels (fold increase) | Mutation | Indels (fold increase) | Mutation |
|---|---|---|---|---|---|
| 3.902 | L580G, L385G | 2.942 | D509R, L385G | 2.533 | I521R, D386R |
| 3.751 | L580G, A512R | 2.939 | I521R, P618R | 2.532 | Y381R, D129R |
| 3.703 | S527R, C538G | 2.935 | S511R, V383R | 2.524 | V383R, N476G |
| 3.697 | D129R, P618R | 2.932 | L385G, A512R | 2.518 | M380R, P615R |
| 3.665 | Q514G, A512R | 2.924 | D509R, P618R | 2.512 | E507R, A597G |
| 3.633 | S527R, L385G | 2.921 | Y381R, L385G | 2.511 | S527R, E507R |
| 3.632 | G578R, D158G | 2.921 | E367R, L385G | 2.509 | I521R, D129R |
| 3.610 | S511R, P618R | 2.919 | Q514G, D129R | 2.507 | Q514G, V359R |
| 3.589 | D158G, A512R | 2.918 | E198R, E367R | 2.504 | Y381R, A597G |
| 3.582 | R354G, A512R | 2.918 | D129R, C371G | 2.498 | S511R, D535G |
| 3.580 | A512R, P618R | 2.916 | S527R, D386R | 2.497 | L580G, D158G |
| 3.567 | V359R, A512R | 2.915 | Q514G, E507R | 2.496 | D509R, D158G |
| 3.548 | E367R, A512R | 2.915 | V359R, L385G | 2.493 | E198R, D129R |
| 3.520 | Q514G, N476G | 2.914 | M380R, L385G | 2.492 | L385G, V595G |
| 3.504 | S511R, A512R | 2.914 | Q514G, R354G | 2.483 | P615R, T288R |
| 3.496 | E198R, R354G | 2.911 | E198R, Y381R | 2.479 | M380R, P618R |
| 3.475 | Q514G, C538G | 2.911 | M380R, D129R | 2.476 | V383R, C371G |
| 3.468 | S527R, T288R | 2.906 | L580G, D129R | 2.472 | D509R, N476G |
| 3.451 | R354G, D158G | 2.905 | D129R, G578R | 2.460 | M380R, T288R |
| 3.439 | R354G, L385G | 2.895 | S511R, A597G | 2.459 | S511R, S527R |
| 3.437 | G578R, A512R | 2.895 | D535G, D158G | 2.454 | D158G, T288R |
| 3.425 | R354G, E507R | 2.894 | N476G, A512R | 2.447 | Q514G, S527R |
| 3.424 | S527R, G578R | 2.893 | Q514G, L516G | 2.446 | L516R, Y381R |
| 3.422 | S511R, C538G | 2.892 | E507R, P618R | 2.443 | R354G, E367R |
| 3.417 | I521R, V383R | 2.888 | V383R, D129R | 2.440 | A512R, T288R |
| 3.402 | S511R, I521R | 2.887 | L385G, C538G | 2.437 | V359R, D386R |
| 3.401 | L385G, G578R | 2.880 | I521R, D158G | 2.435 | S527R, V595G |
| 3.393 | L580G, N476G | 2.875 | L516R, L580G | 2.425 | D509R, A512R |
| 3.383 | Q514G, T288R | 2.872 | S527R, D158G | 2.424 | D535G, Q514G |
| 3.377 | D535G, A512R | 2.871 | H532R, A512R | 2.424 | W350R, N476G |
| 3.347 | D509R, M380R | 2.869 | I521R, R354G | 2.422 | S511R, D129R |
| 3.347 | S527R, C371G | 2.867 | I521R, Y381R | 2.413 | V359R, P615R |
| 3.339 | Q514G, D158G | 2.866 | D129R, P615R | 2.413 | I521R, P615R |
| 3.336 | E198R, C538G | 2.853 | V359R, E507R | 2.408 | M380R, A597G |
| 3.332 | S511R, L385G | 2.853 | E507R, G578R | 2.408 | E367R, D386R |
| 3.317 | S527R, N476G | 2.847 | L516R, P618R | 2.404 | M380R, D386R |
| 3.316 | L516R, A512R | 2.846 | R354G, M380R | 2.400 | L516R, S527R |
| 3.302 | S511R, C371G | 2.842 | R354G, D386R | 2.396 | L385G, D386R |
| 3.295 | L516R, C538G | 2.835 | I521R, G578R | 2.395 | V383R, T288R |
| 3.290 | E198R, C371G | 2.833 | Y381R, A512R | 2.392 | V359R, M380R |
| 3.272 | Q514G, V383R | 2.826 | A512R, D386R | 2.388 | L385G, H532R |
| 3.250 | L516R, N476G | 2.822 | M380R, G578R | 2.388 | S511R, V359R |

TABLE 7-continued

Exemplary double alterations increase indels relative to WT (averaged across 3 targets)

| Indels (fold increase) | Mutation | Indels (fold increase) | Mutation | Indels (fold increase) | Mutation |
|---|---|---|---|---|---|
| 3.249 | D509R, T288R | 2.815 | Y381R, E507R | 2.381 | R354G, P615R |
| 3.247 | D509R, G578R | 2.815 | L580G, E507R | 2.379 | L516R, A597G |
| 3.245 | D158G, C371G | 2.813 | V359R, Y381R | 2.379 | E507R, D386R |
| 3.242 | I521R, N476G | 2.811 | P615R, N476G | 2.377 | I521R, A597G |
| 3.239 | E198R, M380R | 2.808 | D158G, N476G | 2.370 | V595G, D386R |
| 3.238 | D129R, N476G | 2.797 | Y381R, P615R | 2.370 | N476G, P618R |
| 3.227 | M380R, A512R | 2.795 | V595G, A512R | 2.365 | E367R, D129R |
| 3.223 | R354G, D129R | 2.791 | V383R, D158G | 2.363 | D535G, M380R |
| 3.223 | S527R, L580G | 2.791 | E507R, D158G | 2.361 | S527R, H532R |
| 3.222 | R354G, N476G | 2.790 | V383R, C538G | 2.356 | D509R, I521R |
| 3.217 | Q514G, P618R | 2.789 | V383R, E507R | 2.356 | E198R, V595G |
| 3.213 | V383R, L385G | 2.787 | E198R, D386R | 2.355 | E198R, D158G |
| 3.209 | E198R, V359R | 2.783 | D129R, D386R | 2.352 | D509R, A597G |
| 3.198 | D535G, N476G | 2.783 | M380R, D158G | 2.351 | A597G, T288R |
| 3.196 | Q514G, L385G | 2.778 | E198R, P618R | 2.346 | D509R, D129R |
| 3.191 | S511R, N476G | 2.765 | Q514G, E198R | 2.345 | P615R, A597G |
| 3.189 | D158G, A597G | 2.763 | I521R, S527R | 2.338 | S511R, E367R |
| 3.189 | L516R, G578R | 2.762 | E198R, A512R | 2.337 | L516R, E198R |
| 3.189 | E198R, L580G | 2.761 | L385G, C371G | 2.333 | D535G, A597G |
| 3.186 | E198R, L385G | 2.761 | H532R, C538G | 2.332 | H532R, D158G |
| 3.184 | L580G, V383R | 2.760 | N476G, C371G | 2.328 | H532R, D129R |
| 3.180 | I521R, C371G | 2.759 | Y381R, N476G | 2.325 | D535G, Y381R |
| 3.179 | V359R, R354G | 2.758 | M380R, V383R | 2.317 | E507R, T288R |
| 3.178 | Y381R, G578R | 2.752 | H532R, T288R | 2.314 | H532R, G578R |
| 3.178 | E198R, V383R | 2.751 | Q514G, D386R | 2.313 | D509R, L516R |
| 3.157 | L580G, D386R | 2.750 | R354G, T288R | 2.310 | G578R, A597G |
| 3.156 | L385G, P615R | 2.750 | Y381R, D158G | 2.308 | L580G, A597G |
| 3.153 | V383R, G578R | 2.733 | M380R, E507R | 2.308 | R531G, C371G |
| 3.150 | D535G, T288R | 2.725 | P615R, C371G | 2.300 | D535G, C371G |
| 3.146 | Y381R, P618R | 2.722 | S527R, D129R | 2.297 | E507R, N476G |
| 3.143 | A512R, A597G | 2.721 | M380R, C538G | 2.296 | L516R, H532R |
| 3.141 | Q514G, L580G | 2.720 | L580G, R354G | 2.291 | V383R, A597G |
| 3.139 | S527R, P615R | 2.719 | L385G, T288R | 2.289 | G578R, V595G |
| 3.134 | E198R, P615R | 2.714 | L580G, G578R | 2.285 | D509R, Y381R |
| 3.129 | I521R, T288R | 2.713 | E507R, L385G | 2.282 | D158G, P618R |
| 3.125 | Y381R, C538G | 2.711 | E507R, P615R | 2,280 | P618R, C538G |
| 3.122 | S527R, A512R | 2.710 | E198R, E507R | 2.276 | P618R, C371G |
| 3.121 | Y381R, C371G | 2.708 | S511R, D158G | 2.269 | N476G, D386R |
| 3.121 | I521R, L385G | 2.708 | G578R, P618R | 2.269 | V359R, P618R |
| 3.118 | L516R, T288R | 2.705 | D509R, P615R | 2.265 | D509R, Q514G |
| 3.117 | L516R, D158G | 2.692 | D158G, D386R | 2.262 | H532R, D386R |
| 3.113 | S527R, P618R | 2.691 | I521R, Q514G | 2.261 | L580G, W350R |
| 3.112 | S527R, R354G | 2.690 | D535G, D386R | 2.242 | S527R, V359R |
| 3.105 | Y381R, V383R | 2.690 | P615R, D386R | 2.241 | T288R, C371G |
| 3.104 | A512R, C371G | 2.688 | D535G, G578R | 2.241 | I521R, H532R |
| 3.098 | S511R, T288R | 2.683 | D535G, S527R | 2.239 | W350R, A512R |
| 3.098 | S511R, Q514G | 2.681 | Y381R, D386R | 2.232 | V595G, D158G |
| 3.096 | L516R, V383R | 2.678 | D129R, D158G | 2.232 | Y381R, M380R |
| 3.091 | A512R, C538G | 2.676 | Q514G, G578R | 2.230 | M380R, R531G |
| 3.088 | I521R, M380R | 2.675 | L516R, D129R | 2.230 | D535G, L516R |
| 3.088 | D535G, C538G | 2.673 | L385G, D129R | 2.227 | M380R, C371G |
| 3.084 | E198R, T288R | 2.671 | L385G, D158G | 2.215 | V595G, C538G |
| 3.083 | Q514G, M380R | 2.664 | E198R, H532R | 2.209 | L516R, R354G |
| 3.082 | S527R, V383R | 2.655 | Q514G, C371G | 2.206 | D129R, V595G |
| 3.081 | L580G, Y381R | 2.652 | G578R, D386R | 2.199 | D509R, S527R |
| 3.077 | S511R, G578R | 2.651 | R354G, A597G | 2.187 | V383R, P615R |
| 3.074 | Y381R, R354G | 2.646 | Q514G, A597G | 2.186 | Y381R, H532R |
| 3.071 | L516R, L385G | 2.644 | E367R, E507R | 2.179 | D129R, A597G |
| 3.059 | D535G, E198R | 2.637 | L580G, C371G | 2.176 | L516R, R531G |
| 3.058 | S527R, M380R | 2.634 | E367R, G578R | 2.165 | D386R, C371G |
| 3.057 | L580G, M380R | 2.630 | L516R, M380R | 2.165 | H532R, C371G |
| 3.051 | N476G, A597G | 2.627 | H532R, N476G | 2.164 | W350R, C538G |
| 3.048 | I521R, C538G | 2.623 | V359R, D129R | 2.163 | V383R, W350R |
| 3.047 | R354G, G578R | 2.620 | S511R, P615R | 2.155 | P615R, P618R |
| 3.044 | S511R, D386R | 2.618 | Q514G, Y381R | 2.147 | S511R, H532R |
| 3.034 | P615R, C538G | 2.613 | M380R, N476G | 2.143 | R354G, P618R |
| 3.034 | L580G, T288R | 2.613 | Q514G, P615R | 2.142 | G578R, R531G |
| 3.033 | E507R, C538G | 2.613 | D158G, C538G | 2.137 | E367R, D158G |
| 3.030 | E198R, A597G | 2.610 | Y381R, E367R | 2.135 | V359R, A597G |
| 3.027 | P615R, G578R | 2.609 | I521R, E507R | 2.130 | L580G, P618R |
| 3.022 | S511R, R354G | 2.608 | I521R, L516R | 2.126 | I521R, W350R |
| 3.021 | D509R, D386R | 2.607 | L385G, N476G | 2.114 | W350R, G578R |
| 3.019 | S511R, L580G | 2.606 | E198R, N476G | 2.111 | Q514G, E367R |
| 3.014 | E198R, S527R | 2.605 | R531G, T288R | 2.111 | S511R, V595G |
| 3.012 | V359R, G578R | 2.603 | Y381R, T288R | 2.109 | C538G, D386R |

TABLE 7-continued

Exemplary double alterations increase indels relative to WT (averaged across 3 targets)

| Indels (fold increase) | Mutation | Indels (fold increase) | Mutation | Indels (fold increase) | Mutation |
|---|---|---|---|---|---|
| 3.005 | I521R, A512R | 2.595 | Y381R, V595G | 2.107 | A597G, D386R |
| 3.001 | D509R, C538G | 2.592 | P615R, D158G | 2.104 | H532R, P615R |
| 3.001 | L385G, P618R | 2.592 | D509R, E198R | 2.099 | V359R, V595G |
| 2.997 | P615R, A512R | 2.591 | E507R, V595G | 2.094 | M380R, H532R |
| 2.990 | V383R, A512R | 2.582 | L580G, P615R | 2.093 | W350R, P618R |
| 2.985 | L580G, C538G | 2.582 | D509R, L580G | 2.085 | H532R, P618R |
| 2.984 | G578R, C538G | 2.580 | V359R, D158G | 2.080 | Q514G, H532R |
| 2.981 | D535R, L385G | 2.578 | S527R, Y381R | 2.062 | L580G, H532R |
| 2.980 | L516R, D386R | 2.577 | D509R, C371G | 2.061 | W350R, T288R |
| 2.978 | L516R, E507R | 2.573 | E198R, G578R | 2.059 | D509R, E507R |
| 2.975 | S511R, Y381R | 2.565 | D535G, D129R | 2.057 | P618R, D386R |
| 2.972 | G578R, N476G | 2.561 | L516R, P615R | 2.057 | E507R, W350R |
| 2.966 | E507R, C371G | 2.557 | D129R, T288R | 2.044 | A597G, C538G |
| 2.966 | G578R, T288R | 2.556 | R354G, V383R | 2.039 | S511R, L516R |
| 2.963 | L385G, A597G | 2.555 | E507R, D129R | 2.035 | W350R, L385G |
| 2.963 | I521R, D535R | 2.553 | E507R, A512R | 2.034 | W350R, D158G |
| 2.955 | S527R, A597G | 2.551 | N476G, C538G | 2.033 | P618R, A597G |
| 2.950 | I521R, E198R | 2.546 | I521R, L580G | 2.031 | Q514G, V595G |
| 2.949 | S511R, E198R | 2.542 | L516R, C371G | 2.026 | E198R, W350R |
| 2.949 | S511R, M380R | 2.539 | D535G, L580G | 2.019 | D509R, V383R |
| 2.945 | S511R, E507R | 2.539 | D535G, E507R | 2.008 | D509R, R354G |
| 2.945 | D129R, A512R | 2.537 | D129R, C538G | | |
| 2.942 | G578R, C371G | 2.534 | R354G, C538G | | |

TABLE 8

Exemplary alterations increase indels relative to WT (averaged across 3 targets)

| Indels relative to WT | Mutation |
|---|---|
| 3.589 | D535G, L516R, I521R |
| 3.572 | L516R, Q514G, I521R |
| 3.396 | D509R, L516R, I521R |
| 3.255 | D535G, L516R, Q514G |
| 3.050 | D535G, Q514G, I521R |
| 2.907 | Q514G, I521R, L580G, E198R |
| 2.871 | D535G, Q514G, I521R, E198R |
| 2.798 | D535G, L516R, Q514G, I521R |
| 2.760 | Q514G, I521R, S527R, E198R |
| 2.741 | D509R, D535G, L516R, Q514G, I521R |
| 2.707 | D535G, L516R, I521R, S527R |
| 2.707 | D535G, I521R, L580G, E198R |
| 2.687 | D509R, D535G, L516R |
| 2.683 | I521R, S527R, E198R, M380R |
| 2.665 | D509R, L516R, Q514G |
| 2.653 | D509R, Q514G, I521R |
| 2.650 | D535G, L516R, Q514G, S511R |
| 2.540 | D535G, L516R, Q514G, S527R |
| 2.516 | I521R, S527R, L580G, E198R |
| 2.514 | D535G, L516R, S527R, M380R |
| 2.512 | Q514G, S527R, L580G, E198R |
| 2.445 | L516R, Q514G, I521R, M380R |
| 2.430 | D509R, L516R, Q514G, S527R |
| 2.418 | D509R, I521R, L580G, E198R |
| 2.366 | S527R, L580G, E198R, M380R |
| 2.357 | L516R, S527R, L580G, E198R |
| 2.346 | D509R, Q514G, I521R, E198R |
| 2.330 | D535G, Q514G, I521R, S527R |
| 2.311 | Q514G, L580G, E198R, M380R |
| 2.308 | D509R, L516R, I521R, E198R |
| 2.308 | L516R, Q514G, I521R, L580G |
| 2.269 | D509R, D535G, Q514G, E198R |
| 2.253 | L516R, I521R, S527R, L580G |
| 2.239 | D535G, I521R, S527R, M380R |
| 2.230 | L516R, I521R, L580G, E198R |
| 2.206 | D509R, D535G, I521R |
| 2.206 | D535G, S527R, L580G, E198R |
| 2.141 | D509R, D535G, Q514G |
| 2.119 | S527R, L580G, E198R, R354G |
| 2.116 | Q514G, I521R, S527R, L580G |
| 2.105 | D535G, Q514G, E198R, M380R |

TABLE 8-continued

Exemplary alterations increase indels relative to WT (averaged across 3 targets)

| Indels relative to WT | Mutation |
|---|---|
| 2.100 | L516R, Q514G, L580G, E198R |
| 2.091 | I521R, S527R, E198R, R354G |
| 2.064 | I521R, S527R, R354G, M380R |
| 2.061 | I521R, L580G, E198R, M380R |
| 2.054 | L516R, Q514G, S527R, L580G |
| 2.016 | D535G, Q514G, S527R, E198R |
| 2.015 | D509R, Q514G, L580G, E198R |

As shown in Tables 6-8, multiple variants comprising either a single amino acid substitution, such as D509R, or two to five amino acid substitutions, such as L580G and L385G, resulted in an increase in indel activity of at least 2-fold.

Example 10—Targeting of Mammalian Genes by Variant Polypeptides

This Example describes indel assessment on multiple targets using a variant polypeptide introduced into mammalian cells by transient transfection.

Using the assay and three targets described in Example 9, additional combination variants of SEQ ID NO: 3 were analyzed. The combination mutations resulting in at least a 2-fold increase in indel activity, such as K136G, N220R, and M380R, are shown in Table 9.

TABLE 9

Exemplary alterations increase indels relative to WT (averaged across 3 targets)

| Indels relative to WT | Mutation |
|---|---|
| 4.535 | K136G, N220R, M380R |
| 4.138 | S78K, E198R, R354G |
| 4.001 | K141G, N220R, M380R |

TABLE 9-continued

Exemplary alterations increase indels relative to WT (averaged across 3 targets)

| Indels relative to WT | Mutation |
| --- | --- |
| 4.001 | K141G, K240R, M380R |
| 3.727 | K141G, D277R, M380R |
| 3.411 | K136G, D277R, M380R |
| 3.347 | S78K, E198R, L385R |
| 3.330 | L580G, L385G, S511R, A512R |
| 3.266 | S78K, E198R, M380R |
| 3.193 | K136G, K240R, M380R |
| 3.107 | T165R, N220R, M380R |
| 3.088 | L580G, L385G, Q514G, A512R |
| 3.056 | D129R, P618R, S511R, A512R |
| 2.928 | S78K, E198R, K374R |
| 2.865 | T165R, D277R, M380R |
| 2.827 | L580G, L385G, G578R, D158G |
| 2.786 | D129R, P618R, R354G, A512R |
| 2.775 | T165R, K240R, M380R |
| 2.764 | K141G, K240R, L385R |
| 2.755 | K136G, N220R, L385R |
| 2.743 | D129R, P618R, Q514G, A512R |
| 2.718 | D129R, P618R, S527R, L385G |
| 2.637 | K141G, N220R, L385R |
| 2.533 | L580G, L385G, Q514G, N476G |
| 2.519 | L580G, L385G, A512R, P618R |
| 2.360 | K141G, D277R, L385R |
| 2.316 | D129R, P618R, D158G, A512R |
| 2.265 | K136G, N220R, K374R |
| 2.259 | K136G, D277R, L385R |
| 2.193 | K136G, K240R, L385R |
| 2.148 | L580G, L385G, S527R, C538G |
| 2.138 | T165R, K240R, L385R |
| 2.114 | D129R, P618R, V359R, A512R |

ENUMERATED EMBODIMENTS

The following enumerated embodiments are provided, the numbering of which is not to be construed as designating levels of importance.

Embodiment 1 provides a variant polypeptide, or a composition comprising a variant polypeptide, wherein the variant polypeptide comprises an alteration relative to a parent polypeptide, wherein the parent polypeptide comprises SEQ ID NO: 3, wherein the variant polypeptide is capable of binding to an RNA guide and a target nucleic acid, and wherein the variant polypeptide or a complex comprising the variant polypeptide exhibits enhanced enzymatic activity, enhanced binding activity, enhanced binding specificity, and/or enhanced stability relative to the parent polypeptide or a complex comprising the parent polypeptide.

Embodiment 2 provides the variant polypeptide or composition of embodiment 1, wherein the enhanced enzymatic activity is enhanced nuclease activity.

Embodiment 3 provides the variant polypeptide or composition of any previous embodiment, wherein the variant polypeptide exhibits enhanced binding activity to the RNA guide relative to the parent polypeptide.

Embodiment 4 provides the variant polypeptide or composition of any previous embodiment, wherein the variant polypeptide exhibits enhanced binding specificity to the RNA guide relative to the parent polypeptide.

Embodiment 5 provides the variant polypeptide or composition of any previous embodiment, wherein the variant polypeptide and the RNA guide form a variant binary complex, and the variant binary complex exhibits one or more of the following features:

(i) enhanced binding activity to the target nucleic acid (e.g., on-target binding activity) relative to a parent binary complex;

(ii) enhanced binding specificity to the target nucleic acid (e.g., on-target binding specificity) relative to a parent binary complex;

(iii) enhanced stability relative to a parent binary complex; and/or (iv) decreased dissociation from the target nucleic acid, and/or decreased off-target binding to a non-target nucleic acid relative to the parent binary complex.

Embodiment 6 provides the variant polypeptide or composition of any previous embodiment, wherein the variant binary complex and the target nucleic acid form a variant ternary complex, and the variant ternary complex exhibits increased stability relative to a parent ternary complex.

Embodiment 7 provides the variant polypeptide or composition of any previous embodiment, wherein the variant polypeptide further exhibits enhanced binary complex formation, enhanced protein-RNA interactions, and/or decreased dissociation from the RNA guide relative to the parent polypeptide.

Embodiment 8 provides the variant polypeptide or composition of any previous embodiment, wherein the enhanced enzymatic activity, enhanced binding activity, enhanced binding specificity, and/or enhanced stability occur over a range of temperatures, e.g., 20° C. to 65° C.

Embodiment 9 provides the variant polypeptide or composition of any previous embodiment, wherein the enhanced enzymatic activity, enhanced binding activity, enhanced binding specificity, and/or enhanced stability occur over a range of incubation times.

Embodiment 10 provides the variant polypeptide or composition of any previous embodiment, wherein the enhanced enzymatic activity, enhanced binding activity, enhanced binding specificity, and/or enhanced stability occur in a buffer having a pH in a range of about 7.3 to about 8.6.

Embodiment 11 provides the variant polypeptide or composition of any previous embodiment, wherein the enhanced enzymatic activity, enhanced binding activity, enhanced binding specificity, and/or enhanced stability occurs when a Tm value of the variant polypeptide, variant binary complex, or variant ternary complex is at least 8° C. greater than the Tm value of the parent polypeptide, parent binary complex, or parent ternary complex.

Embodiment 12 provides the variant polypeptide or composition of any previous embodiment, wherein the alteration is at least one amino acid substitution listed in Table 2.

Embodiment 13 provides the variant polypeptide or composition of any previous embodiment, wherein the alteration is an arginine, lysine, glutamine, asparagine, histidine, alanine, or glycine substitution.

Embodiment 14 provides the variant polypeptide or composition of any previous embodiment, wherein the variant polypeptide comprises a RuvC domain or a split RuvC domain.

Embodiment 15 provides the variant polypeptide or composition of any previous embodiment, wherein the variant polypeptide comprises one or more catalytic residues (e.g., aspartic acid or glutamic acid).

Embodiment 16 provides the variant polypeptide or composition of any previous embodiment, wherein the one or more catalytic residues comprise D345 and E506.

Embodiment 17 provides the variant polypeptide or composition of any previous embodiment, wherein the RNA guide comprises a direct repeat sequence and a spacer sequence.

Embodiment 18 provides the variant polypeptide or composition of any previous embodiment, wherein the direct repeat sequence comprises a nucleotide sequence with at least 90% sequence identity to SEQ ID NO: 4, SEQ ID NO: 5, or SEQ ID NO: 6.

Embodiment 19 provides the variant polypeptide or composition of any previous embodiment, wherein the direct repeat sequence comprises a nucleotide sequence with at least 95% sequence identity to SEQ ID NO: 4, SEQ ID NO: 5, or SEQ ID NO: 6.

Embodiment 20 provides the variant polypeptide or composition of any previous embodiment, wherein the direct repeat sequence comprises SEQ ID NO: 4, SEQ ID NO: 5, or SEQ ID NO: 6.

Embodiment 21 provides the variant polypeptide or composition of any previous embodiment, wherein the spacer sequence comprises between 15 and 35 nucleotides in length.

Embodiment 22 provides the variant polypeptide or composition of any previous embodiment, wherein the RNA guide comprises any one of SEQ ID NOs: 9, 11, 13, 15, 17, 19, 21, and 23.

Embodiment 23 provides the variant polypeptide or composition of any previous embodiment, wherein the target nucleic acid comprises a sequence complementary to a nucleotide sequence in the spacer sequence.

Embodiment 24 provides the variant polypeptide or composition of any previous embodiment, wherein the target nucleic acid is adjacent to a protospacer adjacent motif (PAM) sequence, wherein the PAM sequence comprises a nucleotide sequence set forth as 5'-NTN-3', 5'-HTN-3', or 5'-TNA-3', wherein N is any nucleotide and His A or C or T.

Embodiment 25 provides the variant polypeptide or composition of embodiment 24, wherein the PAM sequence comprises a nucleotide sequence set forth as 5'-CTG-3'.

Embodiment 26 provides the variant polypeptide or composition of any previous embodiment, wherein the target nucleic acid is single-stranded DNA or double-stranded DNA.

Embodiment 27 provides the variant polypeptide or composition of any previous embodiment, wherein the variant polypeptide further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

Embodiment 28 provides the variant polypeptide or composition of any previous embodiment, wherein a nucleic acid encoding the variant polypeptide is codon-optimized for expression in a cell.

Embodiment 29 provides the variant polypeptide or composition of embodiment 28, wherein the nucleic acid encoding the variant polypeptide is operably linked to a promoter.

Embodiment 30 provides the variant polypeptide or composition of any previous embodiment, wherein the nucleic acid encoding the variant polypeptide is in a vector.

Embodiment 31 provides the variant polypeptide or composition of embodiment 31, wherein the vector comprises a retroviral vector, a lentiviral vector, a phage vector, an adenoviral vector, an adeno-associated vector, or a herpes simplex vector.

Embodiment 32 provides the variant polypeptide or composition of any previous embodiment, wherein the composition is present in a delivery composition comprising a nanoparticle, a liposome, an exosome, a microvesicle, or a gene-gun.

Embodiment 33 provides the a cell comprising the variant polypeptide or composition of any previous embodiment.

Embodiment 34 provides the cell of embodiment 33, wherein the cell is a eukaryotic cell or a prokaryotic cell.

Embodiment 35 provides the cell of any previous embodiment, wherein the cell is a mammalian cell or a plant cell.

Embodiment 36 provides the cell of any previous embodiment, wherein the cell is a human cell.

Embodiment 37 provides an RNA guide or a nucleic acid encoding the RNA guide, wherein the RNA guide comprises a direct repeat sequence and a spacer sequence, and wherein the direct repeat sequence comprises a nucleotide sequence having at least 90% identity to any one of SEQ ID NOs: 4-6.

Embodiment 38 provides the RNA guide or the nucleic acid encoding the RNA guide of embodiment 42, wherein the direct repeat sequence is selected from the group consisting of SEQ ID NOs: 4-6.

Embodiment 39 provides the RNA guide or the nucleic acid encoding the RNA guide of any one of embodiments 40 or 41, wherein the spacer sequence binds adjacent to a 5'-CTG-3' protospacer adjacent motif.

Embodiment 40 provides the RNA guide or the nucleic acid encoding the RNA guide of any one of embodiments 40-42, wherein the RNA guide comprises a nucleotide sequence of any one of SEQ ID NOs: 9, 11, 13, 15, 17, 19, 21, and 23.

Embodiment 41 provides a composition comprising the RNA guide or the nucleic acid encoding the RNA guide of any one of embodiment 37-40.

Embodiment 42 provides the composition of embodiment 41, wherein the composition further comprises a CRISPR nuclease or a nucleic acid encoding the CRISPR nuclease.

Embodiment 43 provides the composition of embodiment 42, wherein the CRISPR nuclease comprises an amino acid sequence having at least 80% identity to SEQ ID NO: 3.

Embodiment 44 provides the composition of embodiment 43, wherein the CRISPR nuclease comprises an amino acid sequence having at least 95% identity to SEQ ID NO: 3.

Embodiment 45 provides the composition of any one of embodiments 41-44, wherein the CRISPR nuclease is the variant polypeptide of any one of embodiments 1-32.

Embodiment 46 provides a method of preparing the variant polypeptide of any previous embodiment, the method comprising (i) introducing one or more nucleotide substitutions into a nucleic acid comprising SEQ ID NO: 1 or SEQ ID NO: 2 to produce a variant nucleic acid which encodes the variant polypeptide, and (ii) expressing the variant polypeptide from the variant nucleic acid.

Embodiment 47 provides a variant binary complex comprising the variant polypeptide of any previous embodiment and an RNA guide.

Embodiment 48 provides a variant ternary complex comprising the variant polypeptide of any previous embodiment, an RNA guide, and a target nucleic acid.

Embodiment 49 provides a method of forming a variant binary complex, the method comprising contacting the variant polypeptide of any previous embodiment with the RNA guide of any previous embodiment.

Embodiment 50 provides a method of forming a variant ternary complex, the method comprising contacting the variant polypeptide of any previous embodiment with the RNA guide of any previous embodiment and the target nucleic acid of any previous embodiment.

Embodiment 51 provides a method of delivering the variant polypeptide or composition or the variant binary complex of any previous embodiment to a cell, the method comprising introducing into the cell the variant polypeptide of any one of embodiments 1-32 or a nucleic acid encoding the variant polypeptide, and optionally, introducing the RNA guide or the nucleic acid encoding the RNA guide of any previous embodiment, or introducing the variant binary complex of embodiment 5, wherein the introducing comprises introducing a nanoparticle, a liposome, an exosome, a microvesicle, a viral vector, or any combination thereof.

Embodiment 52 provides a method for modifying a target DNA molecule in a cell, the method comprising introducing into the cell the variant polypeptide of any one of embodiments 1-32 or a nucleic acid encoding the variant polypeptide, and introducing the RNA guide or the nucleic acid encoding the RNA guide of any previous embodiment, or introducing the variant binary complex of embodiment 47, wherein the introducing comprises introducing a nanoparticle, a liposome, an exosome, a microvesicle, a viral vector, or any combination thereof.

Embodiment 53 provides the method of embodiment 51 or 52, wherein the step of introducing into the cell comprises transfecting or transducing the cell.

Embodiment 54 provides the method of any one of embodiments 51-53, wherein the step of introducing into the cell comprises use of electroporation, injection, a gene gun, or any combination thereof.

Embodiment 55 provides a method for modifying a target DNA molecule, the method comprising contacting the target DNA molecule with the variant polypeptide of any one of embodiments 1-32 and the RNA guide of any previous embodiment.

Embodiment 56 provides the method of embodiment 55, wherein the target DNA molecule is in vitro or in a cell.

Embodiment 57 provides the method of any one of embodiments 51-54, and 56, wherein the cell is in vitro, ex vivo, or in vivo.

Embodiment 58 provides the method of embodiment 57, wherein the cell is selected from a prokaryotic cell, a eukaryotic cell, a plant cell, a mammalian cell, and a human cell.

Other Embodiments

The disclosures of each and every patent, patent application, and publication cited herein are hereby incorporated herein by reference in their entirety. While this disclosure has been described with reference to specific embodiments, it is apparent that other embodiments and variations of this disclosure may be devised by others skilled in the art without departing from the true spirit and scope of the invention. The appended claims are intended to be construed to include all such embodiments and equivalent variations.

What is claimed is:

1. A variant polypeptide that comprises a substitution that corresponds to a substitution in the polypeptide of SEQ ID NO: 3 selected from D509R, S511R, I521R, D535G, Q514G, L516R, L516G, E198R, S527R, D509K, D509G, L580G, V359R, D535K, Y381R, R354G, M380K, M380R, V383R, L580R, E367R, I521K, E367G, E507R, I521G, W350R, D535R, R528K, S527K, L385G, W350G, L516K, Y381G, H532R, D129R, P615R, G578R, M380G, V595G, R531G, D129G, R531K, D158G, N476G, G578K, A512R, P618R, V595R, V595K, V383G, A597G, Y381K, P618G, E198K, T288K, E507K, L385R, C538G, P615G, D386R, S511K, C371G, K136G, N220R, S78K, K141G, K240R, D277R, T165R, and K374R, and wherein the variant polypeptide comprises:
   (a) at least 98% sequence identity to the polypeptide of SEQ ID NO: 3; or
   (b) an amino acid sequence that differs from SEQ ID NO: 3 solely by the modification of 1-13 amino acids within SEQ ID NO: 3; and
   wherein the variant polypeptide has nuclease activity.

2. The variant polypeptide of claim 1, wherein the substitution corresponds to a substitution in the polypeptide of SEQ ID NO: 3 selected from the group consisting of:
   i) D509R;
   ii) S511R;
   iii) I521R;
   iv) D535G; and
   v) Q514G.

3. The variant polypeptide of claim 1, wherein the variant polypeptide further comprises a second substitution that corresponds to a substitution in the polypeptide of SEQ ID NO: 3.

4. The variant polypeptide of claim 3, wherein:
   i) the substitution corresponds to the substitution L580G in the polypeptide of SEQ ID NO: 3 and the second substitution corresponds to the substitution L385G in the polypeptide of SEQ ID NO: 3;
   ii) the substitution corresponds to the substitution D509R in the polypeptide of SEQ ID NO: 3 and the second substitution corresponds to the substitution M380R in the polypeptide of SEQ ID NO: 3;
   iii) the substitution corresponds to the substitution L580G in the polypeptide of SEQ ID NO: 3 and the second substitution corresponds to the substitution A512R in the polypeptide of SEQ ID NO: 3;
   iv) the substitution corresponds to the substitution S527R in the polypeptide of SEQ ID NO: 3 and the second substitution corresponds to the substitution C538G in the polypeptide of SEQ ID NO: 3;
   v) the substitution corresponds to the substitution D129R in the polypeptide of SEQ ID NO: 3 and the second substitution corresponds to the substitution P618R in the polypeptide of SEQ ID NO: 3; or
   vi) the substitution corresponds to the substitution Q514G in the polypeptide of SEQ ID NO: 3 and the second substitution corresponds to the substitution A512R in the polypeptide of SEQ ID NO: 3.

5. The variant polypeptide of claim 3, wherein the variant polypeptide further comprises a third substitution that corresponds to a substitution in the polypeptide of SEQ ID NO: 3.

6. The variant polypeptide of claim 5, wherein:
   i) the substitution corresponds to the substitution D535G in the polypeptide of SEQ ID NO: 3, the second substitution corresponds to the substitution L516R in the polypeptide of SEQ ID NO: 3, and the third substitution corresponds to the substitution I521R in the polypeptide of SEQ ID NO: 3;
   ii) the substitution corresponds to the substitution L516R in the polypeptide of SEQ ID NO: 3, the second substitution corresponds to the substitution Q514G in the polypeptide of SEQ ID NO: 3, and the third substitution corresponds to the substitution I521R in the polypeptide of SEQ ID NO: 3;
   iii) the substitution corresponds to the substitution D509R in the polypeptide of SEQ ID NO: 3, the second substitution corresponds to the substitution L516R in the polypeptide of SEQ ID NO: 3, and the third substitution corresponds to the substitution I521R in the polypeptide of SEQ ID NO: 3;
   iv) the substitution corresponds to the substitution D535G in the polypeptide of SEQ ID NO: 3, the second substitution corresponds to the substitution L516R in the polypeptide of SEQ ID NO: 3, and the third substitution corresponds to the substitution Q514G in the polypeptide of SEQ ID NO: 3;
   v) the substitution corresponds to the substitution D535G in the polypeptide of SEQ ID NO: 3, the second substitution corresponds to the substitution Q514G in the polypeptide of SEQ ID NO: 3, and the third substitution corresponds to the substitution I521R in the polypeptide of SEQ ID NO: 3;

vi) the substitution corresponds to the substitution K136G in the polypeptide of SEQ ID NO: 3, the second substitution corresponds to the substitution N220R in the polypeptide of SEQ ID NO: 3, and the third substitution corresponds to the substitution M380R in the polypeptide of SEQ ID NO: 3;

vii) the substitution corresponds to the substitution S78K in the polypeptide of SEQ ID NO: 3, the second substitution corresponds to the substitution E198R in the polypeptide of SEQ ID NO: 3, and the third substitution corresponds to the substitution R354G in the polypeptide of SEQ ID NO: 3;

viii) the substitution corresponds to the substitution K141G in the polypeptide of SEQ ID NO: 3, the second substitution corresponds to the substitution N220R in the polypeptide of SEQ ID NO: 3, and the third substitution corresponds to the substitution M380R in the polypeptide of SEQ ID NO: 3;

ix) the substitution corresponds to the substitution K141G in the polypeptide of SEQ ID NO: 3, the second substitution corresponds to the substitution K240R in the polypeptide of SEQ ID NO: 3, and the third substitution corresponds to the substitution M380R in the polypeptide of SEQ ID NO: 3; or x) the substitution corresponds to the substitution K141G in the polypeptide of SEQ ID NO: 3, the second substitution corresponds to the substitution D277R in the polypeptide of SEQ ID NO: 3, and the third substitution corresponds to the substitution M380R in the polypeptide of SEQ ID NO: 3.

7. The variant polypeptide of claim 5, wherein the variant polypeptide further comprises a fourth substitution that corresponds to a substitution in the polypeptide of SEQ ID NO: 3.

8. The variant polypeptide of claim 7, wherein the substitution corresponds to the substitution Q514G in the polypeptide of SEQ ID NO: 3, the second substitution corresponds to the substitution I521R in the polypeptide of SEQ ID NO: 3, the third substitution corresponds to the substitution L580G in the polypeptide of SEQ ID NO: 3, and the fourth substitution corresponds to the substitution E198R in the polypeptide of SEQ ID NO: 3.

9. The variant polypeptide of claim 7, wherein the variant polypeptide further comprises a fifth substitution that corresponds to a substitution in the polypeptide of SEQ ID NO: 3.

10. The variant polypeptide of claim 9, wherein the substitution corresponds to the substitution D509R in the polypeptide of SEQ ID NO: 3, the second substitution corresponds to the substitution D535G in the polypeptide of SEQ ID NO: 3, the third substitution corresponds to the substitution L516R in the polypeptide of SEQ ID NO: 3, the fourth substitution corresponds to the substitution Q514G in the polypeptide of SEQ ID NO: 3, and the fifth substitution corresponds to the substitution I521R in the polypeptide of SEQ ID NO: 3.

11. The variant polypeptide of claim 1, wherein the variant polypeptide is capable of binding to an RNA guide.

12. The variant polypeptide of claim 1, wherein:
(i) the variant polypeptide exhibits enhanced nuclease activity and/or enhanced stability relative to the polypeptide of SEQ ID NO: 3; and/or
(ii) the variant polypeptide exhibits enhanced binding or specificity to an RNA guide relative to the polypeptide of SEQ ID NO: 3, wherein the RNA guide comprises the sequence of SEQ ID NO: 6.

13. The variant polypeptide of claim 12, wherein the variant polypeptide comprises an enhanced nuclease activity of at least 1.5-fold relative to the polypeptide of SEQ ID NO: 3.

14. The variant polypeptide of claim 1, wherein:
(i) the variant polypeptide comprises a RuvC domain or a split RuvC domain;
(ii) the variant polypeptide comprises one or more catalytic residues;
(iii) the variant polypeptide comprises one or more catalytic residues, wherein the one or more catalytic residues are an Asp at the position corresponding to position 345 of the polypeptide of SEQ ID NO: 3 and/or a Glu at the position corresponding to position 506 of the polypeptide of SEQ ID NO: 3;
(iv) the variant polypeptide has reduced nuclease activity compared to the polypeptide of SEQ ID NO: 3; and/or
(v) the variant polypeptide further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

15. A system comprising the variant polypeptide of claim 1, and an RNA guide or a nucleic acid encoding the RNA guide, wherein the RNA guide comprises a direct repeat and a spacer sequence.

16. The system of claim 15, wherein the direct repeat sequence comprises a nucleotide sequence with at least 90% sequence identity to SEQ ID NO: 4, SEQ ID NO: 5, or SEQ ID NO: 6.

17. A composition comprising the variant polypeptide of claim 1, wherein the composition is present in a nanoparticle, a liposome, an exosome, a microvesicle, or a gene-gun.

18. A cell comprising the variant polypeptide of claim 1.

19. The variant polypeptide of claim 1, wherein the variant polypeptide comprises at least 99% sequence identity to the polypeptide of SEQ ID NO: 3.

20. The variant polypeptide of claim 1, wherein the substitution corresponds to the substitution D509R in the polypeptide of SEQ ID NO: 3.

* * * * *

UNITED STATES PATENT AND TRADEMARK OFFICE
CERTIFICATE OF CORRECTION

PATENT NO. : 12,344,870 B2
APPLICATION NO. : 17/930595
DATED : July 1, 2025
INVENTOR(S) : Shaorong Chong et al.

Page 1 of 1

It is certified that error appears in the above-identified patent and that said Letters Patent is hereby corrected as shown below:

In the Claims

At Column 113, Claim number 1, Line number 29, delete "V383R, L580R, E367R, I521K, E367G, E507R, I521G," and insert --V383R, L580R, E367R, I521K, E367G, E507R, I521G--.

Signed and Sealed this
Second Day of September, 2025

Coke Morgan Stewart
*Acting Director of the United States Patent and Trademark Office*

SEQUENCE LISTING

```
Sequence total quantity: 29
SEQ ID NO: 1            moltype = DNA  length = 1962
FEATURE                 Location/Qualifiers
source                  1..1962
                        mol_type = other DNA
                        organism = synthetic construct
SEQUENCE: 1
atgggtgcgg ctcgtcgccg taacccgaag gttgcagcgg cgcgtaaggg caagccgccg  60
ccgaaagcaa ccggtaactg ccgtaattac cgctatggtg cgcacgaacc gatcgcgaat  120
ctggacaagg tgctggacga gatgcgtggc gcgcatgacc tgcgcaacgt tttgacctgt  180
atcaatcgtg cgcgctccga gatgattacg gctgcactgg gtgaacacca gtcttacaag  240
aaggcgaccg cagacctggc ggcattgcat cagcgccgtg ataagctgga agcgcaaatc  300
cgtcagcaga acagcgcgag ccgtaaacgt ctgggtcgtc acagcccgct gagcagcgag  360
ctggacaccg ttcgtaagcg cattgatgag ggtcgtacgg cgctgaagaa gctgcgccgt  420
aagctgctga agaaggaccc ggccctgaaa gcggtggttg aggctgcaga cgatatggcg  480
aaacgtgaaa ccacccgtgc ggaagatgca tgcggcctgt attggtgtac ccgtaacgaa  540
cagacgggca agcgtgcgaa actgcgccgt ttcaagaaat ggcgtgacag cgaggcgacc  600
atcagcgtgc aaattccggg tggcctgacc gttgagcagc tgctgggtgg tgagaacaat  660
caagcacgtc tggagctgcg tccggaaggc gtgtgggttc agggtgcgcg taaacgtaaa  720
gtggaaccgg cagaagcggc acgtaacaag ctgcgtctgg acgaagatgg ctacccgatg  780
cgtaaactgg gcaccgcgat tctgcacctg cgttgcatga gcgacgagga tggcaagccg  840
atctgggcgg aagttccgat tacctatcat cgtgagatcc cggctgatgc aaagattaaa  900
cgttgttacc tgcaccgttt ccgcgtgggt aatcgttatc attggtccgt tcgttttagc  960
ctggagcgcg gtaagaaagg cgacgatagc tggctgcacc cgcgtgtggc aaccaccggc  1020
accgctgcaa tcgacattgg ttggcgttgg tttccggatc gtctgcgtgt tgcggtgtgg  1080
gcaggtagcg acggcgcgga gggtgaactg tgcttgccga aatggtggct ggatgaaatg  1140
tacagcgtgc gtctggacca gcgtgagcgc gatgttctgt tcaacgaaat cgtgagcctg  1200
gttttgccgt ggtttcgtag ccgtcgtggt gagctgtctg actatgtcgt gcaagcgatt  1260
aagaccatgc attcttggcg tgataaaggc cgcctggcgg cattgagcat gcgttggcgt  1320
gatgatctgg ctgcggaccc gggtgctaac ccggcacatg tggccatgag catccgtctg  1380
gaggaatggc gtaagcgcga caaacatatt tggtgcgagg aagttaacct gcgtagccag  1440
ttgcaaggca gccgtaagga tctgtatcgc cgtttcgcgg caatgctgac cagccgttat  1500
ggtcgcatcg ttgtcgagga atttgatctg agcgcagtgc agaagctgcc gccggctagc  1560
attgacgatg gcacctacag ccgtgtgaag cgccacaaag gtgatgctgc atgcagccat  1620
ctggttggtg cgctgaagga cgccgcgcgt caactggata agaaaaaccc gaagtggacc  1680
acgaaacgtt gccacgtttg tggcaagacc gagcgtaaat gggaaaatcc gggcgagctg  1740
gaacacacct gcaaacattg tggtgtcctg tgggaccgtg atgtgaacgc tgcacgcaat  1800
atcctggccg cgagcggcgt tgcggttgac tggacccgtc cgccgctggc accggctgca  1860
cgtatgacct atccgcaggt tgagaaccgt gaaatgcgcc gtagccgccg tcgcaaagag  1920
gcgctggaaa ccacccgtgc gtccggtgat cgccaaaccg cg                    1962

SEQ ID NO: 2            moltype = DNA  length = 1962
FEATURE                 Location/Qualifiers
source                  1..1962
                        mol_type = other DNA
                        organism = synthetic construct
SEQUENCE: 2
```

-continued

```
atgggcgccg ctcggagaag gaaccctaag gtggcagcag ctcgtaaggg caagccacct    60
ccaaaagcca ccggcaactg ccggaattac agatatgggg cacacgaacc aatcgccaat   120
ctggacaagg tcctcgatga gatgcgaggg gcacatgacc tgcgcaacgt gctgacttgt   180
atcaatcggg ctagatccga gatgattacc gcagccctgg gagaacacca gtcttacaag   240
aaagctacag cagacctggc cgccctgcat cagcgccgga ataagctgga ggcacagatc   300
aggcagcaga actctgccag taggaaacgc ctgggacgcc acagcccact gagctccgaa   360
ctcgacacag tgcgaaaacg tattgatgag ggcagaactg ccctgaagaa actgcggcgg   420
aagctgctga agaaggaccc cgcactgaaa gcagtggtcg aggcagctga cgatatggcc   480
aaaagggaga ccacacgcgc tgaagatgca tgcggtctgt attggtgtac taggaatgaa   540
cagaccggca agcgcgccaa actgagaagg ttcaagaaat ggagggactc cgaggctacc   600
atctctgtcc agattcccgg cgggctgaca gttgagcagc tgctcggagg tgaaaacaat   660
caggcacgac tggagctccg tcctgaaggg gtgtgggtcc agggagctcg aagagaaaa    720
gtggagccag cagaagcagc cagaaacaag ctgcggctgg acgaggatgg ttaccctatg   780
aggaaactgg gcactgccat cctgcacctg cgctgcatgt ccgacgagga tggcaagcct   840
atctgggccg aagtgccaat tacctatcat cgggagatcc ccgccgatgc taagatcaag   900
cggtgctacc tgcacaggtt ccgcgtgggg aataggtatc attggtcagt ccggtttagc   960
ctggagagag caagaaagg ggacgatagc tggctgcacc ccgggtggc aactaccggt   1020
accgctgcaa tcgacattgg atggagatgg tttcctgatc gactgcgtgt tgccgtgtgg   1080
gctggatccg acggtgcaga gggtgaactg tgcctcccca gtggtggct ggatgagatg   1140
tacagcgtgc ggctggacca gcgggagaga gatgtgctgt tcaacgaaat cgtgagtctg   1200
gtgctgcctt ggtttcgcag ccgccgaggc gagctgtccg actatgttgt gcaggccatt   1260
aagacaatgc attcatggcg cgataaaggg cgactggtcg ccctgagcat gaggtggcgc   1320
gacgatctgg cagcagaccc caggagcaaac ccagcacacg tggctatgtc tatcagactg   1380
gaggaatggc gaaagcgtga caaacatatt tggtgcgagg aagtcaatct gcggagtcag   1440
ctccagggca gccggaagga cctgtaccgg cggttcgctg caatgctgac aagtaggtac   1500
gggcgcatcg tcgttgagga attttgacctg tcagccgtgc agaaactccc gcccgcttct   1560
attgacgatg gcacttacag tcgagtgaag cgtcacaaag agatgccgc ttgttctcat   1620
ctggtcggcg ccctgaagga cgcagcacgt cagctggata agaaaaaccc aaagtggaca   1680
actaaacggt gccacgtgtg cggcaagacc gagagaaaat gggaaatcc cggggagctg   1740
gagcacacat gcaagcattg tggcgtgctg tgggaccggg atgtgaacgc tgcaagaaat   1800
atcctggcag ctagcggtgt cgcagttgac tggacaaggc ctccactggc tccagcagca   1860
cgtatgactt atccccaggt ggagaataga gaaatgcggc ggagccggcg gcggaaggag   1920
gctctggaaa ccacaagggc atccggcgat cgccagaccg cc                      1962

SEQ ID NO: 3          moltype = AA   length = 654
FEATURE               Location/Qualifiers
source                1..654
                      mol_type = protein
                      organism = synthetic construct
SEQUENCE: 3
MGAARRRNPK VAAARKGKPP PKATGNCRNY RYGAHEPIAN LDKVLDEMRG AHDLRNVLTC    60
INRARSEMIT AALGEHQSYK KATADLAALH QRRDKLEAQI RQQNSASRKR LGRHSPLSSE   120
LDTVRKRIDE GRTALKKLRR KLLKKDPALK AVVEAADDMA KRETTRAEDA CGLYWCTRNE   180
QTGKRAKLRR FKKWRDSEAT ISVQIPGGLT VEQLLGGENN QARLELRPEG VWVQGARKRK   240
VEPAEAARNK LRLDEDGYPM RKLGTAILHL RCMSDEDGKP IWAEVPITYH REIPADAKIK   300
RCYLHRFRVG NRYHWSVRFS LERGKKGDDS WLHPRVATTG TAAIDIGWRW FPDRLRVAVW   360
AGSDGAEGEL CLPKWWLDEM YSVRLDQRER DVLFNEIVSL VLPWFRSRRG ELSDYVVQAI   420
KTMHSWRDKG RLAALSMRWR DDLAADPGAN PAHVAMSIRL EEWRKRDKHI WCEEVNLRSQ   480
LQGSRKDLYR RFAAMLTSRY GRIVVEEFDL SAVQKLPPAS IDDGTYSRVK RHKGDAACSH   540
LVGALKDAAR QLDKKNPKWT TKRCHVCGKT ERKWENPGEL EHTCKHCGVL WDRDVNAARN   600
ILAASGVAVD WTRPPLAPAA RMTYPQVENR EMRRSRRRKE ALETTRASGD RQTA         654

SEQ ID NO: 4          moltype = RNA  length = 35
FEATURE               Location/Qualifiers
source                1..35
                      mol_type = other RNA
                      organism = synthetic construct
SEQUENCE: 4
ctcgcggtcc catcggaacg ggttgtggtt ccgac                                35

SEQ ID NO: 5          moltype = RNA  length = 36
FEATURE               Location/Qualifiers
source                1..36
                      mol_type = other RNA
                      organism = synthetic construct
SEQUENCE: 5
ctcgcggtcc catcggaacg ggtttgtggt tccgac                               36

SEQ ID NO: 6          moltype = RNA  length = 30
FEATURE               Location/Qualifiers
source                1..30
                      mol_type = other RNA
                      organism = synthetic construct
SEQUENCE: 6
ggtcccatcg gaacgggttg tggttccgac                                      30

SEQ ID NO: 7          moltype = RNA  length = 12
FEATURE               Location/Qualifiers
source                1..12
```

```
                        mol_type = other RNA
                        organism = synthetic construct
SEQUENCE: 7
tgtggttccg ac                                                              12

SEQ ID NO: 8           moltype = DNA   length = 25
FEATURE                Location/Qualifiers
source                 1..25
                       mol_type = unassigned DNA
                       organism = unidentified
SEQUENCE: 8
gtgaacacct aggacgcacc attct                                                25

SEQ ID NO: 9           moltype = RNA   length = 55
FEATURE                Location/Qualifiers
source                 1..55
                       mol_type = other RNA
                       organism = synthetic construct
SEQUENCE: 9
ggtcccatcg gaacggggttg tggttccgac gtgaacacct aggacgcacc attct              55
```

```
                        mol_type = other RNA
                        organism = synthetic construct
SEQUENCE: 7
tgtggttccg ac                                                              12

SEQ ID NO: 8            moltype = DNA   length = 25
FEATURE                 Location/Qualifiers
source                  1..25
                        mol_type = unassigned DNA
                        organism = unidentified
SEQUENCE: 8
gtgaacacct aggacgcacc attct                                                25

SEQ ID NO: 9            moltype = RNA   length = 55
FEATURE                 Location/Qualifiers
source                  1..55
                        mol_type = other RNA
                        organism = synthetic construct
SEQUENCE: 9
ggtcccatcg gaacgggttg tggttccgac gtgaacacct aggacgcacc attct               55

SEQ ID NO: 10           moltype = DNA   length = 25
FEATURE                 Location/Qualifiers
source                  1..25
                        mol_type = unassigned DNA
                        organism = unidentified
SEQUENCE: 10
gccctggctt tggcagcctg tgctg                                                25

SEQ ID NO: 11           moltype = RNA   length = 55
FEATURE                 Location/Qualifiers
source                  1..55
                        mol_type = other RNA
                        organism = synthetic construct
SEQUENCE: 11
ggtcccatcg gaacgggttg tggttccgac gccctggctt tggcagcctg tgctg               55

SEQ ID NO: 12           moltype = DNA   length = 25
FEATURE                 Location/Qualifiers
source                  1..25
                        mol_type = unassigned DNA
                        organism = unidentified
SEQUENCE: 12
tgcctgaagt cgccatccaa agctt                                                25

SEQ ID NO: 13           moltype = RNA   length = 55
FEATURE                 Location/Qualifiers
source                  1..55
                        mol_type = other RNA
                        organism = synthetic construct
SEQUENCE: 13
ggtcccatcg gaacgggttg tggttccgac tgcctgaagt cgccatccaa agctt               55

SEQ ID NO: 14           moltype = DNA   length = 25
FEATURE                 Location/Qualifiers
source                  1..25
                        mol_type = unassigned DNA
                        organism = unidentified
SEQUENCE: 14
aatagtccct tgctaaagaa acatg                                                25

SEQ ID NO: 15           moltype = RNA   length = 55
FEATURE                 Location/Qualifiers
source                  1..55
                        mol_type = other RNA
                        organism = synthetic construct
SEQUENCE: 15
ggtcccatcg gaacgggttg tggttccgac aatagtccct tgctaaagaa acatg               55

SEQ ID NO: 16           moltype = DNA   length = 25
FEATURE                 Location/Qualifiers
source                  1..25
                        mol_type = unassigned DNA
                        organism = unidentified
SEQUENCE: 16
tgctttgttg acattgtcca cacct                                                25

SEQ ID NO: 17           moltype = RNA   length = 55
FEATURE                 Location/Qualifiers
```

```
source                          1..55
                                mol_type = other RNA
                                organism = synthetic construct
SEQUENCE: 17
ggtcccatcg gaacgggttg tggttccgac tgctttgttg acattgtcca cacct          55

SEQ ID NO: 18                   moltype = DNA   length = 25
FEATURE                         Location/Qualifiers
source                          1..25
                                mol_type = unassigned DNA
                                organism = unidentified
SEQUENCE: 18
agtgccccc cttcttgggg gcttt                                             25

SEQ ID NO: 19                   moltype = RNA   length = 55
FEATURE                         Location/Qualifiers
source                          1..55
                                mol_type = other RNA
                                organism = synthetic construct
SEQUENCE: 19
ggtcccatcg gaacgggttg tggttccgac agtgccccc cttcttgggg gcttt            55

SEQ ID NO: 20                   moltype = DNA   length = 25
FEATURE                         Location/Qualifiers
source                          1..25
                                mol_type = unassigned DNA
                                organism = unidentified
SEQUENCE: 20
tacctctttc ctttgcccat actgg                                            25

SEQ ID NO: 21                   moltype = RNA   length = 55
FEATURE                         Location/Qualifiers
source                          1..55
                                mol_type = other RNA
                                organism = synthetic construct
SEQUENCE: 21
ggtcccatcg gaacgggttg tggttccgac tacctctttc ctttgcccat actgg           55

SEQ ID NO: 22                   moltype = DNA   length = 25
FEATURE                         Location/Qualifiers
source                          1..25
                                mol_type = unassigned DNA
                                organism = unidentified
SEQUENCE: 22
tgcccattgg tggtctggat aaaag                                            25

SEQ ID NO: 23                   moltype = RNA   length = 55
FEATURE                         Location/Qualifiers
source                          1..55
                                mol_type = other RNA
                                organism = synthetic construct
SEQUENCE: 23
ggtcccatcg gaacgggttg tggttccgac tgcccattgg tggtctggat aaaag           55

SEQ ID NO: 24                   moltype = RNA   length = 50
FEATURE                         Location/Qualifiers
source                          1..50
                                mol_type = other RNA
                                organism = synthetic construct
SEQUENCE: 24
ggtcccatcg gaacgggttg tggttccgac ggagggatac attggtgggg                 50

SEQ ID NO: 25                   moltype = RNA   length = 50
FEATURE                         Location/Qualifiers
source                          1..50
                                mol_type = other RNA
                                organism = synthetic construct
SEQUENCE: 25
ggtcccatcg gaacgggttg tggttccgac aggccacagg gacccaactg                 50

SEQ ID NO: 26                   moltype = RNA   length = 50
FEATURE                         Location/Qualifiers
source                          1..50
                                mol_type = other RNA
                                organism = synthetic construct
SEQUENCE: 26
ggtcccatcg gaacgggttg tggttccgac cggccagttt ttccgtacgg                 50

SEQ ID NO: 27                   moltype = DNA   length = 20
```

```
FEATURE                 Location/Qualifiers
source                  1..20
                        mol_type = unassigned DNA
                        organism = unidentified
SEQUENCE: 27
ggagggatac attggtgggg                                                    20

SEQ ID NO: 28           moltype = DNA  length = 20
FEATURE                 Location/Qualifiers
source                  1..20
                        mol_type = unassigned DNA
                        organism = unidentified
SEQUENCE: 28
aggccacagg gacccaactg                                                    20

SEQ ID NO: 29           moltype = DNA  length = 20
FEATURE                 Location/Qualifiers
source                  1..20
                        mol_type = unassigned DNA
                        organism = unidentified
SEQUENCE: 29
cggccagttt ttccgtacgg                                                    20
```